United States Patent
Nagata et al.

(10) Patent No.: US 7,223,409 B2
(45) Date of Patent: May 29, 2007

(54) DNA-BASED VACCINE AGAINST THE ENCEPHALITIS ALPHAVIRUSES

(75) Inventors: Leslie P. Nagata, Medicine Hat (CA); Jonathon P. Wong, Medicine Hat (CA)

(73) Assignee: The Minister of National Defence, Government of Canada, Ontario (CA)

( * ) Notice: Subject to any disclaimer, the term of this patent is extended or adjusted under 35 U.S.C. 154(b) by 0 days.

(21) Appl. No.: 10/921,868

(22) Filed: Aug. 20, 2004

(65) Prior Publication Data

US 2005/0118251 A1 Jun. 2, 2005

Related U.S. Application Data

(62) Division of application No. 10/023,649, filed on Dec. 21, 2001, now Pat. No. 6,800,289.

(60) Provisional application No. 60/256,948, filed on Dec. 21, 2000.

(51) Int. Cl.
*A61K 39/21* (2006.01)
(52) U.S. Cl. .............................. 424/207.1; 424/204.1; 435/91.1
(58) Field of Classification Search ............. 424/207.1, 424/204.1; 435/91.1
See application file for complete search history.

(56) References Cited

U.S. PATENT DOCUMENTS 6,261,570 B1 * 7/2001 Parker et al. ............. 424/205.1

OTHER PUBLICATIONS

Netolitzky et al, Journal of General Virology, Jan. 2000, vol. 81, pp. 151-159.*
Bell et al, Journal of Virology, Feb. 1983, vol. 45, No. 2, pp. 708-714.*
Pertmer et al, Vaccine, 1995, vol. 13, No. 15, pp. 1427-1430.*
Wong et al, Vaccine, 1999, pp. 1788-1795.*
Nagata et al. Vaccine, 2005, vol. 23, pp. 2280-2283.*
Weaver et al., "Recombinational History of Molecular Evolution of Western Equine Encephalomyelitis Complex Alphaviruese," Journal of Virology, vol. 71, No. 1.pp. 613-623 (1997).
Weaver et al., "A comparison of the Nuecleotide Sequences of Eastern and Western Equine Encephaloyeltiis Viruses with those of other Alphaviruses and Related RNA Viruses," 197 Virology 375-390 (1993).
Hahn et al., "Western equine encephalitis virus is a recombinant virus,".Proc. Natl. Acad. Sci. USA vol. 85, pp. 5997-6001 (Aug. 1988).

* cited by examiner

*Primary Examiner*—Ali R. Salimi
(74) *Attorney, Agent, or Firm*—Rader, Fishman & Grauer PLLC

(57) ABSTRACT

This invention relates to the development of a mammalian expression vector, under which expression of the structural genes of western equine encephalitis virus have been placed under the control of an eucaryotic promoter. When the recombinant vector is administered to mammalian cell culture or using a cell-free transcription/translation system, in vitro, authentic structural proteins of western equine encephalitis virus are produced as verified by reactivity with monoclonal antibodies developed to western equine encephalitis virus. When the recombinant DNA molecule is administered in vivo, a protective immune response is induced, thereby enhancing protection of the individual against subsequent infection by western equine encephalitis virus. In a similar manner, DNA vaccines to related alphaviruses (Venezuelan and eastern equine encephalitis viruses) could also be developed.

7 Claims, 11 Drawing Sheets

Figure 2 Multiple sequence alignment (a)
```
1    ATAGGGCATGGTATAGAGGCACCTACCCTACAAACAAATC    CBA87
1    ---------------------------ACCCTACAAACTAATC    71V-1658
1    ATAGGGTATGGTGTAGAGGCAACCACCCTATTTCC--ACC    EEE
1    ATGGGCGGCGCAAGAGAGAAGCCCAAACCAATT----ACC    VEE 41   GATCCAATATGGAAAGAATTCACGTTGACTTAGACGCTGA    CBA87
17   GATCCAATATGGAAAGAATTCACGTTGACTTAGATGCTGA    71V-1658
39   TATCCAAAATGGAGAAAGTTCATGTTGACTTAGACGCAGA    EEE
37   TACCCAAAATGGAGAAAGTTCACGTTGACATCGAGGAAGA    VEE 81   CAGCCCATATGTCAAGT                          CBA87
57   CAGCCCGTATGTCAAGTCGTTACAGCGGACGTTTCCACAA    71V-1658
79   CAGCCCATTCGTCAAGTCACTGCAAGATGCTTTCCACAT    EEE
77   CAGCCCATTCCTCAGAGCTTTACAACGGAGCTTCCCGCAG    VEE 97
97   TTTGAGATCGAAGCAAGGCAGGTCACTGACAATGACCATG    71V-1658
119  TTTGAGATAGAAGCAACGCAGGTCACTGACAATGACCATG    EEE
117  TTTGAGGTAGAAGCCAAGCAGGTCACTGATAATGACCATG    VEE 97
137  CCAATGCCAGAGCGTTTTCGCATGTGGCAACAAAGCTCAT    71V-1658
159  CTAATGCTAGGGCGTTTTCGCACCTAGCTACTAAGCTCAT    EEE
157  CTAATGCCAGAGCGTTTTTCGCATCTGGCTTCAAAACTGAT    VEE 97
177  TGAGAGCGAAGTCGACCGGGACCAAGTTATCTTGGACAT    71V-1658
199  TGAGGGAGAAGTGGATACAGACCAGGTGATCCTGGATATT    EEE
197  CGAAACGGAGTGGACCCATCCGACACGATCCTTGACATT    VEE
```

(b)
```
CTCGATATGGGCTTCCGCCGTAGGCTCAAG    71V-1658
CCTGATATAGGGCTTCCGCGTAGGTCCAGG    WEE-5614
CTCGATATAGGATTGCGTCGCCGAATTAAG    EEE
``` a. The 5' terminus of WEE CBA87 (1-97), WEE 71V-1658 (25-240), EEE (1-238) and VEE (1-236) via Clustal module of DNAStar. Areas where sequences differ are boxed.

b. Hypervariable region identified in nsP1. Alignment of WEE 71V-1658 (1420-1449), WEE 1654 (65-94) and EEE (1415-1444) is shown.

Figure 3 Stem loop structures in the 5' NTR
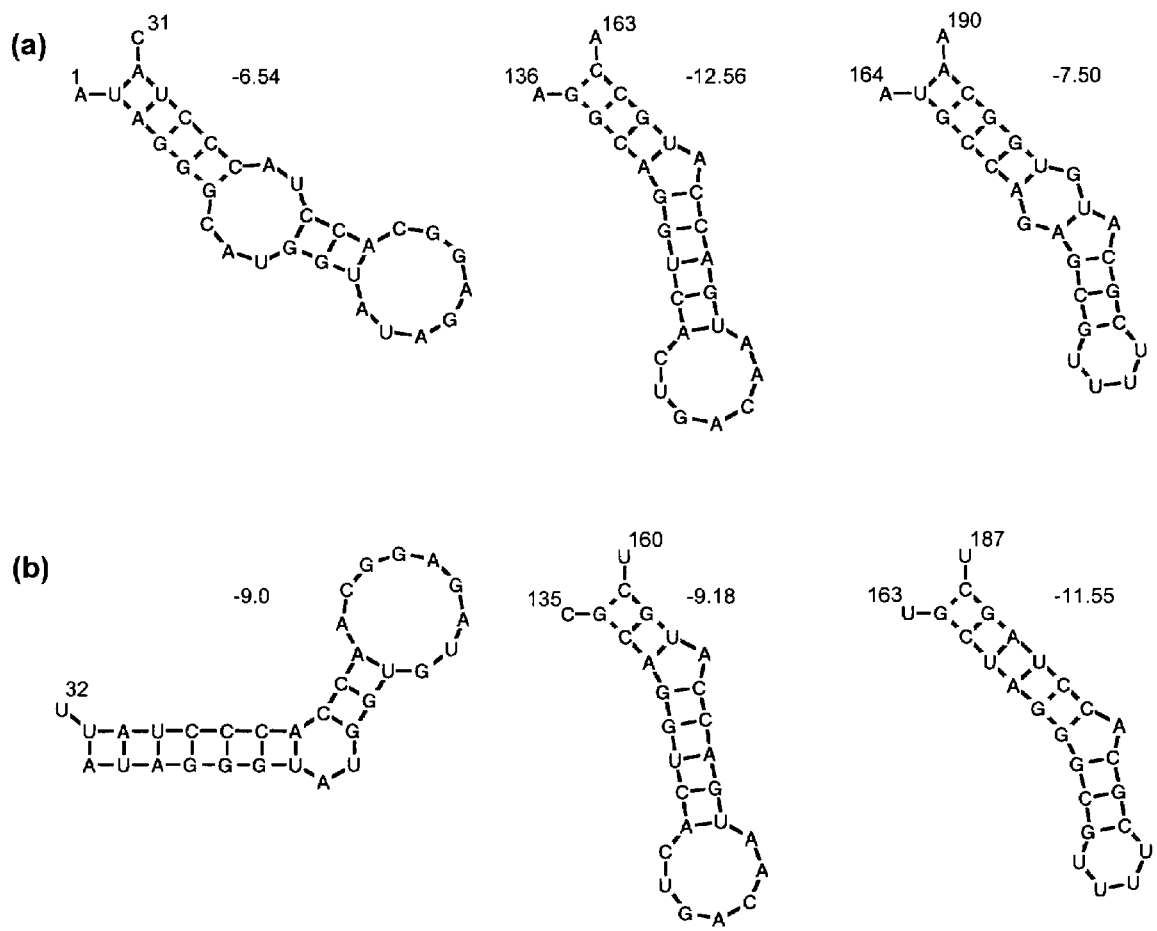
Hairpin structures were identified using the RNA folding program of the Genequest module (DNASTAR).
a. Structures for WEE (CBA87/71V-1658) sequence (1-192).
b. Structures for EEE (1-192).
Minimal free energy values are shown for the different structures.

(a) Double stem loop structures in SIN.

(b) Double stem loop structures in 3' NTR of WEE. Residues in the SIN-like 40 nt repeat are shaded.

(c) Stem loop structures in EEE.

Figure 4  Stem loop structures in the 3' NTR

Figure 5  Phylogenetic relationship of the WEE nonstructural region
         compared to other alphaviruses a) nsP1

- EEE
- 71V-1658
- VEE
- SIN
- ONN
- SF
- RR b) nsP4

- EEE
- 71V-1658
- VEE
- SIN
- RR
- SF
- ONN c) nsP1-4

- EEE
- 71V-1658
- VEE
- SIN
- ONN
- SF
- RR

Figure 6 Expression of WEE structural genes in cell culture

Figure 7  In vitro transcription and translation of WEE expression vectors

Figure 8   WEE mouse infectivity model

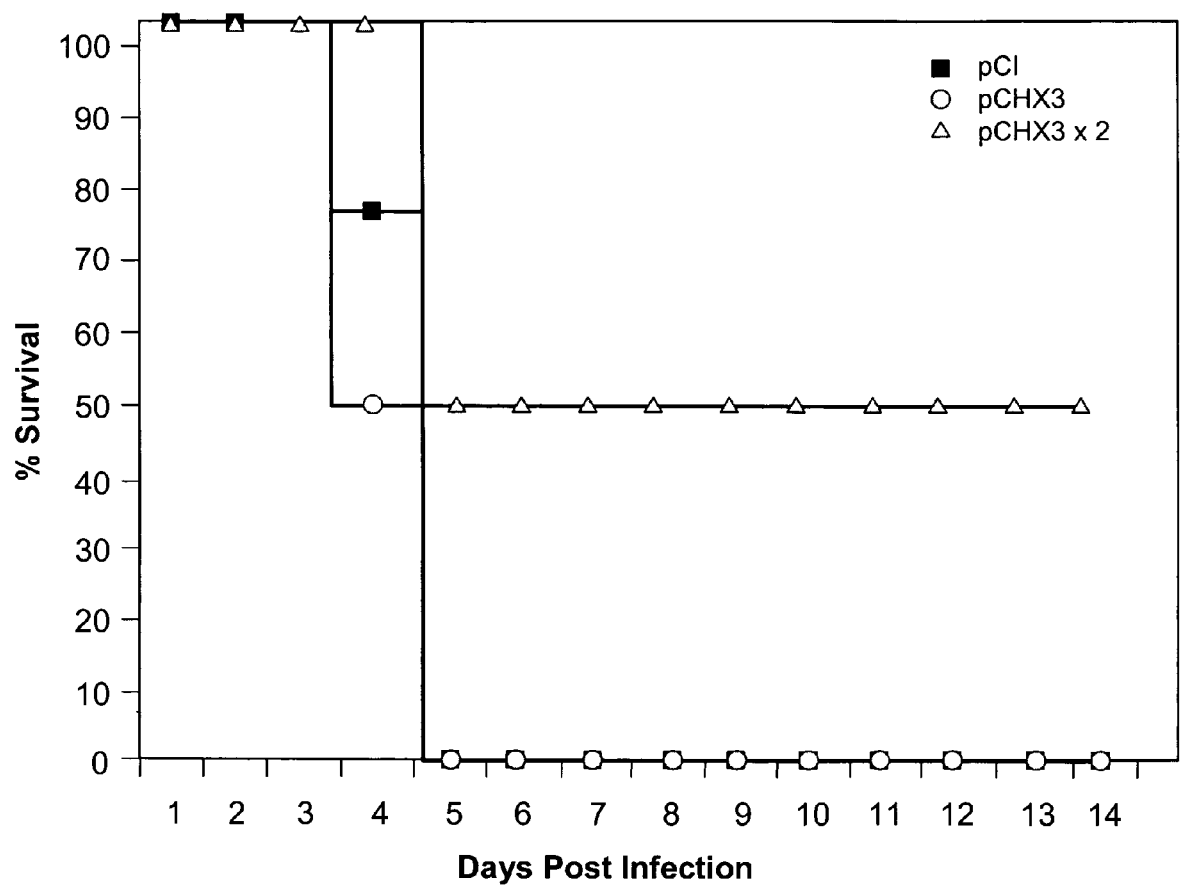
Figure 9 Protection using ballistic delivery of pCXH-3

Figure 10    Protection using ballistic delivery of pVHX-6

Figure 11  Protection using ballistic delivery of pVHX-6

DNA-BASED VACCINE AGAINST THE ENCEPHALITIS ALPHAVIRUSES

CROSS-REFERENCE TO RELATED APPLICATIONS

This application is a divisional application of Ser. No. 10/023,649 filed Dec. 21, 2001, now issued (on Oct. 5, 2004) as U.S. Pat. No. 6,800,289, which is a non-provisional application of provisional application 60/256,948 filed on Dec. 21, 2000.

FIELD OF THE INVENTION

This invention relates to the cloning, sequencing and expression of the structural genes of western equine encephalitis (WEE) virus strain 71V-1658 and the development and use of the DNA-based vaccine against WEE.

BACKGROUND OF THE INVENTION

List of Prior Art Literatures

Ausubel, F. M., et al, editors. (1995). *Current Protocols in Molecular Biology*, New York: John Wiley & Sons.

Bell, J. R., Bond, M. W., Nukapiller, M. B., Strauss, E. G., Strauss, J. H., Yamamoto, K., & Simizu, B. (1983). Structural proteins of western equine encephalitis virus: amino acid compositions and N-terminal sequences. *Journal of Virology* 45, 708–714.

Bird, B. R. & Forrester, F. T. (1981). *Basic Laboratory Techniques In Cell Culture*. Atlanta: U.S. Department of Health and Human Services, Centers for Disease Control.

Calisher, C. H. & Karabatsos, N. (1988). Arbovirus serogroups: definition and geographic distribution. In *The Arboviruses: Epidemiology and Ecology*, Vol. I, pp. 19–57. Edited by T. P Monath. CRC Press: Boca Raton, Fla.

Calisher, C. H., Shope, R. E, Brandt, W., Casals, J., Karabatsos, N., Murphy, F. A., Tesh, R. B., & Wiebe, M. E. (1980). Proposed antigenic classification of registered arbovirusess. *Intervirology* 14, 229–232.

Calisher, C. H., Karabatsos, N., Lazuick, J. S., Monath, T. P., & Wolff, K. L. (1988). Reevaluation of the western equine encephalitis antigenic complex of alphaviruses (family Togaviridae) as determined by neutralization tests. *American Journal of Tropical Medicine and Hygiene* 38, 447–452.

Cilnis, M. J., Kang, W. & Weaver, S. C. (1996). Genetic conservation of Highlands J viruses. *Virology* 218, 343–351.

Frohman, M. A., Dush, M. K. & Martin, G. R. (1988). Rapid production of full-length cDNAs from rare transcripts: Amplification using a single gene-specific oligonucleotide primer. *Proceedings of the National Academy of Science USA* 85, 8998–9002.

Hahn, C. S., Lustig, S., Strauss, E. G. & Strauss, J. H. (1988). Western Equine Encephalitis virus is a recombinant virus. *Proceedings of the National Academy of Science USA* 85, 5997–6001.

Johnson, R. E. & Peters, C. J. (1996). Alphaviruses. In *Fields Virology*, 3rd edn, pp. 843–898. Edited by B. N. Fields, et al., New York: Raven Press.

Kuhn, R., Hong, Z. & Strauss, J. H. (1990). Mutagenesis of the 3' nontranslated region of Sindbis virus RNA. *Journal of Virology* 64, 1465–1476.

Kuhn, R. J., Niesters, H. G. M., Hong, Z. & Strauss, J. H. (1991). Infectious RNA transcripts from Ross River virus cDNA clones and the construction and characterization of defined chimeras with Sindbis. *Virology* 182, 430–441.

Krieg, A. M., Yi, A.-K, Schorr, J. and Davis, H. L. (1998). The role of CpG dinucleotides in DNA vaccines. *Trends Microbiol.* 6, 23–27.

McCluskie, M. J., Davies, H. L. (1999). Novel strategies using DNA for the induction of mucosal immunity. *Critic. Rev. in Immunol.* 19, 303–329.

Ou, J.-H., Trent, D. W. & Strauss, J. H. (1982). The 3' non-coding regions of alphavirus RNAs contain repeating sequences. *Journal of Molecular Biology* 156, 719–730.

Ou, J-H., Strauss, E. G. & Strauss, J. H. (1983). The 5' terminal sequences of the genomic RNAs of several alphaviruses. *Journal of Molecular Biology* 168, 1–15.

Pardoll, D R, Beckering, A M. (1997). Exposing the immunology of naked DNA vaccines. *Immunity* 3;165–169.

Pfeffer, M., Proebster, B., Kinney, R. M. & Kaaden, O-R. (1997). Genus-specific detection of alphaviruses by a semi-nested reverse transcription reaction. *American Journal of tropical Medicine and Hygiene* 57, 709–718.

Pfeffer, M., Kinney, R. M. & Kaaden, O-R. (1998). The alphavirus 3'-nontranslated region: Size heterogeneity and arrangement of repeated sequence elements. *Virology* 240, 100–108.

Prayaga, S. K., Fuller, D. H., Haynes, J. R. & Murphey-Corb, M. (1995). Particle-mediated nucleic acid immunization. *Vaccines* 95, 105–109.

Reisen, W. K. & Monath, T. P. (1988). Western equine encephalomyelitis, pp. 89–137. *In The Arboviruses: Epidemiology and Ecology, Vol. V*. Edited by T. P. Monath. CRC Press: Boca Raton, Fla.

Robinson, H. L., Feltquate, D. M., Morin, M. J., Haynes, J. R., Webster, R. G. (1995). DNA vaccines: A new approach to immunization. *Vaccine* 95:69–75.

Sambrook, J., Fritsch, E. F., & Maniatis, T. (1989). *Molecular Cloning, a Laboratory Manual*, 2nd edn. Cold Spring Harbor: Cold Spring Harbor Laboratory.

Schlesinger, S. & Schlesinger, M. J. (1996). Togaviridae: The viruses and their replication, In *Fields Virology*, 3rd edn, pp. 825–841. Edited by B. N. Fields, et al. New York: Raven Press.

Strauss, J. H., & Strauss, E. G. (1988). Evolution of RNA viruses. *Annual Review of Microbiology* 42, 657–683.

Strauss, J. H., & Strauss, E. G. (1994). The alphaviruses: gene expression, replication, and evolution. *Microbiological Review* 58, 491–562.

Strauss, E. G., Rice, C. M. & Strauss, J. H. (1983). Sequence coding for the alphavirus nonstructural proteins is interrupted by an opal termination codon. *Proceedings of the National Academy of Science USA* 80, 5271–5275.

Strauss, E. G., Rice, C. M. & Strauss, J. H. (1984). Complete nucleotide sequence of the genomic RNA of Sindbis virus. *Virology* 133, 92–110.

Trent, D. W., & Grant, J. A. (1980). A comparison of new world alphaviruses in the western equine encephalomyelitis complex by immunochemical and oligonucleotide fingerprint techniques. *Journal or General Virology* 47:261–282.

Weaver, S. C., Hagenbaugh, A., Bellew, L. A., Netesov, S. V., Volchokov, V. I., Chang, G.-J J., Clarke, D. K., Gousset, L., Scott, T. W., Trent, D. W. & Holland, J. J. (1993). A comparison of the nucleotide sequences of eastern and western equine encephalomyelitis viruses with those of other alphaviruses and related RNA viruses. *Virology* 197, 375–390.

Weaver, S. C., Kang, W, Shirako, Y., Rumenapf, T., Strauss, E. G. & Strauss, J. H. (1997) Recombinational history and molecular evolution of western equine encephalomyelitis complex alphaviruses. *Journal of Virology* 71, 613–623.

Wolff, J. A., Malone, R. W., Williams, P., Chong, W., Acsasi, G., Jani, A., Felgner, P. L. (1990). Direct gene transfer into mouse muscle in vivo. *Science* 247, 1465–1468.

The alphaviruses are a group of about 27 enveloped viruses with a positive sense, nonsegmented single-stranded RNA genome (Calisher et al., 1980; Strauss and Strauss, 1988). The alphavirus disclosed in this invention, western equine encephalitis virus (WEE), is a member of the WEE antigenic complex and is serologically related to the Sindbis (SIN), Highlands J (HJ), Fort Morgan, Buggy Creek, and Aura viruses (Calisher & Karabatsos, 1988; Calisher et al., 1988). WEE is endemic in western North America and strains/varieties have been isolated from Argentina (AG80-646), Brazil (BeAr 102091) and the former Soviet Union (Y62-33) (Johnson and Peters, 1996; Weaver et al., 1997). In nature, WEE is transmitted from its amplifying hosts or reservoir in wild birds, to man and horses, by mosquitoes (*Culex tarsalis* being the principal vector). While the endemic cycle has resulted in only a limited number of human infections in recent years, in the past, major epidemics of WEE have been recorded. The most extensive epidemic, including 3,336 recognized human cases and 300,000 cases of encephalitis in horses and mules, occurred in the western United States and Canada in 1941 (Reisen & Monath, 1988; Johnson and Peters, 1996).

All alphaviruses share a number of structural, sequence, and functional similarities, including a genome with two polyprotein gene clusters (reviewed in Strauss & Strauss, 1994; Schlesinger & Schlesinger 1996). The genomic organization of these viruses is conserved (see FIG. 1), with the nonstructural proteins translated directly from the 5' two-thirds of the genomic RNA. A subgenomic positive-stranded RNA (the 26S RNA), is identical to the 3' one-third of the genomic RNA and serves as the translational template for the structural proteins (capsid, E3, E2, 6K and E1).

The nonstructural proteins (nsP1, nsP2, nsP3 and nsP4) are also synthesized as a polyprotein and processed into the four nsPs by a nsP2 protease. Two versions of the nonstructural polyprotein are synthesized in alphavirus-infected cells, due to frequent readthrough of an opal codon between the nsP3 and nsP4 genes in several alphaviruses (Strauss et al., 1983). The nsPs function in a complex with host factors to replicate the genome and transcribe the subgenomic mRNA. Alphaviruses have characteristic conserved sequences at the extreme 5' and 3' domains and the intergenic region (Ou et al., 1982, 1983; Pfeffer et al., 1998). These conserved domains are required for viral growth and replication and are believed to be important in promotion of protein synthesis and the initiation of RNA-dependent RNA polymerase activity.

The relationship of different WEE isolates to each other has been demonstrated using neutralization tests (Calisher et al., 1988). Additionally, several strains of WEE were typed by oligonucleotide fingerprinting, and found to have greater than 90% nt homology (Trent & Grant, 1980). The N-terminal sequences of the nucleocapsid, and the E1 and E2 glycoproteins have been determined by Edman degradation, and the E1 and E2 proteins were found to have 82% and 71% homology, respectively, to SIN (Bell et al., 1983). Hahn et al. (1988) sequenced the 26S region of WEE strain BFS1703. They proposed that WEE originated as a hybrid virus, formed by recombination of an EEE and a Sindbis-like virus, most likely during a co-infection event. They suggested that two crossover events occurred, one within the E3 gene, the other within the 3' nontranslated terminal region (NTR), resulting in a virus whose nonstructural domain, intragenic region, and capsid protein are similar to EEE, with envelope proteins showing homology to SIN.

Weaver et al. (1993) sequenced part of the nonstructural domain (nsP2 and nsP3 genes) of strain 5614, demonstrating this area also shows homology to EEE. Short regions within the nsP4 gene and the E1 protein/3' NTR have been determined for many WEE strains, allowing a preliminary assessment of the nucleic acid phylogenetic relationships within the WEE antigenic complex (Weaver et al., 1997). Serological studies (Calisher et al., 1988) and preliminary sequence determination (Cilnis et al., 1996; Weaver et al., 1997) of the HJ genome suggests this is another closely related virus, and most likely a descendant of the same recombinant viral ancestor as modem WEE.

A highly conserved region of the alphavirus nsP1 gene has been identified, and proved suitable for use in a polymerase chain reaction (PCR)-based genetic assay for alphaviruses, including WEE (Pfeffer et al., 1997). Phylogenetic analysis of this PCR fragment yielded similar results to those obtained by Weaver et al., (1997) for a PCR fragment in the nsP4 gene.

In terms of therapy or prophylaxis, there are very limited possibilities. An inactivated vaccine to WEE is under investigational new drug (IND) status. The vaccine uses formalin-inactivation of cell culture supernatants from WEE-infected tissue culture. It requires a minimum of 3 doses, yearly monitoring of antibody titer and possible boosters. Its effectiveness in the protection against an aerosol challenge of WEE has yet to be established. A WEE live attenuated vaccine based on an infectious clone is under development (J. Smith, personnel communication). The area of DNA immunization is relatively new, and has been reviewed in Hassett and Whitton, 1996; Donnelly et al, 1997. Similar to live, attenuated vaccines, DNA vaccines are known to stimulate both humoral and cellular immune responses (Pardoll and Backering, 1997; McCuskie and Davies, 1999). Much of the focus has been on methods to deliver and efficiently express the cloned products. Intramuscular administration of DNA has been one of the original methods used (Wolff et al, 1990). A second method uses ballistic delivery of DNA coated gold particles, using high pressure helium gas to propel the particles into the epidermis and dermis of animals (Prayaga et al, 1995, reviewed by Robinson et al, 1995).

The Applicant identified a number of related areas of research, including the development of subunit vaccines to WEE. In the present invention, the Applicant disclosed the cloning, sequencing and expression of the structural genes of a WEE virus (strain 71V-1658), as described in Netolitzky et al., (2000) "Complete genomic RNA sequence of western equine encephalitis virus and expression of the structural genes." *Journal of General Virology* 81, 151–159, which is herein incorporated by reference. The DNA construct (pCXH-3), and a second construct (pVHX-6) were used in DNA immunization studies in a mouse model for protection against intranasal administered WEE.

SUMMARY OF THE INVENTION

The present invention is directed to the development of a DNA-subunit vaccine to the WEE virus and its use against such virus. More specifically, DNA to structural components of the WEE virus are expressed and used as the subunit vaccine.

The present invention provides for the complete nucleotide sequence of WEE strain 71V-1658. Two novel cDNA clones, pCXH-3 and pVHX-6 are also disclosed as effective vectors for gene expression.

The present invention also provides the complete nucleotide sequence for the structural gene pcDWXH-7.

It further provides for a process for preparing a recombinant DNA vaccine against WEE virus, comprising cloning and sequencing of 26S region of a WEE virus strain 71V-1658 under conditions suitable to effect in vitro transcription and translation of the functional recombinant DNA expression vector pCXH-3 and pVHX-6.

BRIEF DESCRIPTION OF THE DRAWINGS

FIG. 2. Multiple sequence alignment.

FIG. 3. Stem loop structures in the 5' NTR.

FIG. 4. Stem loop structures in the 3' NTR.

FIG. 5. Phylogenetic relationship of the WEE nonstructural region compared to other alphaviruses.

FIG. 6. Expression of WEE structural genes in cell culture. One µg of plasmid DNA was transfected into Vero cells. After 31 hrs incubation, the cells were histochemically stained using a monoclonal antibody to WEE (11D2) .a.pCXH-3; b. pCI (control plasmid).

FIG. 7. In vitro transcription and translation of WEE expression vectors. Qiagen purified vectors containing the WEE 26S insert were expressed in vitro using the TNT system and [$^{35}$S]-methionine labelling. Three µL aliquots of each samples were run by SDS-PAGE on a 12% gel. Lane: 1) Rainbow $^{14}$C-labelled marker; 2) Luciferase translation control; 3) pVAX; 4) pVHX-6; 5) pCXH-3; 6) pcDWXH-7; 7) pcDWHX-45; 8) pXTR2-4.

FIG. 8. WEE mouse infectivity model. Groups of 4 mice were inoculated intranasally with 50 µL of virus (approximately $10^4$ PFU). The mice were monitored for 12 days, and the % survival graphed.

FIG. 9. Protection using ballistic delivery of pCXH-3. Groups of 4 mice were immunized with one or two doses (2×1.25 µg) of either pCI or pCXH-3. The interval between boosters (2 doses) or challenge was 3 weeks. The mice were challenged intranasally with 50 µL of WEE Fleming (1.25× $10^4$ PFU). The mice were monitored for 12 days. and the % survival graphed.

FIG. 10. Protection using ballistic delivery of pVHX-6. Groups of 4 mice were immunized with four doses (2×1.25 µg) of pVAX or pVXH-6. The interval between boosters or challenge was 2 weeks. The mice were challenged intranasally with 50 µL of WEE Fleming (1.25×$10^4$ PFU). The mice were monitored for 14 days, and the % survival graphed.

FIG. 11. Protection using ballistic delivery of pVHX-6. Groups of 5–8 mice were immunized with three or four doses (2×1.25 µg) of pVAX or pVXH-6. The interval between boosters or challenge was 2 weeks. The mice were challenged intranasally with 50 µL of WEE Fleming (1.7× $10^4$ PFU). Untreated control and WEE inactivated control (3 doses) groups were also included. The mice were monitored for 14 days, and the % survival graphed.

DETAILED DESCRIPTION OF THE INVENTION

Figure 1:
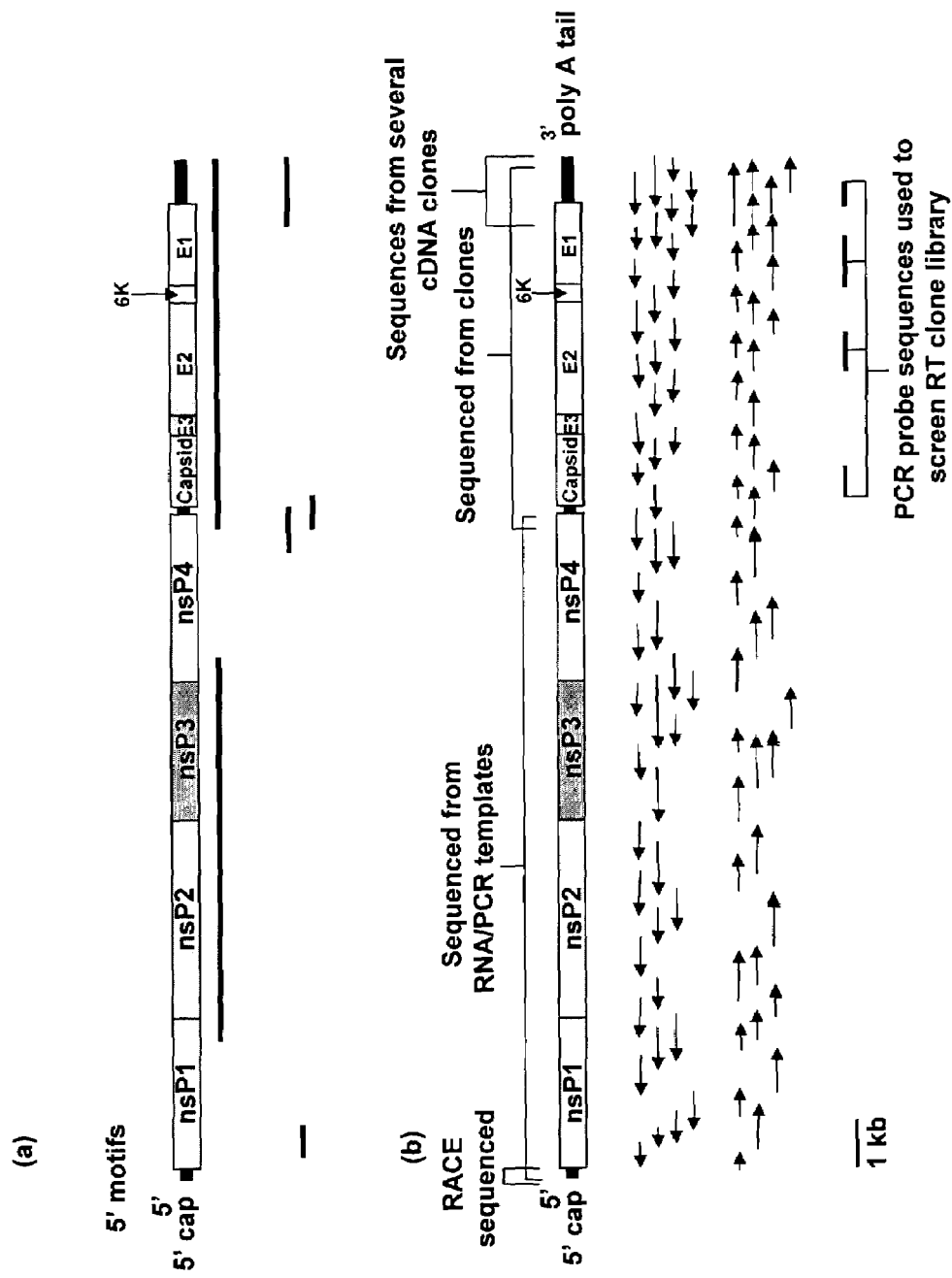
FIG. 1. Diagram showing the WEE 71V-1658 sequencing strategy. The location of PCR probe sequences used to screen the WEE cDNA library are also indicated, along with the genomic organization of the virus.

The complete nucleotide sequence of the 71V-1658 strain of western equine encephalitis (WEE) virus was determined (minus twenty-five nucleotides from the 5' end) and shown in SEQ ID NO: 1. A 5' RACE reaction was used to sequence the 5' terminus from WEE strain CBA87. The deduced WEE genome was 11,508 nucleotides in length, excluding the 5' cap nucleotide and 3' poly(A) tail. The nucleotide composition was 28% A, 25% C, 25% G and 22% U residues. Comparison with partial WEE sequences of strain 5614 (nsP2-nsP3 of the nonstructural region) and strain BFS 1703 (26S structural region) revealed comparatively little variation; a total of 149 nucleotide differences in 8624 bases (1.7% divergence), of which only 28% of these changes (42 nucleotides) altered the encoded amino acids. Comparison of deduced nsP1 and nsP4 amino acid sequences from WEE with the corresponding proteins from eastern equine encephalitis (EEE) yielded identities of 84.9% and 83.8%, respectively. Previously uncharacterized stem loop structures were identified in the nontranslated terminal regions.

A 3100 bp clone was identified (pcDNA-12) from the 3' end of the structural genes. A 1500 bp fragment was PCR amplified and cloned into the 5' end of pcDNA-12 to produce a complete clone of the structural genes (XH-7) as shown in SEQ ID NO: 2. A cDNA clone (pCXH-3) in which the structural genes of WEE strain 71V-1658 were placed under the control of a cytomegalovirus promoter was made, and transfected into tissue culture cells. The viral envelope proteins were functionally expressed in tissue culture, as determined by histochemical staining with monoclonal antibodies which recognize WEE antigens. The construct was used to immunize mice ballistically and intramuscularly. Mice protected ballistically had a significantly reduced risk of infection, against a subsequent intranasal challenge with WEE virus. A new vector was constructed to determine if increased levels of expression could be obtained. The construct used a pVAX vector to express the WEE structural genes (pVHX-6). Upstream portion of the pVHX-6 vector to where it becomes the XH-7 sequence is shown as SEQ ID NO: 3. The remaining nucleotide sequence of pVHX-6 from the point of divergence is identical to that of structural gene pcDWXH-7 of SEQ ID NO: 2.

Materials and Methods

Virus Culture and Purification

Tissue culture was maintained in accordance with established methods (Bird & Forrester, 1981). Minimal essential media containing 5% fetal calf serum (5% DMEM) was used to grow Vero (CRL 1586) and Chinese hamster ovary (CHO) K1 (CCL 61) cells obtained from American Type Cult re Collections. A 10% suckling mouse brain (SMB) suspension of WEE strain 71V-1658 was kindly provided by Dr. Nick Karabatsos, Centers for Disease Control, Fort Collins, Colo. WEE Fleming and California strains were purchased from ATCC (Mannanas, Va.). WEE B11 and CBA87 strains were kindly provided by Dr. George Ludwig, United States Army Medical Research Institute of Infectious Disease (Frederick, Md.). Seed stocks of WEE strains were made by inoculation of Vero cells with virus suspensions at a multiplicity of infection (MOI) of less than 0.1. For RNA isolation, virus stocks were prepared by infecting Vero cells at a MOI of 10. The virus was precipitated from cleared supernatant by the addition of polyethylene glycol MW 6000 to 7% (w/v) and NaCl to 2.3% (w/v). It was subsequently purified on a 20–60% (w/w) continuous sucrose gradient, followed by resuspension in PBS.

Nucleic Acid Preparation

Viral RNA used in WEE strain 71V-1658 library construction was prepared by the lysis of virus in 0.5% (w/v) sodium dodecyl sulfate (SDS), and RNA extracted using the cesium chloride/guanidium isothiocyanate method previously described (Sambrook et al., 1989). RNA was precipitated using sodium acetate and ethanol, then stored at −70° C. Prior to use, RNA was washed with 80% (v/v) ethanol, dried and dissolved in nuclease-free water (Promega, Madison, Wis.). Integrity of the RNA was checked on formaldehyde agarose gels (Sambrook et al., 1989). A cDNA library of WEE strain 71V-1658 was made by Invitrogen (San Diego, Calif.), by the ligation of cDNA into the BstXI site of prepared pcDNAII vector, and electroporation into electrocompetent DH1 F' *Escherichia coli* cells. Manipulation of RNA and DNA followed established procedures (Sambrook et al., 1989; Ausubel et al., 1995). Rapid plasmid preparations were made using the Wizard™ plasmid purification kit (Promega, Madison, Wis.). Large-scale plasmid preparations used the alkali lysis protocol as modified by Qiagen (Chatsworth, Calif.). For PCR, RT-PCR and DNA sequencing, oligonucleotide primer design was guided by information from WEE strain BFS1703 and other partially sequenced WEE strains (Hahn et al., 1988; Weaver et al., 1993), and from regions of sequence conservation (Ou et al., 1982 & 1983). Oligonicleotides were synthesized and gel purified either at the Regional DNA Synthesis Laboratory (Calgary, Alberta), or on a Beckman Oligo 1000 DNA synthesizer. A catalog with the sequences of primers used is listed in Table 1.

Construction of pCXH-3

The Invitrogen WEE library was screened by dot blot hybridization (Sambrook et al., 1989) with [$^{32}$P]-labeled, random primed RT-PCR fragments as probes (Amersham, Oakville, ON). A 3100 bp insert, pcDW-12, was identified, and corresponded to the 3' end of the 26 S RNA. The missing 5' end of the 26S region was generated by RT-PCR using the primers WEE5'SstI and WEEP3 (Table 1). The 1500 bp SstI/NcoI restricted fragment was inserted into the plasmid, phT3T7BM+ (Boehringer Mannheim, Laval, PQ), to generate a XbaI site on the 5' end. The 1500 bp XbaI/NcoI fragment was excised, gel purified and inserted into the XbaI and NcoI restriction sites of pcDW-12. The resulting clone, pcDWXH-7, encoded the complete 26S region of WEE 71V-1658. The structural gene insert from pcDWXH-7 was cloned into the mammalian expression vector, pCI (Promega, Madison, Wis.). The pcDWXH-7 plasmid was first linearized using HindIII, followed by a Klenow fragment reaction to fill in the 5' overhang. The insert was then excised using XbaI, gel purified and ligated into the XbaI/SmaI digested pCI vector. The isolated recombinant plasmid, pCXH-3, was characterized as having the correct insert by restriction mapping.

Construction of pVHX-6

The clone, pcDWXH-7, encoded the complete 26S region of WEE 71V-1658 was digested with Sac I, and religated in the reverse orientation. The isolate, pcDWHX-45, contained the complete 26S of WEE, with the reverse cloning sites (HindIII on the 5' end and XbaI on the 3' end). The WEE 26S gene segment was excised from pcDWHX-45, and cloned into the HindIII and XbaI sites of the mammalian expression vector, pVAX (Invitrogen, La Jolla, Calif.). After transformation into *E. coli* DH10α (Life Sciences, Burlington, ON) and screening of inserts by restriction analysis, a resulting isolate, pVHX-6 was identified. SEQ ID NO: 3 shows the upstream portion of the pVHX-6 vector to where it becomes the XH-7 sequence. The remaining nucleotide sequence of pVHX-6 from the point of divergence is identical to that of structural gene pcDWXH-7 of SEQ ID NO: 2.

Expression of the Structural Genes of WEE

The pCXH-3 expression vector was transfected into Vero or CHO K1 cells using the cationic lipid, Lipofectamine™ (Gibco/BRL, Burlington, ON). Briefly, Vero or CHO K1 cells were grown to 30–50% confluency in Costar 6-well plates. The monolayers were transfected with pCXH-3 in accordance with the manufacturer's directions, for a period of 5 hrs, followed by a further 29 hr incubation after the addition of 5% DMEM. The monolayers were fixed in methanol:acetone (1:1) for 5 min and washed with PBS containing 0.1% (v/v) Tween 20 and 3% BSA (PBS-TB). The cells were incubated 45 min at 37° C. with a 1/100 dilution (in PBS-TB) of concentrated cell supernatant from hybridoma cell lines expressing monoclonal antibodies to the WEE E1 (clone 11D2) or E2 (clone 3F3) proteins, followed by washing with PBS-TB. Monolayers were incubated with a 1/4000 dilution of goat anti-mouse IgG/IgM (H & L) horse radish peroxidase conjugate (Caltag, So. San Francisco, Calif.) for 45 min at 37° C. After washing with PBS-T, 2 mL of TruBlue™ HRP substrate (Kirkegaard & Peny Laboratories, Gaithersburg, Md.) was added, and plates were incubated a further 30 min at room temperature, followed by microscopic examination.

In a second method, one-step in vitro transcription and translation reactions using the TNT coupled system (Promega Corporation, Madison, Wis.) was used to express the gene products from both pCXH-3 and pVHX-6, as both have an upstream T7 promoter which can be used for in vitro expression of inserts. The RNA was translated in the presence of [$^{35}$S]methionine to produce radiolabeled WEE proteins, which were further processed with canine pancreatic microsomal membranes. All components of the in vitro transcription and translation reactions were incubated together for 90 min at 30° C. Results were analyzed by SDS-PAGE or radioimmunoprecipitation.

Radioimmunoprecipitation

The TNT reactions were diluted to a volume of 500 ml with RIP buffer consisting of 0.15 M sodium chloride, 0.1% SDS, 50 mM Tris-HCl pH 7.4, and 1% Triton X-100. They were then preabsorbed by incubating with 75 L of protein G-agarose (Gibco BRL) for 30 min at room temperature. The samples were centrifuged at 13,000 rpm for 1 min, and the supernatants were then immunoprecipitated with either 100 μL of supernatants from anti-WEE hybridoma cells or 20 μg of purified anti-WEE antibodies. The reactions were incubated for 1.5 hr at room temperature, after which 75 μL of protein G-agarose was added. The reactions were incubated for an additional 30 min at room temperature. Immunoprecipitated proteins were collected by centrifuging at 13,000 rpm for 1 min. The pellets were washed with 500 μL of RIP buffer and centrifuged at 13,000 rpm for 1 min; this step was repeated three additional times. The pellets were resuspended in 2× Laemmli sample buffer (Bio-Rad Laboratories) containing fresh 2% b-mercaptoethanol and heated at 100° C. for 10 min. The samples were centrifuged at 13,000 rpm for 1 min, and the supernatants were collected. The immunoprecipitated [$^{35}$S]labeled WEE proteins were further analyzed by SDS-PAGE and autoradiography.

Radiolabelled [$^{14}$C]molecular weight markers from Amersham Pharmacia Biotech were also run on the polyacrylamide gels.

DNA Sequencing

Automated sequencing of the 26S region was performed using the ABI Prism Dye Terminator Cycle Sequencing or Big-Dye.TM. Terminator Cycle Sequencing kits of plasmid templates according to the manufacturer's instructions (PE-Applied Biosystems, Foster City, Calif.). Sequencing reactions were purified on Centri-Sep.TM. columns (Princeton Separations, Adelphia, N.J.), dried and analyzed on an ABI 373 or 310 automated sequencer. For the nonstructural region, template cDNAs were generated in a single-step integrated RT-PCR procedure using the Titan.TM. RT-PCR kit (Boehringer Mannheim, Laval, PQ), following the manufacturer's suggested protocols. RT-PCR products were purified using the QIAquick.TM. PCR Purification kit (Qiagen, Chatsworth, Calif.) and sequenced (50–100 ng DNA per reaction). The extreme 5' end of the genome was not sequenced in WEE 71V-1658. However, a 5' RACE reaction (Frohman et al., 1988) was used to obtain a cDNA fragment from the 5' terminus of WEE strain CBA87. Briefly, primer WEE559 (GGTAGATTGATGTCGGTGCATGG-SEQ ID NO. 8) was used to prime reverse transcription of the 5' terminus of the viral RNA. After poly(A) tailing of the cDNA with terminal transferase, a plus sense primer (GTACTTGACTGACTGTTTTTTTTTTTTTT-SEQ ID NO. 9) was used in conjunction with WEE559 for amplification of the 5' terminus.

Nucleotide Sequence Analysis and Assembly

Sequence traces were edited manually and assembled using the Seqman component of the Lasergene DNA analysis software (DNASTAR, Madison, Wis.). Codon preferences and patterns were assessed using the CodonUse and CodonFrequency programs, while the overall frequency of mononucleotide and dinucleotides was calculated using the Composition program (Wisconsin Package, Version 9.0, Genetics Computer Group, Madison, Wis.). Quantitative assessments of sequence similarities (nucleotide and amino acid), were calculated by preliminary alignment using the Pileup program, followed by manual alignment adjustment, and analysis with the Distances program (GCG). Amino acid sequences aligned as described, were used as the basis for generating phylogenetic trees (GCG). The GeneQuest module of the Lasergene program (DNASTAR, Madison, Wis.) was used to predict and calculate RNA secondary structures at the ends of the genomic RNA using minimal energy calculations. Multiple sequence alignments were accomplished using the Clustal component of MegAlign (DNASTAR). The complete WEE genomic nucleotide sequence has been submitted to GenBank (Accession Number AF143811).

Administration of DNA or Inactivated Virus

DNA solutions or an inactivated WEE virus vaccine in PBS, were administered to the mice by ballistic or intramuscular (IM) routes. For IM route of administration, a 27 g needle was used to deliver 50 µg of DNA (pCXH-3 or pCI-negative control) or 50 µL of inactivated WEE vaccine (SALK WEE inactivated vaccine). The volume of inoculum used was 100 µL, diluted in PBS. Fifty µL was administered IM to each of the hind leg muscles of a mouse. When boosters were given, they were administered 14–28 days apart. For ballistic administration, mice were shaved in the abdominal area with electric hair clippers. The mouse was subjected to ballistic delivery of DNA coated onto gold particles following the manufacturer's standard specifications. The Helios Gene Gun (Biorad, Mississauga, ON) was used as directed, at a pressure setting of 400 psi. Mice were given 1.25 µg DNA and 0.5 mg gold, 1 µm diameter, per shot, and up to three shots for one dose time. Boosters were given 14–28 days apart. The mice were challenged 14–28 days after the final booster.

Mouse Infectivity with WEE

Female BALB/c mice, 17–25 g, were obtained from the mouse breeding colony at Defence Research Establishment Suffield (DRES), with the original breeding pairs purchased from Charles River Canada (St. Constant, Quebec, Canada). The use of these animals was reviewed and approved by Animal Care Committee at DRES. Care and handling of the mice followed guidelines set out by the Canadian Council on Animal Care. Virus was administered to the mice by intranasal (N) or intraperitoneal (IP) routes. The volumes of inoculum used were 50 µL for IN and 100 µL for IP. For IN administration, mice were anaesthetized with sodium pentobarbital (50 mg/kg body weight, intraperitoneal). When the animals were unconscious, they were carefully supported by hands with their nose up, and the virus suspension in PBS was gently applied with a micropipette into the nostrils. The applied volume was naturally inhaled into the lungs. For IP infection, the mouse was manually restrained, and a 1 ml tuberculin syringe fitted with a 27 g needle was used to administer approximately 100 µL of the virus suspension in PBS. Infected animals were observed daily, for up to 14 days post infection.

Results

Complete Nucleotide Sequence of WEE Genome and Deduced Amino Acids

The nucleotide sequence of WEE strain 71V-1658 (SEQ ID NO: 1) was determined via several distinct sequencing strategies, as summarized in FIG. 1. The 5' terminus of 25 nt was not determined for this strain. However, it was determined by sequencing a 5' RACE product from strain CBA87. Excluding the terminal 5' cap structure and the 3' poly(A) tail, the genomic sequence of WEE was found to be 11,508 bases long. The base composition was 28% A, 25% C, 25% G, and 22% U. The dinucleotide usage of the WEE genome was compared with those values anticipated from the base composition. Several dinucleotides were found in lower proportions than anticipated, notably UpA (81%), CpG (83%) and CpC (85%) (data not shown). Codons containing the CpG dinucleotide were present at 82% of the anticipated value, including codons for serine (78%), proline (80%) and arginine (78%).

The WEE 71V-1658 sequence was used to conduct a variety of phylogenetic analyses with previously determined alphavirus sequences. The alphaviruses used in the analyses included EEE strain North American variant (Genbank Acc. No. X67111), O'Nyong Nyong (ONN) strain Gulu (Genbank Acc. No. M33999), Ross River (RR) strain NB5092 (Genbank Acc. No. M20162), Semliki Forest (SFV) (Genbank Acc. No. J02361), SIN strain HR (Genbank Acc. No. J02363) and VEE ID (Genbank Acc. No. L04653). The degree of conservation among the various sequences (nucleotide and amino acid) through the stereotypical alphavirus genome is shown in Table 2. The carboxy-terminal domain of nsP3, which consistently fails to exhibit homology among sequenced alphaviruses, was excluded from this comparison as it has been adjusted for in previous analysis (Weaver et al., 1993). The deduced amino acid sequences for nsP1–4 of WEE 71V-1658 demonstrated closest identity to the corresponding proteins from EEE (Table 1), reflecting similar observations made for nsP2 and nsP3 of WEE 5614 and EEE (Weaver et al., 1993).

Nontranslated Terminal Regions

Alignment of the 5' terminal nucleotide sequences of WEE CBA87 and WEE 71V-1658 is shown in FIG. 2a, along with a comparison of the 5' termili from EEE and VEE. The close similarity between WEE and EEE, has been verified experimentally, in that a EEE/Highlands J degenerate primer, EHJ5', was able to PCR amplify the 5' end of the WEE genome, while an analogous SIN primer could not (data not shown).

Potential stem loop structures were found in WEE 71V-1658, including a stem loop at the extreme 5' terminus (2–30) and a pair of stem loops (137–189) (FIG. 3a). The homologous structures for EEE are also shown (FIG. 3b) (Ou et al., 1983). Minimal energy values calculated for the stem loops were similar between WEE and EEE. Further analysis of the region between the structures described above, indicated a large, highly base-paired stem loop structure (39–131), that had not been previously described, and was observed in SIN and EEE in a similar location (data not shown).

The sequence of WEE 71V-1658 3' NTR, overall, shared little homology with any of the alphaviruses examined, but included the highly conserved 19 nt region at the 3' end (11490–11508), which was identical to that determined for WEE BFS1703 by Hahn et al., 1988. Two copies of the characteristic 40 base Sindbis-like terminal repeats as previously reported (Ou et al., 1982) were found in WEE 71V-1658 (11234–11273 and 11292–11331). However, the 3' NTR of WEE showed some surprising results that had not been previously described. The first 40 nt terminal repeat formed the backbone for the formation of a 57 nt double stem loop structure (11228–11284) (FIG. 4b), consisting of an α and β loop. The second 40 nt repeat of WEE formed a nearly identical 59 nt double stem loop structure (11285–11343), directly adjacent to the first structure. SIN with three 40 nt repeats, forms three double stem loops (FIG. 4a) while EEE, which does not contain a SIN-like 40 nt repeat, contains the α and β loops (FIG. 4c).

Nonstructural Region

Comparisons within the nonstructural regions (4475 nt) of WEE strains 71V-1658 and 5614 (Weaver et al., 1993), yielded 94 nt changes resulting in 26 amino acid substitutions (1.8% difference) as summarized in Table 2. The most notable variation, a three-base deletion (4530) within the nsP3 gene of WEE 71V-1658 constitutes the only insertion/deletion observed within the polypeptide encoding regions. A short hypervariable region was observed (1421–1449), where 11 of 28 nt were different between the two WEE strains (FIG. 2b). The presence of an opal termination codon and partial read-through site at the junction of nsP3 and nsP4 is consistent with WEE 5614. Extending previous phylogenetic analyses of WEE (Weaver et al., 1993, 1997), phylogenetic trees depicting viral relatedness were constructed with the Distances program (GCG), for the unexamined genes (nsP1, nsP4) and the entire nonstructural polypeptide encoding region (FIG. 5). The data reveals the close relationship of WEE to EEE, relative to the other alphaviruses analyzed.

Structural Genes

The largest WEE cDNA clone isolated, pcDW-12, was 3100 bp in size, but missing 5 nt and the poly(A) tract from the 3' end as determined by restriction mapping and DNS sequence analysis. The missing 5' 1500 bp fragment was synthesized using PCR (primers WEE5'Sst1 and WEEP3) and subsequently cloned into pcDW-12 to yield a full-length clone of the structural genes (pcDWXH-7) (SEQ ID NO: 2). Comparison of the structural region of WEE 71V-1658 with WEE BFS1703 (Hahn et al., 1988), indicated 53 nt changes, resulting in only 11 amino acid differences, of which two were nonconserved. One difference in residue was observed from the amino acid sequence of the N-terminus of the E2 protein of the WEE MacMillan strain (Bell et al., 1983), when this was compared to the deduced protein sequence of 71V-1658. A short fragment (802 nucleotides) of the WEE 71V-1658 E1 protein gene, and the 3' NTR had been published previously (Weaver et al., 1997); comparison with the sequence reported herein indicated no differences.

Expression of Structural Gene

Expression of the insert from the cytomegalovirus (CMV) promoter was accomplished by transfection of the pCXH-3 plasmid into either Vero or CHO K1 cells. Cells expressing the E1 or E2 proteins were detected through the use of specific E1 or E2 monoclonal antibodies to WEE, followed by histochemical staining with the HRP substrate, Tru-Blue as demonstrated in FIG. 6a. The control cells transfected with pCI alone showed no staining (FIG. 6b), thus, demonstrating the fidelity of the proteins translated from the cloned 26S region. In vitro translation of the insert using TNT T7 rabbit reticulysate and canine microsome system demonstrated synthesis of $^{35}$S-methionine-labelled proteins of the correct size as indicated by immunoprecipitation with monoclonal antibodies to the NC, E1 and E2 proteins (data not shown). Similarly, the construct pVHX-6 was along demonstrated to produce the correct MW proteins as determined by in vitro transcription/translation. The level of expression for pVHX-6 was significantly higher then for pCXH-3 (FIG. 7).

Protection Against WEE Infection Using DNA Immunization

Figure 8:
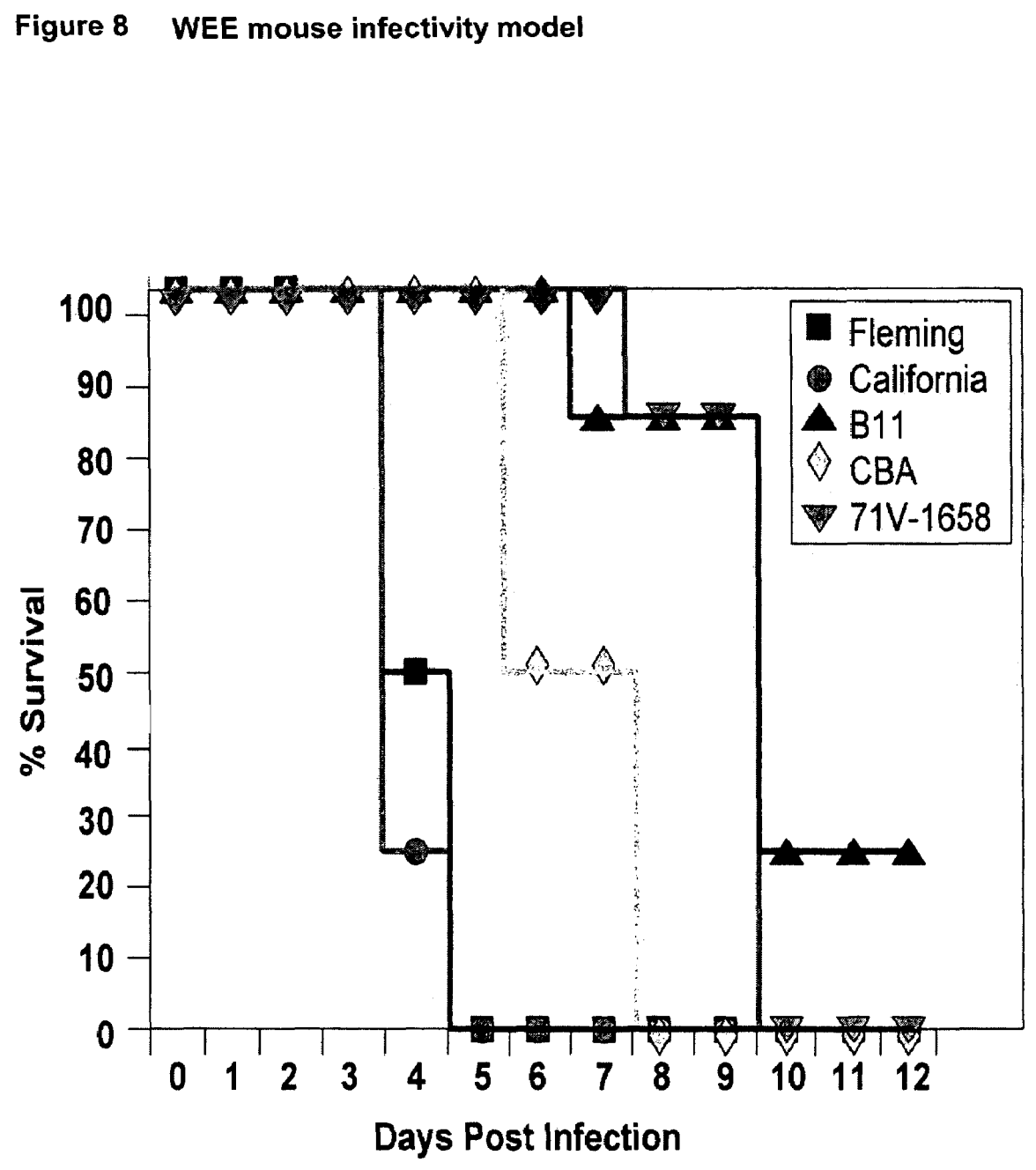

Different strains of WEE were shown vary in their virulence in BALB/c mice. When similar amounts of WEE were given intranasally to BALB/c mice, time to death varied from 4 to 8 days. The California and Fleming strains were the most virulent (FIG. 8), and the Fleming strain was chosen as the challenge strain in protection studies. IP administration of the virus did not kill adult mice (data not shown). Intramuscular administration of pCXH-3 did not show any protection, using one or two doses of 50 µg, followed by challenge 30 to 90 days after the final dose (data not shown). Intramuscular administration did result in an increase in antibody titre to WEE as determined by ELISA using a monoclonal antibody to the E1 protein of WEE (data not shown). Expression and protection of pCXH-3 DNA when delivered ballistically. pCI was used as a control DNA. When two doses of pCXH-3 was given, protection of 50% was demonstrated as compared to no protection for pCI (FIG. 9) or PBS controls (data not shown). IM injection showed marginal protection (one group 25% survival—data not shown). The dose of WEE Fleming strain (challenge strain) was 1.25×10$^4$ PFU for 100% killing via an intranasal route of infection. Preliminary studies examining protection using the pVHX-6 vector, indicated promise with this construct using the Gene Gun, and ballistic delivery. With the pVHX-6 vector, one mouse succumbed immediately to the effects of the sodium pentabarbital (anaesthetic). The remaining three mice showed no signs of coming down with a WEE infection, and remained completely heathy (FIG.

Figure 11:
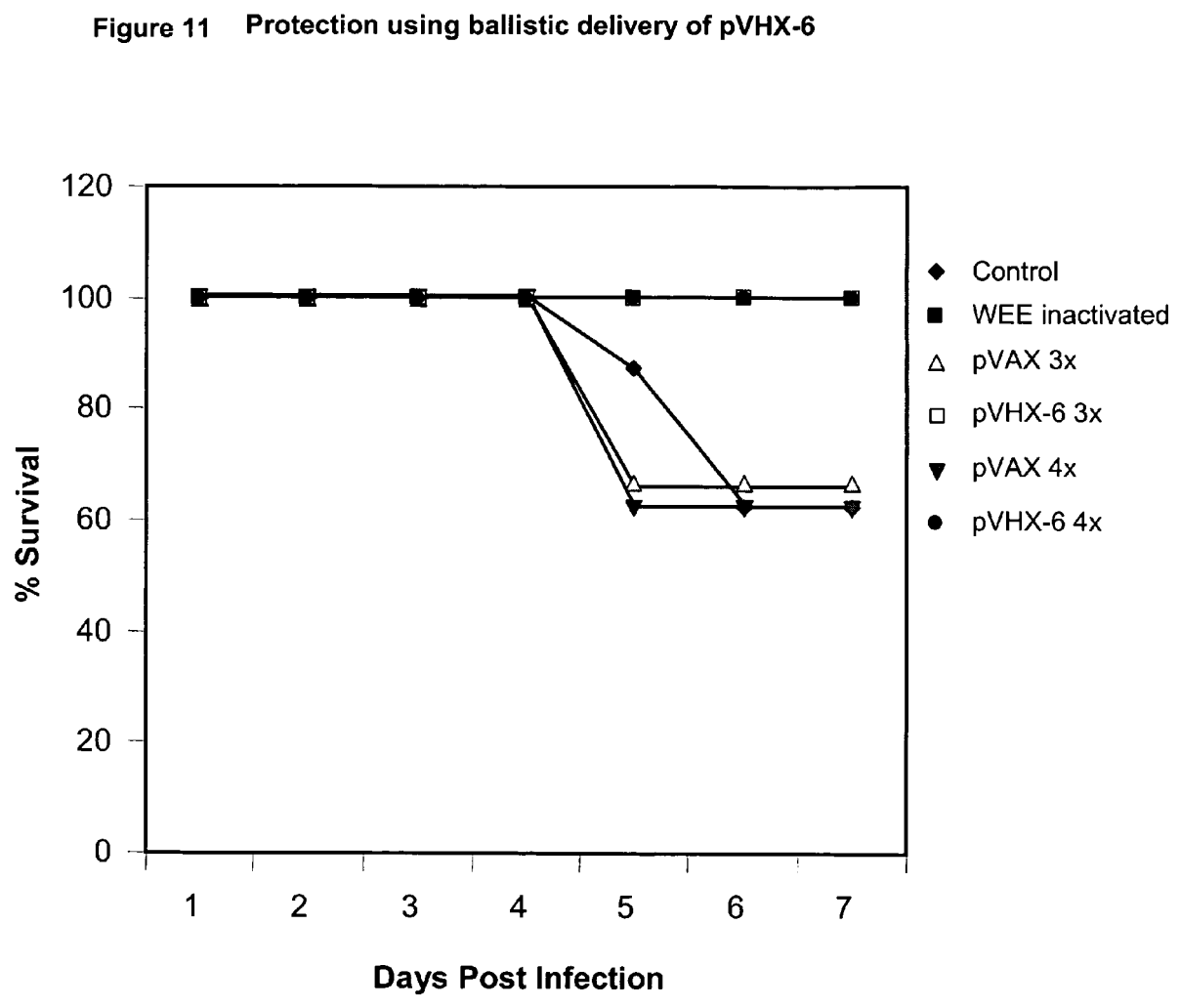

10). Of the four pVAX control mice, all showed signs on WEE infection, and two of the four mice died, while two did recover. A repeat of this experiment using 3 or 4 doses of pVHX-6, given 2 weeks apart, showed complete protection of the mice, similar to 3 doses of WEE inactivated vaccine (FIG. 11). Three or 4 doses of pVAX showed results similar to the saline control, with only about 60% of the mice surviving FIG. 11.

Discussion

The WEE 71V-1658 genomic sequence of 11,508 bases was determined directly from cDNA clones of WEE or via sequencing RT-PCR products. The first 25 bases of the WEE genome was determined indirectly, through the use of a 5' RACE reaction in WEE CBA87. Noting the relatively high conservation in the WEE sequences overall (1.7% divergence) and in the overlap region between the two WEE sequences (see FIG. 2a), it appears that the 5' ends of 71V-1658 and CBA87 are of similar size and sequence.

Comparison of WEE 71V-1658 to other partial sequences of WEE (Hain et al., 1988; Weaver et al., 1993) suggests little variation at the nucleotide level among these viruses (Table 2), showing an overall nt sequence difference of 1.7% over 8624 nt. Given a calculated rate of divergence of 0.028% per year for the WEE E1 protein (Weaver et al., 1997), the expected nt divergence for a difference in isolation of 18 years between the strains, should be 0.5% (71V-1658 isolated in 1971 and BFS 1703 in 1953). The E1 protein itself showed a rate of divergence of 1.5% in nt sequence between 71V-1658 and BFS1703. The lower rate observed by Weaver et al., (1997) could be due to greater conservation of structure at the C terminus of E1, from where the rates of divergence were calculated. Areas with high rates of divergence were observed between WEE strains 71V-1658 and 5614 at the 3' end of nsP1 and the 5'end of nsP4 (Table 2). The relatively high interstrain value for nsP1 (4.5% difference) may be due to the presence of a small hypervariable region, with 11 of 28 nt changed in strain 5614 (FIG. 2b). Variation in nsP4 occurred in a stretch of 21 nt at the 3' end of the 5614 sequence, and were left out of subsequent homology comparisons (similarity with the EEE sequence was maintained in this region). Discounting the carboxy-terminal region of nsP3 also gives a more accurate picture of the homology of the nsP1-4 nonstructural region (Weaver et al., 1993). The results for comparison of nt and protein sequences of WEE to other alphaviruses is shown in Table 2, and are similar to those obtained with nsP2 and nsP3 of 5614, when compared to other alphavirus sequences. Phylogenetic analysis of the WEE 71V-1658 deduced protein sequences of nsP1, nsP4 and the nsP1-4 region, as related to other alphaviruses (FIG. 5), illustrates the close relationship to EEE (HJ sequences were very limited for comparative purposes and were not included).

Assessments of codon usage frequencies and the frequency at which certain dinucleotides are found throughout the genome identified a number of statistical anomalies. The slight CpG dinucleotide deficiency previously described within other alphaviruses, and WEE itself, was confirmed in this study, at levels comparable to those reported (Weaver et al., 1993). The CpG under representation is a typical feature of vertebrate genomes, and is not seen in invertebrates. Viruses which infect dual hosts, such as the arboviruses, might be expected to utilize an intermediate nucleotide bias, as indicated by the slight CpG under-utilization observed in alphaviruses (Weaver et al., 1993). A pronounced under-representation of two other dinucleotides was also observed within the WEE genome, UpA, and CpC, a phenomenon noted throughout the genome, though the role of these codon preferences is unclear.

The 5' NTR sequence of WEE shows a close phylogenetic affiliation to EEE, and to HJ, although the HJ sequence information is more limited. Ou et al., (1983) had previously predicted (based on minimal free energy calculations) two hairpin structures at the 5' NTR of several alphaviruses including SIN and EEE. Both structures are present in WEE, the first of which is a 5' terminal hairpin structure (2–30), similar to that calculated for EEE (FIGS. 3a and b). The second is a dual hairpin structure (137–162, 165–189) which is almost identical to that identified for EEE. The region between the terminal and dual hairpins can itself form a long hairpin structure, and includes highly conserved stretches of 92 nt (data not shown). The significance of these structures is currently unknown.

Previous reports (Hahn et al., 1988; Pfeffer et al., 1998) suggested WEE virus arose as a result of two recombination events between alphavirus-like ancestral viruses. The first recombination occurred near the junction of the E3 and capsid genes. The second recombination occurred 80 nucleotides from the 3' end of the genome. Evidence for the occurrence of the second recombination event is inferred from sequence similarities of the 3' NTR between WEE, EEE and SIN, in which WEE shows greater similarity to EEE (65%) than to SIN (50%) in the last 100 nt of the 3' end. However, the apparent plasticity of the 3' NTR may only be reflecting the selective pressures under which the nascent WEE virus evolved, resulting in rapid selection of 3' sequences which are more similar to EEE, and may not represent an actual recombination event as previously postulated.

The 3' NTRs of alphaviruses are characterized by widespread sequence divergence and yet contain small, strongly conserved motifs (reviewed in Strauss & Strauss, 1994; Pfeffer et al., 1998). Analysis of the 3' NTR indicated the presence of double stem loop structures among SIN and WEE (FIGS. 4a and b). Interestingly, the 40 bp repeat found in SIN and WEE is contained within the double stem loop structure. SIN was found to contain 3 double stem loop structures and WEE was found to contain two. In SIN, the spacing between the three double stem loop structures was around 30 nucleotides, while in WEE the distance was zero nt separating the structures. Additional alphaviruses were assessed and it is interesting to note that double stem loop structures were found in many of the WEE- and SIN-related viruses (SIN, Aura, Babanki, Ockelbo, Kyzylagach, Whataroa, WEE and HJ). The double stem loop structures found in SIN and WEE viruses consisted of the α loop (AUGUA [U/C]U) and the β loop (GCAUAAU) (FIG. 4b). Surprisingly, while EEE does not have the 40 bp repeat element found in SIN and WEE, it contains the α and β loop structures (FIG. 4c). The significance of these conserved loop structures between SIN, WEE and EEE viruses has yet to be elucidated, although previous studies suggest a role in viral replication and/or host specificity (Kuhn et al., 1990; Kuhn et al., 1991). For example a deletion of 26–318 nt from 3' end of SIN, resulted in reduced viral replication in mosquito cells but not in chicken cells (Kuhn et al., 1990). In contrast, substitution of the SIN 3' NTR with the substantially different RR 3'NTR (which lacks the 40 bp repeat and double stem loop structures), had no effect on the growth of the chimeric virus in mosquito cells, suggesting that host proteins interact with the 3' NTRs to cause differential host effects (Kuhn et al., 1991).

The 26S region of 71V-1658 was placed under the control of the CMV promoter of pCI. To test for functional expression of the pCXH-3 vector and for a functional product in cell culture, the pCXH-3 vector was transiently transfected into Vero cells. WEE proteins were detected on the cell using specific monoclonal antibodies to both the E1 (FIG. 6a) and E2 proteins (data not shown). The binding specificity of these monoclonals has been previously determined by western blot analysis and immunoprecipitation analysis (data not shown). The use of pCXH-3 in DNA immunization experiments indicated that the construct could partially protect against WEE intranasal challenge using ballistic delivery. Preliminary results do indicate that WEE reactive antibodies can be detected by ELISA when the pCXH-3 plasmid is given intramuscularly (unpublished results). However, this afforded no protection to the mice, as there were no survivors. Intranasal (data not shown) delivery of the pCXH-3, with and without liposome encapsulation did not demonstrate any protection under the conditions used. Mice immunized with the pCI control plasmid did not show any signs of protection in these studies.

Expression of the WEE structural proteins in the pCI-based vector (pCHX-3) gave moderate to poor levels of expression in vitro, using the TNT expression kit. A new vector, pVAX (Invitrogen) was designed for DNA immunization and was basically the same as pCI, but lacked the intron found in the pCI vector. Initial restriction mapping of pCXH-3 indicated the plasmid was the expected size, but later analysis indicated a extra 4 kb fragment was present (data not shown). The WEE structural proteins were cloned and expressed in pVHX-6, indicating the correct sized proteins by SDS-PAGE, and producing higher levels of WEE product in vitro (FIG. 7). Preliminary results with pVHX-6 indicated it could completely protect mice against an intranasal challenge of WEE. While 50% of the pVAX mice did survive, they all demonstrated at least moderate to severe infection with WEE. It is possible that pVAX contains CpG motifs that show some protective effect, through a nonspecific adjuvant like effect (Kreig et al, 1998). However, there was a dramatic difference between the pVAX and the pVHX-6 group, in the protection afforded the two groups of mice.

The plasmids, pCXH-3 and pVHX-6 show promise as vaccine candidates for WEE. This is especially important for protection against an aerosol challenge of WEE, and event that would be envisioned in a potential biological warfare attack using WEE as a biological warfare agent. This agent is difficult to protect against if delivered aerosolly, as the agent is purported to travel up the nerves directly into the brain. The research is applicable to VEE and EEE, as these viruses can also cause encephalitis following a similar route of infection (equines and potentially human).

It is to be understood that the embodiments and variations shown and described herein are merely illustrative of the principles of this invention and that various modifications may be implemented by those skilled in the art without departing from the scope and spirit of the invention.

TABLE 1

WEE 26S Region Primers

| Name | Length | Sequence |
|---|---|---|
| WEEPRO | 30 | AATCACCCTCTACGGCTGACCTAAATAGGT |
| WEEPR-SST | 24 | GGCTGAGCTCAATAGGTGACGTAG |
| WEE3' | 30 | GTAGTGTATATTAGAGACCCATAGTGAGTC |
| WEE5'SST | 20 | TCCAGATACGAGCTCATACT |

TABLE 1-continued

WEE 26S Region Primers

| Name | Length | Sequence |
|---|---|---|
| WEEN1 | 20 | GGTGCCGCTGGAGGCCGTTT |
| WEEN1A | 20 | GATCTTAGGAGGTCGATAGC |
| WEEN2 | 20 | GGCTGATGAAACCACTCCAC |
| WEEN3 | 20 | CCACCCGTGTGCTATTCACT |
| WEEN3A | 20 | CGCCGTGTTTCAGCCCAATA |
| WEEN4 | 20 | TCACGAGCGGAGCATCTGAG |
| WEEN5 | 20 | GGCATCACCCTCCACCTGAC |
| WEEN6 | 20 | TTGTTATTCTGTTCCGCTGC |
| WEEN7 | 20 | CTATTGATCATGCAGTCGCA |
| WEEN8 | 20 | AGTGGAGCCTCTGCGAGCGT |
| WEEN9 | 20 | GAGGAGTGGGCGGGAAAGGC |
| WEEN10 | 20 | CTAAAACTCGATGTATTTCC |
| WEEN11 | 20 | ACGCGAACGAAGATGAACGG |
| WEEN12 | 20 | ACTGTCATTGTGCTGTGTGG |
| WEEN13 | 20 | CACAGTCATTCCTTCACCAC |
| WEEN14 | 20 | CGTCATCAGAAAGGGGCTTG |
| WEEN15 | 20 | CAAAGCTGACAGGGAGGGAC |
| WEEN16 | 20 | GGAAAGCTGGTAAAGTGCCA |
| WEEN0 | 20 | GGAGAACCACATAAAGTCGA |
| WNSP1 | 25 | GGCTAACGTGGACAGGGACGTGATG |
| WEEP0 | 20 | GGCTATCGACCTCCTAAGAT |
| WEEP0A | 20 | CTGTCGGTTCCCTGGTTTAG |
| WEEP1 | 20 | CTGGGGAACGTCGCCATACT |
| WEEP2 | 20 | CGTTCTCCAGCAGCGTGTCG |
| WEEP2A | 20 | TATTGGGCTGAAACACGGCG |
| WEEP3 | 20 | CTTCAAGTGATCGTAAACGT |
| WEEP4 | 20 | ACTCCAGCCCTTCTCGCCCC |
| WEEP5 | 20 | GTTCGACCAACGCCTTATAC |
| WEEP6 | 20 | AAGGGTGAAAAAGCGGCTGA |
| WEEP7 | 20 | GGTGATTCTGATGATCTCAC |
| WEEP8 | 20 | TGGAAACTGCCGCCTGGAAT |
| WEEP10 | 20 | CCTTGATGTCATGGTCGTGG |
| WEEP11 | 20 | TGCACTGAGTGGTCTGTGTG |
| WEEP12 | 20 | ATGTTTCAGCGTTGGTTGGC |
| WEEP13 | 20 | GTGTTCTCACTGTCACAGAA |
| WEEP14 | 20 | ATGTGTGGTCGCTTCCTTCA |

The nucleotide sequences disclosed in Table 1 from top to bottom are represented in the Sequence Listing as SEQ ID NOs. 10–49, respectively.

TABLE 2

Percentage Variation in Nucleotide and Encoded Amino Acid Sequences Between WEE 71V-1658 and Other Alphaviruses

|  | WEE (BFS1703) | WEE (5614) | EEE | VEE | SIN | RR | ONN | SF |
|---|---|---|---|---|---|---|---|---|
| 5' NTR | — | — |  |  |  |  |  |  |
| nsP1 (nt) | — | (4.5) | 25.1 | 34.8 | 40.9 | 37.8 | 39.7 | 39.1 |
| nsP1 (aa) | — | (6.3) | 15.1 | 32.1 | 40.3 | 35.5 | 37.2 | 33.3 |
| nsP2 (nt) | — | 1.8 | 28.2 | 34.6 | 43.9 | 42.1 | 42.9 | 42.8 |
| nsP2 (aa) | — | 0.6 | 16.2 | 26.5 | 44.9 | 43.2 | 44.9 | 44.4 |
| nsP3 (nt)* | — | 1.8 | 30.2 | 36.7 | 45.8 | 39.3 | 42.6 | 42.2 |
| nsP3 (aa)* | — | 2.1 | 18.8 | 32.4 | 46.3 | 38.7 | 40.9 | 43.5 |
| nsP4 (nt) | (1.8) | (2.4) | 25.6 | 31.4 | 34.7 | 35.3 | 36.0 | 37.0 |
| nsP4 (aa) | (2.6) | (4.3) | 11.7 | 21.4 | 26.8 | 27.3 | 25.8 | 27.4 |
| intervening (nt) | 4.3 | — | 56.6 | 51.5 | 47.6 | 44.7 | 60.0 | 47.7 |
| Capsid (nt) | 2.1 | — | 26.3 | 40.8 | 47.7 | 46.3 | 47.5 | 48.2 |
| Capsid (aa) | 1.5 | — | 16.8 | 43.5 | 52.8 | 53.3 | 54.6 | 54.3 |
| E3 (nt) | 1.1 | — | 45.6 | 40.7 | 38.3 | 51.7 | 47.5 | 46.7 |
| E3 (aa) | 1.7 | — | 38.0 | 39.6 | 39.4 | 46.0 | 45.8 | 43.9 |
| E2 (nt) | 1.2 | — | 51.2 | 52.3 | 36.2 | 51.7 | 55.3 | 52.8 |
| E2 (aa) | 1.0 | — | 59.0 | 60.0 | 31.7 | 63.5 | 65.7 | 64.7 |
| 6K (nt) | 0.6 | — | 53.3 | 46.3 | 26.1 | 51.9 | 50.3 | 54.3 |
| 6K (aa) | 1.8 | — | 65.6 | 59.3 | 32.7 | 72.2 | 69.1 | 75.9 |
| E1 (nt) | 1.5 | — | 43.8 | 45.8 | 29.6 | 47.2 | 48.5 | 44.4 |
| E1 (aa) | 0.5 | — | 49.0 | 51.0 | 23.4 | 51.5 | 54.8 | 50.3 |
| 3' NTR (nt) | 0.7 | — | 57.8 | 55.0 | 53.2 | 69.1 | 65.8 | 60.3 |

*based on N terminal domain, C terminal domain discarded due to lack of homology between alphaviruses
( )based on incomplete sequence data: nsP1 (289 nt) and nsP4 (207 nt for BFS1703, 113 nt for 5614)
— no data

What is claimed is:

1. A recombinant DNA vaccine for inducing protective immune response to Western Equine Encephalitis (WEE) virus strain 71V-1658 in a mammal, comprising a nucleic acid linked to a mammalian expression promoter that is suitable for producing and expressing capside, E1, E2, E3 and 6K structural proteins encoded by the 26S genomic virus RNA.

2. A recombinant DNA vaccine according to claim 1, wherein said mammalian expression promoter is a cytomegalovirus promoter.

3. A recombinant DNA vaccine according to claim 1, wherein said structural proteins are selected from the group consisting of capsid, E1 protein, E2 protein, E3 protein, 6k protein and the 26S polyprotein gene segment of Western Equine Encephalitis (WEE) virus strain 71V-1658.

4. A recombinant DNA vaccine according to claim 1, wherein said nucleic acid is naked.

5. A recombinant DNA vaccine according to claim 1, wherein said nucleic acid is encapsulated in liposomes.

6. A recombinant DNA vaccine according to claim 1, wherein said nucleic acid is coated onto gold particles.

7. A recombinant DNA vaccine according to claim 1, wherein said structural proteins of WEE virus strain 71V-1658 in SEQ ID NO: 4 are operationally linked to a cytomegalovirus (CMV) promoter in a nucleic acid pVHX-6 of SEQ ID NO: 7.

* * * * *

SEQUENCE LISTING

```
<160> NUMBER OF SEQ ID NOS: 49

<210> SEQ ID NO 1
<211> LENGTH: 11484
<212> TYPE: DNA
<213> ORGANISM: Western equine encephalomyelitis virus - strain 71V-1658
<220> FEATURE:
<221> NAME/KEY: CDS
<222> LOCATION: (25)..(7428)
<223> OTHER INFORMATION: 5' UTR <1 .. 24
<220> FEATURE:
<221> NAME/KEY: CDS
<222> LOCATION: (7473)..(11183)
<223> OTHER INFORMATION: encodes nucleocapsid, E3, E2, 6K and E1
      proteins

<400> SEQUENCE: 1
accctacaaa ctaatcgatc caat atg gaa aga att cac gtt gac tta gat      51
                         Met Glu Arg Ile His Val Asp Leu Asp
                          1               5 gct gac agc ccg tat gtc aag tcg tta cag cgg acg ttt cca caa ttt     99
Ala Asp Ser Pro Tyr Val Lys Ser Leu Gln Arg Thr Phe Pro Gln Phe
 10              15                  20                  25 gag atc gaa gca agg cag gtc act gac aat gac cat gcc aat gcc aga    147
Glu Ile Glu Ala Arg Gln Val Thr Asp Asn Asp His Ala Asn Ala Arg
                 30                  35                  40 gcg ttt tcg cat gtg gca aca aag ctc att gag agc gaa gtc gac cgg    195
Ala Phe Ser His Val Ala Thr Lys Leu Ile Glu Ser Glu Val Asp Arg
             45                  50                  55
```

-continued

| | | |
|---|---|---|
| gac caa gtt atc ttg gac att gga agt gcg ccc gtc aga cat gca cat<br>Asp Gln Val Ile Leu Asp Ile Gly Ser Ala Pro Val Arg His Ala His<br>60                      65                      70 | | 243 |
| tcc aat cac cgc tat cat tgt atc tgc cct atg ata agc gct gaa gac<br>Ser Asn His Arg Tyr His Cys Ile Cys Pro Met Ile Ser Ala Glu Asp<br>75                      80                      85 | | 291 |
| ccg gac aga cta caa cgg tat gca gaa aga ctt aag aaa agt gac att<br>Pro Asp Arg Leu Gln Arg Tyr Ala Glu Arg Leu Lys Lys Ser Asp Ile<br>90                      95                    100                105 | | 339 |
| acc gac aag aac ata gcc tct aag gcg gca gac ctg ctg gaa gtc atg<br>Thr Asp Lys Asn Ile Ala Ser Lys Ala Ala Asp Leu Leu Glu Val Met<br>110                        115                    120 | | 387 |
| tca aca cca gac gca gag act cca tct ctg tgt atg cac aca gac gcc<br>Ser Thr Pro Asp Ala Glu Thr Pro Ser Leu Cys Met His Thr Asp Ala<br>            125                    130                    135 | | 435 |
| acg tgt agg tac ttt gga agt gta gca gta tac caa gat gtg tac gca<br>Thr Cys Arg Tyr Phe Gly Ser Val Ala Val Tyr Gln Asp Val Tyr Ala<br>140                        145                    150 | | 483 |
| gtc cat gca ccg aca tca atc tac cac cag gcg ctt aaa gga gtt agg<br>Val His Ala Pro Thr Ser Ile Tyr His Gln Ala Leu Lys Gly Val Arg<br>            155                    160                    165 | | 531 |
| aca att tac tgg ata ggc ttt gac acg acc cct ttt atg tac aaa aac<br>Thr Ile Tyr Trp Ile Gly Phe Asp Thr Thr Pro Phe Met Tyr Lys Asn<br>170                        175                    180                185 | | 579 |
| atg gca ggt tcc tac cct act tac aac acg aac tgg gct gac gag aga<br>Met Ala Gly Ser Tyr Pro Thr Tyr Asn Thr Asn Trp Ala Asp Glu Arg<br>                    190                    195                    200 | | 627 |
| gta ttg gaa gca cgt aac att ggc ctc ggt aac tca gat ctt cag gag<br>Val Leu Glu Ala Arg Asn Ile Gly Leu Gly Asn Ser Asp Leu Gln Glu<br>            205                    210                    215 | | 675 |
| agc agg ctt gga aaa ctc tca atc ctt agg aag aag agg ctc caa cct<br>Ser Arg Leu Gly Lys Leu Ser Ile Leu Arg Lys Lys Arg Leu Gln Pro<br>220                        225                    230 | | 723 |
| act aat aag atc ata ttc tcg gtt ggt tca aca atc tac aca gaa gat<br>Thr Asn Lys Ile Ile Phe Ser Val Gly Ser Thr Ile Tyr Thr Glu Asp<br>            235                    240                    245 | | 771 |
| aga tca ctg tta cgt agc tgg cat ctt cca aac gtg ttc cac ttg aaa<br>Arg Ser Leu Leu Arg Ser Trp His Leu Pro Asn Val Phe His Leu Lys<br>250                        255                    260                265 | | 819 |
| gga aag tct aac ttc aca ggt aga tgt ggg acc att gtc agc tgt gaa<br>Gly Lys Ser Asn Phe Thr Gly Arg Cys Gly Thr Ile Val Ser Cys Glu<br>                    270                    275                    280 | | 867 |
| ggg tac gtc atc aaa aag ata acg atc agc cca gga cta tac ggt aaa<br>Gly Tyr Val Ile Lys Lys Ile Thr Ile Ser Pro Gly Leu Tyr Gly Lys<br>            285                    290                    295 | | 915 |
| gtt gag aac ttg gcg tcc aca atg cat cgc gag ggt ttc ttg agt tgc<br>Val Glu Asn Leu Ala Ser Thr Met His Arg Glu Gly Phe Leu Ser Cys<br>300                        305                    310 | | 963 |
| aaa gtc aca gat acg ctg cgc ggc gag agg gtt tct ttt gct gtg tgt<br>Lys Val Thr Asp Thr Leu Arg Gly Glu Arg Val Ser Phe Ala Val Cys<br>            315                    320                    325 | | 1011 |
| acg tat gta cca gcc aca ctt tgc gat cag atg aca ggg att ctg gca<br>Thr Tyr Val Pro Ala Thr Leu Cys Asp Gln Met Thr Gly Ile Leu Ala<br>330                        335                    340                345 | | 1059 |
| act gac gtt agt gtg gat gac gca caa aaa cta ttg gtt ggg ctc aac<br>Thr Asp Val Ser Val Asp Asp Ala Gln Lys Leu Leu Val Gly Leu Asn<br>                    350                    355                    360 | | 1107 |
| caa agg att gtc gtc aat ggt agg acg caa aga aat act aac aca atg<br>Gln Arg Ile Val Val Asn Gly Arg Thr Gln Arg Asn Thr Asn Thr Met<br>            365                    370                    375 | | 1155 |

```
                                                                -continued cag aac tat cta tta cca gtg gtc gcc cag gcg ttt tcc agg tgg gcg           1203
Gln Asn Tyr Leu Leu Pro Val Val Ala Gln Ala Phe Ser Arg Trp Ala
        380                 385                 390 cgt gaa cat cgt gcc gac ttg gac gac gag aaa gaa cta ggg gtg cgg           1251
Arg Glu His Arg Ala Asp Leu Asp Asp Glu Lys Glu Leu Gly Val Arg
395                 400                 405 gag cgc act ctt act atg ggc tgc tgc tgg gct ttc aag acc cag aaa           1299
Glu Arg Thr Leu Thr Met Gly Cys Cys Trp Ala Phe Lys Thr Gln Lys
410                 415                 420                 425 atc aca tcc atc tac aag aag cct ggt acg caa aca att aag aaa gta           1347
Ile Thr Ser Ile Tyr Lys Lys Pro Gly Thr Gln Thr Ile Lys Lys Val
                430                 435                 440 cct gcc gtc ttt gac tca ttt gtg att cca cgc ctt acc agc cac ggg           1395
Pro Ala Val Phe Asp Ser Phe Val Ile Pro Arg Leu Thr Ser His Gly
                445                 450                 455 ctc gat atg ggc ttc cgc cgt agg ctc aag ctg ctt gaa cca act               1443
Leu Asp Met Gly Phe Arg Arg Arg Leu Lys Leu Leu Glu Pro Thr
            460                 465                 470 gtc aaa ccc gca ccg gct att aca atg gcc gat gtg gag cat ctg cgt           1491
Val Lys Pro Ala Pro Ala Ile Thr Met Ala Asp Val Glu His Leu Arg
475                 480                 485 ggc tta cag caa gaa gct gaa gaa gtg gct gca gcg gaa gag atc aga           1539
Gly Leu Gln Gln Glu Ala Glu Glu Val Ala Ala Ala Glu Glu Ile Arg
490                 495                 500                 505 gaa gcc ctg cca ccc ttg ctc cct gaa ata gaa aaa gag acc gta gag           1587
Glu Ala Leu Pro Pro Leu Leu Pro Glu Ile Glu Lys Glu Thr Val Glu
                510                 515                 520 gca gaa gta gac ctc att atg caa gag gca gga gca ggt agc gtg gag           1635
Ala Glu Val Asp Leu Ile Met Gln Glu Ala Gly Ala Gly Ser Val Glu
                525                 530                 535 aca cca cga gga cac atc agg gtg aca agt tac cca ggc gaa gag aag           1683
Thr Pro Arg Gly His Ile Arg Val Thr Ser Tyr Pro Gly Glu Glu Lys
            540                 545                 550 att ggg tct tac gct ata ctt tca ccc cag gcg gta ttg aat agt gaa           1731
Ile Gly Ser Tyr Ala Ile Leu Ser Pro Gln Ala Val Leu Asn Ser Glu
555                 560                 565 aaa ctg gcg tgt atc cac cca ttg gcg gaa caa gta ctg gta atg act           1779
Lys Leu Ala Cys Ile His Pro Leu Ala Glu Gln Val Leu Val Met Thr
570                 575                 580                 585 cac aaa ggt agg gca ggg aga tac aaa gtc gag cca tac cac ggt aag           1827
His Lys Gly Arg Ala Gly Arg Tyr Lys Val Glu Pro Tyr His Gly Lys
                590                 595                 600 gtc att gta cca gaa ggg acg gcg gtc cct gtt caa gac ttc cag gca           1875
Val Ile Val Pro Glu Gly Thr Ala Val Pro Val Gln Asp Phe Gln Ala
                605                 610                 615 ttg agt gag agc gct acg atc gtt ttc aac gag agg gag ttc gta aac           1923
Leu Ser Glu Ser Ala Thr Ile Val Phe Asn Glu Arg Glu Phe Val Asn
            620                 625                 630 aga tac ctg cac cac atc gca atc aac gga gga gcg cta aac act gac           1971
Arg Tyr Leu His His Ile Ala Ile Asn Gly Gly Ala Leu Asn Thr Asp
635                 640                 645 gaa gag tac tat aag act gta aag act cag gac aca gac tca gaa tac           2019
Glu Glu Tyr Tyr Lys Thr Val Lys Thr Gln Asp Thr Asp Ser Glu Tyr
650                 655                 660                 665 gtc ttc gat att gac gca cga aag tgt gtt aag cga gaa gac gca ggt           2067
Val Phe Asp Ile Asp Ala Arg Lys Cys Val Lys Arg Glu Asp Ala Gly
                670                 675                 680 ccc ttg tgc cta acc ggt gat ctg gta gat cca cca ttt cac gag ttt           2115
Pro Leu Cys Leu Thr Gly Asp Leu Val Asp Pro Pro Phe His Glu Phe
```

```
                685                  690                  695
gcg tac gag agt ctc aag aca cga cca gca gca cct cac aaa gtc cca      2163
Ala Tyr Glu Ser Leu Lys Thr Arg Pro Ala Ala Pro His Lys Val Pro
        700                  705                  710 acc atc gga gtc tat gga gtg cca ggt tca ggt aaa tct gga atc atc      2211
Thr Ile Gly Val Tyr Gly Val Pro Gly Ser Gly Lys Ser Gly Ile Ile
715                  720                  725 aaa agc gct gtg act aag aaa gat ctg gtt gtg agt gcg aag aag gaa      2259
Lys Ser Ala Val Thr Lys Lys Asp Leu Val Val Ser Ala Lys Lys Glu
730                  735                  740                  745 aac tgc gca gaa atc atc agg gat gta agg agg atg aga cgt atg gat      2307
Asn Cys Ala Glu Ile Ile Arg Asp Val Arg Arg Met Arg Arg Met Asp
            750                  755                  760 gtt gct gct agg act gtc gat tca gtg ctt cta aat ggg gtt aag cac      2355
Val Ala Ala Arg Thr Val Asp Ser Val Leu Leu Asn Gly Val Lys His
                765                  770                  775 ccc gtt aac act ctg tac att gat gag gca ttt gcc tgc cat gca ggg      2403
Pro Val Asn Thr Leu Tyr Ile Asp Glu Ala Phe Ala Cys His Ala Gly
                    780                  785                  790 acg ctg ctg gca ctg att gcc atc gtc aaa cct aag aaa gtg gta ttg      2451
Thr Leu Leu Ala Leu Ile Ala Ile Val Lys Pro Lys Lys Val Val Leu
795                  800                  805 tgc ggg gac cca aaa caa tgc ggc ttc ttt aac atg atg tgc ctg aaa      2499
Cys Gly Asp Pro Lys Gln Cys Gly Phe Phe Asn Met Met Cys Leu Lys
810                  815                  820                  825 gta cat ttt aac cat gac ata tgc act gaa gtg tac cat aaa agc atc      2547
Val His Phe Asn His Asp Ile Cys Thr Glu Val Tyr His Lys Ser Ile
            830                  835                  840 tct agg agg tgc aca cag act gta acc gcc atc gtc tcc acg ctc ttc      2595
Ser Arg Arg Cys Thr Gln Thr Val Thr Ala Ile Val Ser Thr Leu Phe
                845                  850                  855 tac gac aag cga atg aag acg gtt aac cca tgt gct gat aaa atc atc      2643
Tyr Asp Lys Arg Met Lys Thr Val Asn Pro Cys Ala Asp Lys Ile Ile
                    860                  865                  870 ata gat acc aca ggg acc aca aag ccg cac aaa gat gat ctg att cta      2691
Ile Asp Thr Thr Gly Thr Thr Lys Pro His Lys Asp Asp Leu Ile Leu
875                  880                  885 acc tgt ttc aga gga tgg gtg aaa cag cta cag att gac tac aaa aat      2739
Thr Cys Phe Arg Gly Trp Val Lys Gln Leu Gln Ile Asp Tyr Lys Asn
890                  895                  900                  905 cac gaa atc atg act gcg gct gca tcg caa gga ctt acg cgg aaa ggc      2787
His Glu Ile Met Thr Ala Ala Ala Ser Gln Gly Leu Thr Arg Lys Gly
            910                  915                  920 gtt tat gct gtc agg tac aaa gtc aac gag aat cca ctc tac tcg cag      2835
Val Tyr Ala Val Arg Tyr Lys Val Asn Glu Asn Pro Leu Tyr Ser Gln
                925                  930                  935 act tct gag cac gtg aac gtg tta ctt aca cgc aca gaa aaa cgc att      2883
Thr Ser Glu His Val Asn Val Leu Leu Thr Arg Thr Glu Lys Arg Ile
                    940                  945                  950 gtc tgg aag acg cta gct ggt gat ccc tgg ata aag aca ctt aca gct      2931
Val Trp Lys Thr Leu Ala Gly Asp Pro Trp Ile Lys Thr Leu Thr Ala
955                  960                  965 aaa tat ccc ggg gat ttc acg gct tca ttg gac gac tgg cag cgc gaa      2979
Lys Tyr Pro Gly Asp Phe Thr Ala Ser Leu Asp Asp Trp Gln Arg Glu
970                  975                  980                  985 cac gac gcc att atg gca cgc gtt ctt gat aag ccg cag aca gct  gat     3027
His Asp Ala Ile Met Ala Arg Val Leu Asp Lys Pro Gln Thr Ala  Asp
            990                  995                  1000 gtg ttc cag aat  aag gtg aac gtc tgc  tgg gcg aag gct tta  gag       3072
```

```
                Val Phe Gln Asn Lys Val Asn Val Cys Trp Ala Lys Ala Leu Glu
                             1005                1010                1015 cca gtc ttg gcc acg gcc aac att gtg ctg acg aga cag cag tgg           3117
Pro Val Leu Ala Thr Ala Asn Ile Val Leu Thr Arg Gln Gln Trp
            1020                1025                1030 gag acg ttg cac cca ttc aag cat gac aga gcg tac tca cct gaa           3162
Glu Thr Leu His Pro Phe Lys His Asp Arg Ala Tyr Ser Pro Glu
            1035                1040                1045 atg gca ctg aac ttc ttt tgc acc agg ttc ttt gga gta gac ctg           3207
Met Ala Leu Asn Phe Phe Cys Thr Arg Phe Phe Gly Val Asp Leu
            1050                1055                1060 gac agt ggg tta ttt tcc gct cct acc gtc gca ctt act tac agg           3252
Asp Ser Gly Leu Phe Ser Ala Pro Thr Val Ala Leu Thr Tyr Arg
            1065                1070                1075 gat cag cac tgg gat aac tcg cca ggg aag aac atg tat ggg ctt           3297
Asp Gln His Trp Asp Asn Ser Pro Gly Lys Asn Met Tyr Gly Leu
            1080                1085                1090 aat aga gag gta gca aag gag ttg tca cgg cga tat ccg tgc atc           3342
Asn Arg Glu Val Ala Lys Glu Leu Ser Arg Arg Tyr Pro Cys Ile
            1095                1100                1105 aca aaa gcg gtt gac aca ggc agg gta gct gat ata agg aat aat           3387
Thr Lys Ala Val Asp Thr Gly Arg Val Ala Asp Ile Arg Asn Asn
            1110                1115                1120 acc atc aag gac tac tct cca aca att aat gtg gtt cca tta aat           3432
Thr Ile Lys Asp Tyr Ser Pro Thr Ile Asn Val Val Pro Leu Asn
            1125                1130                1135 cgc cgg ttg ccc cac tcg ttg atc gtt gac cac aaa gga cag ggt           3477
Arg Arg Leu Pro His Ser Leu Ile Val Asp His Lys Gly Gln Gly
            1140                1145                1150 aca act gat cac agc gga ttc cta tct aag atg aag ggc aaa tct           3522
Thr Thr Asp His Ser Gly Phe Leu Ser Lys Met Lys Gly Lys Ser
            1155                1160                1165 gtg ttg gtg atc ggc gat cct atc agc att cca ggg aag aaa gta           3567
Val Leu Val Ile Gly Asp Pro Ile Ser Ile Pro Gly Lys Lys Val
            1170                1175                1180 gag tcc atg ggt cca ttg ccc act aat acc atc agg tgt gat ctc           3612
Glu Ser Met Gly Pro Leu Pro Thr Asn Thr Ile Arg Cys Asp Leu
            1185                1190                1195 gat ttg gga ata cct agc cat gtc ggt aaa tat gac att atc ttt           3657
Asp Leu Gly Ile Pro Ser His Val Gly Lys Tyr Asp Ile Ile Phe
            1200                1205                1210 gtc aat gtt agg acc ccg tac agg aac cat cac tac caa cag tgc           3702
Val Asn Val Arg Thr Pro Tyr Arg Asn His His Tyr Gln Gln Cys
            1215                1220                1225 gag gat cac gct atc cac cac agc atg cta acg tgt aag gct gtc           3747
Glu Asp His Ala Ile His His Ser Met Leu Thr Cys Lys Ala Val
            1230                1235                1240 cac cac ctg aac act ggc gga aca tgt gtg gct ata ggg tat ggg           3792
His His Leu Asn Thr Gly Gly Thr Cys Val Ala Ile Gly Tyr Gly
            1245                1250                1255 ctt gct gat cgc gca acc gag aat atc atc act gcg gtg gca cgc           3837
Leu Ala Asp Arg Ala Thr Glu Asn Ile Ile Thr Ala Val Ala Arg
            1260                1265                1270 tca ttt agg ttt acc cgt gtc tgt cag cct aag aac act gcc gaa           3882
Ser Phe Arg Phe Thr Arg Val Cys Gln Pro Lys Asn Thr Ala Glu
            1275                1280                1285 aat act gag gtt ctc ttc gtg ttc ttc ggc aag gac aac ggc aac           3927
Asn Thr Glu Val Leu Phe Val Phe Phe Gly Lys Asp Asn Gly Asn
            1290                1295                1300
```

| | | |
|---|---|---|
| cac aca cat gac cag gac aga ctc ggt gta gtg ctt gac aac atc<br>His Thr His Asp Gln Asp Arg Leu Gly Val Val Leu Asp Asn Ile<br>　　　　1305　　　　　　　　1310　　　　　　　　1315 | 3972 | |
| tat caa ggg tca acc agg tac gag gca ggg aga gct cca gcg tac<br>Tyr Gln Gly Ser Thr Arg Tyr Glu Ala Gly Arg Ala Pro Ala Tyr<br>　　　1320　　　　　　　　1325　　　　　　　　1330 | 4017 | |
| aga gtg atc aga ggt gac att agc aag agc gct gac caa gct atc<br>Arg Val Ile Arg Gly Asp Ile Ser Lys Ser Ala Asp Gln Ala Ile<br>1335　　　　　　　　1340　　　　　　　　1345 | 4062 | |
| gtt aat gct gct aat agc aaa ggt caa cca ggt tcc gga gtg tgc<br>Val Asn Ala Ala Asn Ser Lys Gly Gln Pro Gly Ser Gly Val Cys<br>　　1350　　　　　　　　1355　　　　　　　　1360 | 4107 | |
| ggt gca ctg tac cga aaa tgg ccg gct gct ttt gat aga cag cca<br>Gly Ala Leu Tyr Arg Lys Trp Pro Ala Ala Phe Asp Arg Gln Pro<br>　　　　1365　　　　　　　　1370　　　　　　　　1375 | 4152 | |
| ata gct gtc ggg acg gct aga ctt gtg aag cac gaa ccg ctc atc<br>Ile Ala Val Gly Thr Ala Arg Leu Val Lys His Glu Pro Leu Ile<br>　　　1380　　　　　　　　1385　　　　　　　　1390 | 4197 | |
| ata cat gct gta gga ccc aat ttt tct aag atg ccg gaa ccg gag<br>Ile His Ala Val Gly Pro Asn Phe Ser Lys Met Pro Glu Pro Glu<br>1395　　　　　　　　1400　　　　　　　　1405 | 4242 | |
| ggc gac ctt aag ctc gca gct gcc tac atg agc ata gcg tcc atc<br>Gly Asp Leu Lys Leu Ala Ala Ala Tyr Met Ser Ile Ala Ser Ile<br>　　1410　　　　　　　　1415　　　　　　　　1420 | 4287 | |
| gtc aac gct gag cgg att aca aaa ata tca gta ccg cta ctg tca<br>Val Asn Ala Glu Arg Ile Thr Lys Ile Ser Val Pro Leu Leu Ser<br>　　　　1425　　　　　　　　1430　　　　　　　　1435 | 4332 | |
| acc ggc atc tat tct ggt ggc aaa gat cga gtg atg caa tca ttg<br>Thr Gly Ile Tyr Ser Gly Gly Lys Asp Arg Val Met Gln Ser Leu<br>　　　1440　　　　　　　　1445　　　　　　　　1450 | 4377 | |
| cat cac ctg ttc act gct ttc gac act acg gat gcc gat gtc acc<br>His His Leu Phe Thr Ala Phe Asp Thr Thr Asp Ala Asp Val Thr<br>1455　　　　　　　　1460　　　　　　　　1465 | 4422 | |
| ata tat tgc ttg gat aaa caa tgg gag acc agg ata atc gag gcc<br>Ile Tyr Cys Leu Asp Lys Gln Trp Glu Thr Arg Ile Ile Glu Ala<br>　　1470　　　　　　　　1475　　　　　　　　1480 | 4467 | |
| att cac cgc aaa gaa agc gtc gaa att ctg gat gat gac aag cca<br>Ile His Arg Lys Glu Ser Val Glu Ile Leu Asp Asp Asp Lys Pro<br>　　　　1485　　　　　　　　1490　　　　　　　　1495 | 4512 | |
| gta gac att gac ttg gtc agg gtc cac cca aac agc tct ttg gca<br>Val Asp Ile Asp Leu Val Arg Val His Pro Asn Ser Ser Leu Ala<br>　　　1500　　　　　　　　1505　　　　　　　　1510 | 4557 | |
| ggc aga cca ggt tac tcc gtc aat gag ggc aag ttg tat tca tac<br>Gly Arg Pro Gly Tyr Ser Val Asn Glu Gly Lys Leu Tyr Ser Tyr<br>1515　　　　　　　　1520　　　　　　　　1525 | 4602 | |
| ctg gaa ggt aca cga ttc cat cag acc gcc aag gac att gcc gaa<br>Leu Glu Gly Thr Arg Phe His Gln Thr Ala Lys Asp Ile Ala Glu<br>　　1530　　　　　　　　1535　　　　　　　　1540 | 4647 | |
| atc cat gca atg tgg ccc aac aaa tct gag gct aat gag cag att<br>Ile His Ala Met Trp Pro Asn Lys Ser Glu Ala Asn Glu Gln Ile<br>　　　　1545　　　　　　　　1550　　　　　　　　1555 | 4692 | |
| tgc ttg tac atc ctg ggg gag agt atg tcc agc atc cgc tcc aaa<br>Cys Leu Tyr Ile Leu Gly Glu Ser Met Ser Ser Ile Arg Ser Lys<br>　　　1560　　　　　　　　1565　　　　　　　　1570 | 4737 | |
| tgc cca gta gag gag tca gag gcg tct gct cca cct cac aca ctt<br>Cys Pro Val Glu Glu Ser Glu Ala Ser Ala Pro Pro His Thr Leu<br>1575　　　　　　　　1580　　　　　　　　1585 | 4782 | |
| cca tgc ctg tgt aat tac gct atg acg gct gag cgc gta tac agg<br>Pro Cys Leu Cys Asn Tyr Ala Met Thr Ala Glu Arg Val Tyr Arg<br>　　1590　　　　　　　　1595　　　　　　　　1600 | 4827 | |

-continued

| | |
|---|---|
| ttg cgc tct gcg aag aaa gaa cag ttc gcc gta tgc tca tca ttc<br>Leu Arg Ser Ala Lys Lys Glu Gln Phe Ala Val Cys Ser Ser Phe<br>1605                               1610                            1615 | 4872 |
| ctg ttg ccg aag tac agg atc aca ggc gtg cag aag cta cag tgc<br>Leu Leu Pro Lys Tyr Arg Ile Thr Gly Val Gln Lys Leu Gln Cys<br>1620                                 1625                            1630 | 4917 |
| agc aaa cca gtc ctg ttt tca ggc gtc gta cca ccg gct gta cac<br>Ser Lys Pro Val Leu Phe Ser Gly Val Val Pro Pro Ala Val His<br>1635                                 1640                            1645 | 4962 |
| ccc agg aag tac gcg gaa ata att cta gaa acg cca cca ccg cca<br>Pro Arg Lys Tyr Ala Glu Ile Ile Leu Glu Thr Pro Pro Pro Pro<br>1650                                 1655                            1660 | 5007 |
| gca acg aca acc gta ata tgt gaa cca act gtg cca gaa cgt ata<br>Ala Thr Thr Thr Val Ile Cys Glu Pro Thr Val Pro Glu Arg Ile<br>1665                                 1670                            1675 | 5052 |
| ccc agt ccg gtg att tct aga gca cca agt gcg gaa tca ctg cta<br>Pro Ser Pro Val Ile Ser Arg Ala Pro Ser Ala Glu Ser Leu Leu<br>1680                                 1685                            1690 | 5097 |
| tcg ctt ggc ggc gtc tcg ttc tct agc tct gcc aca cgc tcg tca<br>Ser Leu Gly Gly Val Ser Phe Ser Ser Ser Ala Thr Arg Ser Ser<br>1695                                 1700                            1705 | 5142 |
| acc gcc tgg agc gac tat gac agg cgg ttt gtg gtt aca gct gat<br>Thr Ala Trp Ser Asp Tyr Asp Arg Arg Phe Val Val Thr Ala Asp<br>1710                                 1715                            1720 | 5187 |
| gtg cat caa gcg aac acg tct acg tgg agc atc cct agt gct cct<br>Val His Gln Ala Asn Thr Ser Thr Trp Ser Ile Pro Ser Ala Pro<br>1725                                 1730                            1735 | 5232 |
| ggc ttg gac gtc cag ctg cct tct gac gtc act gat tcc cac tgg<br>Gly Leu Asp Val Gln Leu Pro Ser Asp Val Thr Asp Ser His Trp<br>1740                                 1745                            1750 | 5277 |
| agt att cca agt gca tca ggc ttt gaa gtg aga aca cca tct gta<br>Ser Ile Pro Ser Ala Ser Gly Phe Glu Val Arg Thr Pro Ser Val<br>1755                                 1760                            1765 | 5322 |
| cag gac cta act gcg gag tgt gcg aag cct cgt gga ctg gcc gaa<br>Gln Asp Leu Thr Ala Glu Cys Ala Lys Pro Arg Gly Leu Ala Glu<br>1770                                 1775                            1780 | 5367 |
| ata atg caa gac ttc aat act gct cct ttc cag ttt ctt tcg gac<br>Ile Met Gln Asp Phe Asn Thr Ala Pro Phe Gln Phe Leu Ser Asp<br>1785                                 1790                            1795 | 5412 |
| tac aga cca gta ccg gca cca cgg aga cgc ccc atc cca tca cct<br>Tyr Arg Pro Val Pro Ala Pro Arg Arg Arg Pro Ile Pro Ser Pro<br>1800                                 1805                            1810 | 5457 |
| aga tcg acg gct tcc gca cct cca gtt cca aag cca cgc agg act<br>Arg Ser Thr Ala Ser Ala Pro Pro Val Pro Lys Pro Arg Arg Thr<br>1815                                 1820                            1825 | 5502 |
| aag tac caa caa cca cca gga gtc gct aga gcg atc tca gaa gcg<br>Lys Tyr Gln Gln Pro Pro Gly Val Ala Arg Ala Ile Ser Glu Ala<br>1830                                 1835                            1840 | 5547 |
| gag ttg gac gag tac atc cgt caa cac tcc aac tga cgg tat gaa<br>Glu Leu Asp Glu Tyr Ile Arg Gln His Ser Asn    Arg Tyr Glu<br>1845                                 1850                            1855 | 5592 |
| gcg gga gcg tat att ttc tca tcg gaa aca ggc caa ggt cac ctt<br>Ala Gly Ala Tyr Ile Phe Ser Ser Glu Thr Gly Gln Gly His Leu<br>1860                                 1865                            1870 | 5637 |
| caa cag aaa tca gta cgt caa tgt aaa cta caa gaa cct ata ttg<br>Gln Gln Lys Ser Val Arg Gln Cys Lys Leu Gln Glu Pro Ile Leu<br>1875                                 1880                            1885 | 5682 |
| gat cgg gcc gtc cat gag aag tat tac gcc ccg cgc ctc gat ctc<br>Asp Arg Ala Val His Glu Lys Tyr Tyr Ala Pro Arg Leu Asp Leu | 5727 |

-continued

| | | | | |
|---|---|---|---|---|
| | 1890 | 1895 | 1900 | |
| gaa aga gag aaa atg  Glu Arg Glu Lys Met       1905 | tta cag aag aaa ctg  Leu Gln Lys Lys Leu       1910 | caa tta tgc gcc tct  Gln Leu Cys Ala Ser       1915 | | 5772 |
| gaa gga aat aga agc  Glu Gly Asn Arg Ser       1920 | agg tat caa tca cga  Arg Tyr Gln Ser Arg       1925 | aaa gta gaa aat atg  Lys Val Glu Asn Met       1930 | | 5817 |
| aaa gca att aca gcg  Lys Ala Ile Thr Ala       1935 | gag cga ctc att tct  Glu Arg Leu Ile Ser       1940 | gga ttg ggc aca tat  Gly Leu Gly Thr Tyr       1945 | | 5862 |
| cta tca tca gaa gtg  Leu Ser Ser Glu Val       1950 | aat cct gtc gag tgt  Asn Pro Val Glu Cys       1955 | tac aga gtc aat tat  Tyr Arg Val Asn Tyr       1960 | | 5907 |
| cct gta cca atc tac  Pro Val Pro Ile Tyr       1965 | tcg tca acg gta att  Ser Ser Thr Val Ile       1970 | aac agg ttt aca tct  Asn Arg Phe Thr Ser       1975 | | 5952 |
| gca gag gtc gcg gtt  Ala Glu Val Ala Val       1980 | aaa acg tgc aac tta  Lys Thr Cys Asn Leu       1985 | gtt atc caa gag aat  Val Ile Gln Glu Asn       1990 | | 5997 |
| tac cct aca gta gcc  Tyr Pro Thr Val Ala       1995 | agt tat tgt ata aca  Ser Tyr Cys Ile Thr       2000 | gat gaa tac gat gcg  Asp Glu Tyr Asp Ala       2005 | | 6042 |
| tat ctt gac atg gtg  Tyr Leu Asp Met Val       2010 | gac ggc gca tcg tgc  Asp Gly Ala Ser Cys       2015 | tgt cta gat aca gcc  Cys Leu Asp Thr Ala       2020 | | 6087 |
| act ttt tgt ccg gct  Thr Phe Cys Pro Ala       2025 | aaa ctg aga agc tac  Lys Leu Arg Ser Tyr       2030 | cca aag aag cat agc  Pro Lys Lys His Ser       2035 | | 6132 |
| tat ttg cag cca gag  Tyr Leu Gln Pro Glu       2040 | ata aga tca gcc gtc  Ile Arg Ser Ala Val       2045 | cca tcg cct ata cag  Pro Ser Pro Ile Gln       2050 | | 6177 |
| aat aca tta caa aat  Asn Thr Leu Gln Asn       2055 | gta ttg gct gca gct  Val Leu Ala Ala Ala       2060 | act aaa agg aat tgc  Thr Lys Arg Asn Cys       2065 | | 6222 |
| aac gtt acc caa atg  Asn Val Thr Gln Met       2070 | cga gaa tta cct gtc  Arg Glu Leu Pro Val       2075 | tta gat tcg gcg gca  Leu Asp Ser Ala Ala       2080 | | 6267 |
| ttt aat gtt gat tgt  Phe Asn Val Asp Cys       2085 | ttc aag aaa tac gca  Phe Lys Lys Tyr Ala       2090 | tgc aat gat gag tac  Cys Asn Asp Glu Tyr       2095 | | 6312 |
| tgg gat acc ttt cgc  Trp Asp Thr Phe Arg       2100 | gat aac cct att cgg  Asp Asn Pro Ile Arg       2105 | cta act aca gag aac  Leu Thr Thr Glu Asn       2110 | | 6357 |
| gtt acg caa tat gtg  Val Thr Gln Tyr Val       2115 | aca aag ctg aaa ggg  Thr Lys Leu Lys Gly       2120 | ccg aaa gca gca gca  Pro Lys Ala Ala Ala       2125 | | 6402 |
| ttg ttt gcg aat act  Leu Phe Ala Asn Thr       2130 | cat aat cta aaa ccg  His Asn Leu Lys Pro       2135 | ttg cag gag ata cca  Leu Gln Glu Ile Pro       2140 | | 6447 |
| atg gat caa ttc gtc  Met Asp Gln Phe Val       2145 | atg gat cta aag aga  Met Asp Leu Lys Arg       2150 | gat gtc aaa gtt act  Asp Val Lys Val Thr       2155 | | 6492 |
| ccc ggc acg aaa cat  Pro Gly Thr Lys His       2160 | aca gag gag cgg cct  Thr Glu Glu Arg Pro       2165 | aag gtg cag gtt att  Lys Val Gln Val Ile       2170 | | 6537 |
| cag gct gca gat ccc  Gln Ala Ala Asp Pro       2175 | ctt gct acc gct tac  Leu Ala Thr Ala Tyr       2180 | ctt tgc ggg atc cat  Leu Cys Gly Ile His       2185 | | 6582 |
| cgg gaa tta gtc cgt  | aga ctg aat gcg gtg  | ctt ctg cca aat atc  | | 6627 |

```
                                                                                          -continued Arg Glu Leu Val Arg   Arg Leu Asn Ala Val   Leu Leu Pro Asn Ile
        2190                  2195                  2200 cat act ctc ttc gac   atg tca gcg gaa gat   ttt gat gcg att att       6672
His Thr Leu Phe Asp   Met Ser Ala Glu Asp   Phe Asp Ala Ile Ile
        2205                  2210                  2215 gct gaa cat ttc cac   cac ggc gac cca gta   ttg gaa acg gac atc       6717
Ala Glu His Phe His   His Gly Asp Pro Val   Leu Glu Thr Asp Ile
        2220                  2225                  2230 gcg tcg ttt gat aaa   agc gaa gac gac gct   atc gcc att tcg gcg       6762
Ala Ser Phe Asp Lys   Ser Glu Asp Asp Ala   Ile Ala Ile Ser Ala
        2235                  2240                  2245 ttg atg atc ctt gag   gac tta ggt gtc gac   caa ccg ctc tta gat       6807
Leu Met Ile Leu Glu   Asp Leu Gly Val Asp   Gln Pro Leu Leu Asp
        2250                  2255                  2260 ttg ata gag gcg gcg   ttc ggc aat atc aca   tct gtg cac cta cct       6852
Leu Ile Glu Ala Ala   Phe Gly Asn Ile Thr   Ser Val His Leu Pro
        2265                  2270                  2275 aca gga acg agg ttt   aaa ttt ggt gcc atg   atg aaa tcc ggt atg       6897
Thr Gly Thr Arg Phe   Lys Phe Gly Ala Met   Met Lys Ser Gly Met
        2280                  2285                  2290 ttc tta acg ctg ttt   gtc aac aca cta gtc   aat atc atg att gct       6942
Phe Leu Thr Leu Phe   Val Asn Thr Leu Val   Asn Ile Met Ile Ala
        2295                  2300                  2305 agc aga gta cta cgt   gaa cgg tta acc acg   tca gcg tgc gcg gcc       6987
Ser Arg Val Leu Arg   Glu Arg Leu Thr Thr   Ser Ala Cys Ala Ala
        2310                  2315                  2320 tct atc ggc gac gat   aac ata gtg cat ggt   gtc gtc tcc gac acc       7032
Ser Ile Gly Asp Asp   Asn Ile Val His Gly   Val Val Ser Asp Thr
        2325                  2330                  2335 ttg atg gcg gag aga   tgc gcc act tgg ctg   aac atg gaa gta aaa       7077
Leu Met Ala Glu Arg   Cys Ala Thr Trp Leu   Asn Met Glu Val Lys
        2340                  2345                  2350 att att gat gca gtt   att ggt atc aaa gca   ccc tac ttc tgt ggg       7122
Ile Ile Asp Ala Val   Ile Gly Ile Lys Ala   Pro Tyr Phe Cys Gly
        2355                  2360                  2365 gga ttt atc ctg gtg   gac cag ata aca ggc   aca gcc tgc aga gtc       7167
Gly Phe Ile Leu Val   Asp Gln Ile Thr Gly   Thr Ala Cys Arg Val
        2370                  2375                  2380 gca gac cct cta aaa   agg ctt ttt aag ctt   gga aaa cca ttg cca       7212
Ala Asp Pro Leu Lys   Arg Leu Phe Lys Leu   Gly Lys Pro Leu Pro
        2385                  2390                  2395 gtc gat gat acc caa   gac tgc gac cgc cgc   cgg gca ctg cat gat       7257
Val Asp Asp Thr Gln   Asp Cys Asp Arg Arg   Arg Ala Leu His Asp
        2400                  2405                  2410 gaa gca atg cga tgg   aac aga att gga att   acg gac gag tta gtg       7302
Glu Ala Met Arg Trp   Asn Arg Ile Gly Ile   Thr Asp Glu Leu Val
        2415                  2420                  2425 aag gcc gta gaa tcc   aga tac gag atc ata   ctg gca ggc ctg atc       7347
Lys Ala Val Glu Ser   Arg Tyr Glu Ile Ile   Leu Ala Gly Leu Ile
        2430                  2435                  2440 atc acg tct ctg tcc   acg tta gcc gaa agc   gtt aag aac ttc aag       7392
Ile Thr Ser Leu Ser   Thr Leu Ala Glu Ser   Val Lys Asn Phe Lys
        2445                  2450                  2455 agc ata aga ggg agc   cca atc acc ctc tac   ggc tga cctaaatagg        7438
Ser Ile Arg Gly Ser   Pro Ile Thr Leu Tyr   Gly
        2460                  2465 tgacgtagta gacacgcacc tacccaccgg caga atg ttt cca tac  cct cag        7490
                                     Met Phe Pro Tyr  Pro Gln
                                               2470
```

```
ctg aac ttt cca cca gtt tac cct aca aat ccg atg gct tac cga       7535
Leu Asn Phe Pro Pro Val Tyr Pro Thr Asn Pro Met Ala Tyr Arg
            2475              2480              2485 gat cca aac cct cct agg cgc cgc tgg agg ccg ttt cgg ccc ccg       7580
Asp Pro Asn Pro Pro Arg Arg Arg Trp Arg Pro Phe Arg Pro Pro
            2490              2495              2500 ctg gct gct caa atc gaa gat ctt agg agg tcg ata gtc aac ttg       7625
Leu Ala Ala Gln Ile Glu Asp Leu Arg Arg Ser Ile Val Asn Leu
            2505              2510              2515 act ttc aaa caa cga tca cct aat ccg ccg cca ggt cca ccg cca       7670
Thr Phe Lys Gln Arg Ser Pro Asn Pro Pro Pro Gly Pro Pro Pro
            2520              2525              2530 aag aag aag aag agt gct cct aag cca aaa cct act cag cct aaa       7715
Lys Lys Lys Lys Ser Ala Pro Lys Pro Lys Pro Thr Gln Pro Lys
            2535              2540              2545 aag aag aag cag caa gcc aag agg acg aaa cgc aag cct aaa cca       7760
Lys Lys Lys Gln Gln Ala Lys Arg Thr Lys Arg Lys Pro Lys Pro
            2550              2555              2560 ggg aaa cga caa cgt atg tgt atg aag ttg gag tcg gac aag aca       7805
Gly Lys Arg Gln Arg Met Cys Met Lys Leu Glu Ser Asp Lys Thr
            2565              2570              2575 ttt ccg atc atg ctg aac ggc caa gtg aat gga tat gcc tgc gtt       7850
Phe Pro Ile Met Leu Asn Gly Gln Val Asn Gly Tyr Ala Cys Val
            2580              2585              2590 gtc gga gga agg ctg atg aaa cca ctc cac gtt gaa gga aaa att       7895
Val Gly Gly Arg Leu Met Lys Pro Leu His Val Glu Gly Lys Ile
            2595              2600              2605 gat aat gag caa tta gcg gcc gtg aaa ttg aag aag gct agc atg       7940
Asp Asn Glu Gln Leu Ala Ala Val Lys Leu Lys Lys Ala Ser Met
            2610              2615              2620 tac gac ttg gag tac ggc gac gtt ccc cag aac atg aaa tca gac       7985
Tyr Asp Leu Glu Tyr Gly Asp Val Pro Gln Asn Met Lys Ser Asp
            2625              2630              2635 acg ctg cag tac acc agc gac aaa cca ccg ggc ttc tac aac tgg       8030
Thr Leu Gln Tyr Thr Ser Asp Lys Pro Pro Gly Phe Tyr Asn Trp
            2640              2645              2650 cac cac ggc gca gtc cag tat gag aat ggg aga ttt acc gta ccg       8075
His His Gly Ala Val Gln Tyr Glu Asn Gly Arg Phe Thr Val Pro
            2655              2660              2665 aga gga gtg ggc ggg aaa ggc gac agc gga aga ccg atc ctg gac       8120
Arg Gly Val Gly Gly Lys Gly Asp Ser Gly Arg Pro Ile Leu Asp
            2670              2675              2680 aac aga ggc aga gtt gtg gct att gtt cta gga ggt gca aat gag       8165
Asn Arg Gly Arg Val Val Ala Ile Val Leu Gly Gly Ala Asn Glu
            2685              2690              2695 ggc acg cgt acg gcg ctt tca gtg gtc act tgg aac cag aaa ggg       8210
Gly Thr Arg Thr Ala Leu Ser Val Val Thr Trp Asn Gln Lys Gly
            2700              2705              2710 gtg acc att agg gat acc ccc gaa ggt tct gaa ccg tgg tca cta       8255
Val Thr Ile Arg Asp Thr Pro Glu Gly Ser Glu Pro Trp Ser Leu
            2715              2720              2725 gtt aca gcg cta tgc gtg ctt tcg aat gtc acg ttc cca tgc gac       8300
Val Thr Ala Leu Cys Val Leu Ser Asn Val Thr Phe Pro Cys Asp
            2730              2735              2740 aaa cca ccc gtg tgc tat tca ctg acg cca gaa cga acc ctc gac       8345
Lys Pro Pro Val Cys Tyr Ser Leu Thr Pro Glu Arg Thr Leu Asp
            2745              2750              2755 gtg ctc gaa gag aac gtc gac aat cca aat tac gac acg ctg ctg       8390
Val Leu Glu Glu Asn Val Asp Asn Pro Asn Tyr Asp Thr Leu Leu
            2760              2765              2770
```

-continued

| | | | | | | | | | | | | | |
|---|---|---|---|---|---|---|---|---|---|---|---|---|---|
| gag | aac | gtc | ttg | aaa | tgt | cca | tca | cgc | cgg | ccc | aaa | cga | agc att | 8435 |
| Glu | Asn | Val | Leu | Lys | Cys | Pro | Ser | Arg | Arg | Pro | Lys | Arg | Ser Ile |
| | | 2775 | | | | 2780 | | | | 2785 | | | |
| acc | gat | gac | ttc | aca | ctg | acc | agt | ccc | tac | ctg | ggg | ttc | tgc ccg | 8480 |
| Thr | Asp | Asp | Phe | Thr | Leu | Thr | Ser | Pro | Tyr | Leu | Gly | Phe | Cys Pro |
| | 2790 | | | | 2795 | | | | 2800 | | | | |
| tat | tgc | aga | cac | tca | acg | ccg | tgt | ttc | agc | cca | ata | aaa | att gag | 8525 |
| Tyr | Cys | Arg | His | Ser | Thr | Pro | Cys | Phe | Ser | Pro | Ile | Lys | Ile Glu |
| | 2805 | | | | 2810 | | | | 2815 | | | | |
| aac | gtg | tgg | gac | gaa | tct | gat | gat | gga | tcg | att | aga | atc | cag gtc | 8570 |
| Asn | Val | Trp | Asp | Glu | Ser | Asp | Asp | Gly | Ser | Ile | Arg | Ile | Gln Val |
| | 2820 | | | | 2825 | | | | 2830 | | | | |
| tcg | gca | caa | ttc | ggc | tac | aat | cag | gca | ggc | act | gcg | gat | gtc acc | 8615 |
| Ser | Ala | Gln | Phe | Gly | Tyr | Asn | Gln | Ala | Gly | Thr | Ala | Asp | Val Thr |
| | 2835 | | | | 2840 | | | | 2845 | | | | |
| aaa | ttc | cgt | tac | atg | tct | ttc | gac | cac | gac | cat | gac | atc | aag gaa | 8660 |
| Lys | Phe | Arg | Tyr | Met | Ser | Phe | Asp | His | Asp | His | Asp | Ile | Lys Glu |
| | 2850 | | | | 2855 | | | | 2860 | | | | |
| gac | agt | atg | gag | aaa | ata | gct | atc | agc | aca | tct | gga | ccc | tgc cgt | 8705 |
| Asp | Ser | Met | Glu | Lys | Ile | Ala | Ile | Ser | Thr | Ser | Gly | Pro | Cys Arg |
| | 2865 | | | | 2870 | | | | 2875 | | | | |
| cgt | ctt | ggc | cac | aaa | ggg | tac | ttc | ctg | tta | gct | caa | tgt | cct cca | 8750 |
| Arg | Leu | Gly | His | Lys | Gly | Tyr | Phe | Leu | Leu | Ala | Gln | Cys | Pro Pro |
| | 2880 | | | | 2885 | | | | 2890 | | | | |
| ggt | gac | agt | gta | acc | gtc | agt | atc | acg | agc | gga | gca | tct | gag aat | 8795 |
| Gly | Asp | Ser | Val | Thr | Val | Ser | Ile | Thr | Ser | Gly | Ala | Ser | Glu Asn |
| | 2895 | | | | 2900 | | | | 2905 | | | | |
| tca | tgc | acc | gtg | gag | aaa | aag | atc | agg | agg | aag | ttt | gtc | ggt aga | 8840 |
| Ser | Cys | Thr | Val | Glu | Lys | Lys | Ile | Arg | Arg | Lys | Phe | Val | Gly Arg |
| | 2910 | | | | 2915 | | | | 2920 | | | | |
| gag | gag | tac | ttg | ttc | cca | ccc | gtc | cat | gga | aag | ctg | gta | aag tgc | 8885 |
| Glu | Glu | Tyr | Leu | Phe | Pro | Pro | Val | His | Gly | Lys | Leu | Val | Lys Cys |
| | 2925 | | | | 2930 | | | | 2935 | | | | |
| cac | gtt | tac | gat | cac | ttg | aag | gag | acg | tct | gcc | ggg | tac | ata acc | 8930 |
| His | Val | Tyr | Asp | His | Leu | Lys | Glu | Thr | Ser | Ala | Gly | Tyr | Ile Thr |
| | 2940 | | | | 2945 | | | | 2950 | | | | |
| atg | cac | agg | cca | ggc | cca | cac | gcg | tat | aag | tcc | tat | ctg | gag gaa | 8975 |
| Met | His | Arg | Pro | Gly | Pro | His | Ala | Tyr | Lys | Ser | Tyr | Leu | Glu Glu |
| | 2955 | | | | 2960 | | | | 2965 | | | | |
| gcg | tca | ggc | gaa | gtg | tac | att | aaa | cca | cct | tct | ggc | aag | aac gtc | 9020 |
| Ala | Ser | Gly | Glu | Val | Tyr | Ile | Lys | Pro | Pro | Ser | Gly | Lys | Asn Val |
| | 2970 | | | | 2975 | | | | 2980 | | | | |
| acc | tac | gaa | tgt | aag | tgt | ggc | gac | tac | agc | aca | ggt | atc | gtg agc | 9065 |
| Thr | Tyr | Glu | Cys | Lys | Cys | Gly | Asp | Tyr | Ser | Thr | Gly | Ile | Val Ser |
| | 2985 | | | | 2990 | | | | 2995 | | | | |
| acg | cga | acg | aag | atg | aac | ggc | tgc | act | aaa | gca | aaa | cag | tgc att | 9110 |
| Thr | Arg | Thr | Lys | Met | Asn | Gly | Cys | Thr | Lys | Ala | Lys | Gln | Cys Ile |
| | 3000 | | | | 3005 | | | | 3010 | | | | |
| gcc | tac | aag | agc | gac | caa | acg | aaa | tgg | gtc | ttc | aac | tcg | ccg gat | 9155 |
| Ala | Tyr | Lys | Ser | Asp | Gln | Thr | Lys | Trp | Val | Phe | Asn | Ser | Pro Asp |
| | 3015 | | | | 3020 | | | | 3025 | | | | |
| ctt | att | agg | cac | aca | gac | cac | tca | gtg | caa | ggt | aaa | ttg | cac att | 9200 |
| Leu | Ile | Arg | His | Thr | Asp | His | Ser | Val | Gln | Gly | Lys | Leu | His Ile |
| | 3030 | | | | 3035 | | | | 3040 | | | | |
| cca | ttc | cgc | ttg | aca | ccg | aca | gtc | tgc | ccg | gtt | ccg | tta | gct cac | 9245 |
| Pro | Phe | Arg | Leu | Thr | Pro | Thr | Val | Cys | Pro | Val | Pro | Leu | Ala His |
| | 3045 | | | | 3050 | | | | 3055 | | | | |
| acg | cct | aca | gtc | acg | aag | tgg | ttc | aaa | ggc | atc | acc | ctc | cac ctg | 9290 |
| Thr | Pro | Thr | Val | Thr | Lys | Trp | Phe | Lys | Gly | Ile | Thr | Leu | His Leu |

-continued

|  |  |  |  |  |  |  |  |  |  |  |  |  |
|---|---|---|---|---|---|---|---|---|---|---|---|---|
|  | 3060 |  |  | 3065 |  |  |  | 3070 |  |  |  |  |
| act | gca | atg | cga | cca | aca | ttg | ctg | aca | acg | aga | aaa | ttg | ggg | ctg | 9335 |
| Thr | Ala | Met | Arg | Pro | Thr | Leu | Leu | Thr | Thr | Arg | Lys | Leu | Gly | Leu |  |
|  | 3075 |  |  |  | 3080 |  |  |  |  | 3085 |  |  |  |  |
| cga | gca | gac | gca | aca | gca | gaa | tgg | att | aca | ggg | tct | aca | tcc | agg | 9380 |
| Arg | Ala | Asp | Ala | Thr | Ala | Glu | Trp | Ile | Thr | Gly | Ser | Thr | Ser | Arg |  |
| 3090 |  |  |  |  | 3095 |  |  |  |  | 3100 |  |  |  |  |
| aat | ttt | tct | gtg | ggg | cga | gaa | ggg | ctg | gag | tac | gta | tgg | ggt | aac | 9425 |
| Asn | Phe | Ser | Val | Gly | Arg | Glu | Gly | Leu | Glu | Tyr | Val | Trp | Gly | Asn |  |
| 3105 |  |  |  |  | 3110 |  |  |  |  | 3115 |  |  |  |  |
| cat | gaa | cca | gtc | aga | gtc | tgg | gcc | cag | gag | tcg | gca | cca | ggc | gac | 9470 |
| His | Glu | Pro | Val | Arg | Val | Trp | Ala | Gln | Glu | Ser | Ala | Pro | Gly | Asp |  |
| 3120 |  |  |  |  | 3125 |  |  |  |  | 3130 |  |  |  |  |
| cca | cat | gga | tgg | ccg | cat | gag | atc | atc | atc | cac | tat | tat | cat | cgg | 9515 |
| Pro | His | Gly | Trp | Pro | His | Glu | Ile | Ile | Ile | His | Tyr | Tyr | His | Arg |  |
| 3135 |  |  |  |  | 3140 |  |  |  |  | 3145 |  |  |  |  |
| cat | cca | gtc | tac | act | gtc | att | gtg | ctg | tgt | ggt | gtc | gct | ctt | gct | 9560 |
| His | Pro | Val | Tyr | Thr | Val | Ile | Val | Leu | Cys | Gly | Val | Ala | Leu | Ala |  |
| 3150 |  |  |  |  | 3155 |  |  |  |  | 3160 |  |  |  |  |
| atc | ctg | gta | ggc | act | gca | tca | tca | gca | gct | tgc | atc | gcc | aaa | gca | 9605 |
| Ile | Leu | Val | Gly | Thr | Ala | Ser | Ser | Ala | Ala | Cys | Ile | Ala | Lys | Ala |  |
| 3165 |  |  |  |  | 3170 |  |  |  |  | 3175 |  |  |  |  |
| aga | aga | gac | tgc | ctg | acg | cca | tac | gcg | ctt | gca | ccg | aac | gca | acg | 9650 |
| Arg | Arg | Asp | Cys | Leu | Thr | Pro | Tyr | Ala | Leu | Ala | Pro | Asn | Ala | Thr |  |
| 3180 |  |  |  |  | 3185 |  |  |  |  | 3190 |  |  |  |  |
| gta | ccc | aca | gca | tta | gcg | gtt | ttg | tgc | tgc | att | cgg | cca | acc | aac | 9695 |
| Val | Pro | Thr | Ala | Leu | Ala | Val | Leu | Cys | Cys | Ile | Arg | Pro | Thr | Asn |  |
| 3195 |  |  |  |  | 3200 |  |  |  |  | 3205 |  |  |  |  |
| gct | gaa | aca | ttt | gga | gaa | act | ttg | aac | cat | ctg | tgg | ttt | aac | aac | 9740 |
| Ala | Glu | Thr | Phe | Gly | Glu | Thr | Leu | Asn | His | Leu | Trp | Phe | Asn | Asn |  |
| 3210 |  |  |  |  | 3215 |  |  |  |  | 3220 |  |  |  |  |
| caa | ccg | ttt | ctc | tgg | gca | cag | ttg | tgc | att | cct | ctg | gca | gcg | ctt | 9785 |
| Gln | Pro | Phe | Leu | Trp | Ala | Gln | Leu | Cys | Ile | Pro | Leu | Ala | Ala | Leu |  |
| 3225 |  |  |  |  | 3230 |  |  |  |  | 3235 |  |  |  |  |
| gtt | att | ctg | ttc | cgc | tgc | ttt | tca | tgc | tgc | atg | cct | ttt | tta | ttg | 9830 |
| Val | Ile | Leu | Phe | Arg | Cys | Phe | Ser | Cys | Cys | Met | Pro | Phe | Leu | Leu |  |
| 3240 |  |  |  |  | 3245 |  |  |  |  | 3250 |  |  |  |  |
| gtt | gca | ggc | gtc | tgc | ctg | ggg | aag | gta | gac | gcc | ttc | gaa | cat | gcg | 9875 |
| Val | Ala | Gly | Val | Cys | Leu | Gly | Lys | Val | Asp | Ala | Phe | Glu | His | Ala |  |
| 3255 |  |  |  |  | 3260 |  |  |  |  | 3265 |  |  |  |  |
| acc | act | gtg | cca | aat | gtt | ccg | ggg | atc | ccg | tat | aag | gcg | ttg | gtc | 9920 |
| Thr | Thr | Val | Pro | Asn | Val | Pro | Gly | Ile | Pro | Tyr | Lys | Ala | Leu | Val |  |
| 3270 |  |  |  |  | 3275 |  |  |  |  | 3280 |  |  |  |  |
| gaa | cgc | gca | ggt | tac | gcg | cca | ctt | aac | ctg | gag | atc | acg | gtc | gtc | 9965 |
| Glu | Arg | Ala | Gly | Tyr | Ala | Pro | Leu | Asn | Leu | Glu | Ile | Thr | Val | Val |  |
| 3285 |  |  |  |  | 3290 |  |  |  |  | 3295 |  |  |  |  |
| tca | tcg | gaa | tta | aca | cct | tca | act | aac | aag | gag | tac | gtg | acc | tgc | 10010 |
| Ser | Ser | Glu | Leu | Thr | Pro | Ser | Thr | Asn | Lys | Glu | Tyr | Val | Thr | Cys |  |
| 3300 |  |  |  |  | 3305 |  |  |  |  | 3310 |  |  |  |  |
| aaa | ttc | cac | aca | gtc | att | cct | tca | cca | caa | gtt | aaa | tgc | tgc | ggg | 10055 |
| Lys | Phe | His | Thr | Val | Ile | Pro | Ser | Pro | Gln | Val | Lys | Cys | Cys | Gly |  |
| 3315 |  |  |  |  | 3320 |  |  |  |  | 3325 |  |  |  |  |
| tcc | ctc | gag | tgc | aag | gca | tcc | tca | aag | gcg | gat | tac | aca | tgc | cgc | 10100 |
| Ser | Leu | Glu | Cys | Lys | Ala | Ser | Ser | Lys | Ala | Asp | Tyr | Thr | Cys | Arg |  |
| 3330 |  |  |  |  | 3335 |  |  |  |  | 3340 |  |  |  |  |
| gtt | ttt | ggc | ggt | gtg | tac | cct | ttc | atg | tgg | gga | ggc | gca | caa | tgc | 10145 |
| Val | Phe | Gly | Gly | Val | Tyr | Pro | Phe | Met | Trp | Gly | Gly | Ala | Gln | Cys |  |
| 3345 |  |  |  |  | 3350 |  |  |  |  | 3355 |  |  |  |  |
| ttc | tgt | gac | agt | gag | aac | aca | caa | ctg | agt | gag | gcg | tac | gtc | gag | 10190 |

```
                                    -continued

Phe Cys Asp Ser Glu Asn Thr Gln Leu Ser Glu Ala Tyr Val Glu
        3360            3365            3370 ttc gct cca gac tgc act ata gat cac gca gtc gca cta aaa gtt       10235
Phe Ala Pro Asp Cys Thr Ile Asp His Ala Val Ala Leu Lys Val
        3375            3380            3385 cac aca gct gct ctg aaa gtc ggc ctg cgt ata gta tac ggc aac       10280
His Thr Ala Ala Leu Lys Val Gly Leu Arg Ile Val Tyr Gly Asn
        3390            3395            3400 acc acc gcg cac ctg gat acg ttt gtc aat ggc gtc acg cca ggt       10325
Thr Thr Ala His Leu Asp Thr Phe Val Asn Gly Val Thr Pro Gly
        3405            3410            3415 tcc tca cgg gac ctg aag gtc ata gca ggg ccg ata tca gcc gct       10370
Ser Ser Arg Asp Leu Lys Val Ile Ala Gly Pro Ile Ser Ala Ala
        3420            3425            3430 ttt tca ccc ttt gac cat aag gtc gtc atc aga aag ggg ctt gtt       10415
Phe Ser Pro Phe Asp His Lys Val Val Ile Arg Lys Gly Leu Val
        3435            3440            3445 tac aac tac gac ttc cct gag tat gga gct atg aaa cca gga gcg       10460
Tyr Asn Tyr Asp Phe Pro Glu Tyr Gly Ala Met Lys Pro Gly Ala
        3450            3455            3460 ttc ggc gat att caa gca tcc tcg ctt gat gct aca gac ata gta       10505
Phe Gly Asp Ile Gln Ala Ser Ser Leu Asp Ala Thr Asp Ile Val
        3465            3470            3475 gcc cgc act gac ata cgg ctg ctg aag cct tct gtc aag aac atc       10550
Ala Arg Thr Asp Ile Arg Leu Leu Lys Pro Ser Val Lys Asn Ile
        3480            3485            3490 cac gtc ccc tac acc caa gca gta tca ggg tat gaa atg tgg aag       10595
His Val Pro Tyr Thr Gln Ala Val Ser Gly Tyr Glu Met Trp Lys
        3495            3500            3505 aac aac tca gga cga ccc ctg caa gaa aca gca cca ttt gga tgt       10640
Asn Asn Ser Gly Arg Pro Leu Gln Glu Thr Ala Pro Phe Gly Cys
        3510            3515            3520 aaa att gaa gtg gag cct ctg cga gcg tct aac tgt gct tac ggg       10685
Lys Ile Glu Val Glu Pro Leu Arg Ala Ser Asn Cys Ala Tyr Gly
        3525            3530            3535 cac atc cct atc tcg att gac atc cct gat gca gct ttt gtg aga       10730
His Ile Pro Ile Ser Ile Asp Ile Pro Asp Ala Ala Phe Val Arg
        3540            3545            3550 tca tca gaa tca cca aca att tta gaa gtt agc tgc aca gta gca       10775
Ser Ser Glu Ser Pro Thr Ile Leu Glu Val Ser Cys Thr Val Ala
        3555            3560            3565 gac tgc att tat tct gca gac ttt ggt ggt tct cta aca tta cag       10820
Asp Cys Ile Tyr Ser Ala Asp Phe Gly Gly Ser Leu Thr Leu Gln
        3570            3575            3580 tac aaa gct gac agg gag gga cat tgt cca gtt cac tcc cac tcc       10865
Tyr Lys Ala Asp Arg Glu Gly His Cys Pro Val His Ser His Ser
        3585            3590            3595 acg aca gct gtt ttg aag gaa gcg acc aca cat gtg act gcc gta       10910
Thr Thr Ala Val Leu Lys Glu Ala Thr Thr His Val Thr Ala Val
        3600            3605            3610 ggc agc ata aca cta cat ttt agc aca tcg agc cca caa gca aat       10955
Gly Ser Ile Thr Leu His Phe Ser Thr Ser Ser Pro Gln Ala Asn
        3615            3620            3625 ttt ata gtt tcg cta tgc ggc aag aag tcc acc tgc aat gct gaa       11000
Phe Ile Val Ser Leu Cys Gly Lys Lys Ser Thr Cys Asn Ala Glu
        3630            3635            3640 tgt aaa cca ccg gcc gac cac ata att gga gaa cca cat aaa gtc       11045
Cys Lys Pro Pro Ala Asp His Ile Ile Gly Glu Pro His Lys Val
        3645            3650            3655
```

-continued

| | | | | | | | | | | |
|---|---|---|---|---|---|---|---|---|---|---|
| gac | caa | gaa | ttc | cag | gcg | gca | gtt | tcc | aaa | aca tct tgg aac tgg | 11090 |
| Asp | Gln | Glu | Phe | Gln | Ala | Ala | Val | Ser | Lys | Thr Ser Trp Asn Trp | |
| | | 3660 | | | | 3665 | | | | 3670 | |

| | | | | | | | | | | |
|---|---|---|---|---|---|---|---|---|---|---|
| ctg | ctt | gca | ctg | ttt | ggg | gga | gca | tca | tcc | ctc att gtt gta gga | 11135 |
| Leu | Leu | Ala | Leu | Phe | Gly | Gly | Ala | Ser | Ser | Leu Ile Val Val Gly | |
| | | 3675 | | | | 3680 | | | | 3685 | |

| | | | | | | | | | | |
|---|---|---|---|---|---|---|---|---|---|---|
| ctt | ata | gtg | ttg | gtc | tgc | agc | tct | atg | ctt | ata aac aca cgt aga | 11180 |
| Leu | Ile | Val | Leu | Val | Cys | Ser | Ser | Met | Leu | Ile Asn Thr Arg Arg | |
| | | 3690 | | | | 3695 | | | | 3700 | | tga ctgagcgcgg acactgacat agcggtaaaa ctcgatgtac ttccgaggaa 11233 gcgtggtgca taatgccacg cgccgcttga cactaaaact cgatgtattt ccgaggaagc 11293 acagtgcata atgctgtgca gtgtcacatt aatcgtatat cacactacat attaacaaca 11353 ctatatcact tttatgagac tcactatggg tctctaatat acactacaca tattttactt 11413 aaaaacacta tacacacttt ataaattctt ttataatttt tcttttgttt ttattttgtt 11473 tttaaaattt c 11484

<210> SEQ ID NO 2
<211> LENGTH: 1852
<212> TYPE: PRT
<213> ORGANISM: Western equine encephalomyelitis virus - strain 71V-1658

<400> SEQUENCE: 2

Met Glu Arg Ile His Val Asp Leu Asp Ala Asp Ser Pro Tyr Val Lys
1               5                   10                  15

Ser Leu Gln Arg Thr Phe Pro Gln Phe Glu Ile Glu Ala Arg Gln Val
            20                  25                  30

Thr Asp Asn Asp His Ala Asn Ala Arg Ala Phe Ser His Val Ala Thr
        35                  40                  45

Lys Leu Ile Glu Ser Glu Val Asp Arg Asp Gln Val Ile Leu Asp Ile
    50                  55                  60

Gly Ser Ala Pro Val Arg His Ala His Ser Asn His Arg Tyr His Cys
65                  70                  75                  80

Ile Cys Pro Met Ile Ser Ala Glu Asp Pro Asp Arg Leu Gln Arg Tyr
                85                  90                  95

Ala Glu Arg Leu Lys Lys Ser Asp Ile Thr Asp Lys Asn Ile Ala Ser
            100                 105                 110

Lys Ala Ala Asp Leu Leu Glu Val Met Ser Thr Pro Asp Ala Glu Thr
        115                 120                 125

Pro Ser Leu Cys Met His Thr Asp Ala Thr Cys Arg Tyr Phe Gly Ser
    130                 135                 140

Val Ala Val Tyr Gln Asp Val Tyr Ala Val His Ala Pro Thr Ser Ile
145                 150                 155                 160

Tyr His Gln Ala Leu Lys Gly Val Arg Thr Ile Tyr Trp Ile Gly Phe
                165                 170                 175

Asp Thr Thr Pro Phe Met Tyr Lys Asn Met Ala Gly Ser Tyr Pro Thr
            180                 185                 190

Tyr Asn Thr Asn Trp Ala Asp Glu Arg Val Leu Glu Ala Arg Asn Ile
        195                 200                 205

Gly Leu Gly Asn Ser Asp Leu Gln Glu Ser Arg Leu Gly Lys Leu Ser
    210                 215                 220

Ile Leu Arg Lys Lys Arg Leu Gln Pro Thr Asn Lys Ile Ile Phe Ser
225                 230                 235                 240

Val Gly Ser Thr Ile Tyr Thr Glu Asp Arg Ser Leu Leu Arg Ser Trp
                245                 250                 255

-continued

His Leu Pro Asn Val Phe His Leu Lys Gly Lys Ser Asn Phe Thr Gly
                260                 265                 270

Arg Cys Gly Thr Ile Val Ser Cys Glu Gly Tyr Val Ile Lys Lys Ile
            275                 280                 285

Thr Ile Ser Pro Gly Leu Tyr Gly Lys Val Glu Asn Leu Ala Ser Thr
        290                 295                 300

Met His Arg Glu Gly Phe Leu Ser Cys Lys Val Thr Asp Thr Leu Arg
305                 310                 315                 320

Gly Glu Arg Val Ser Phe Ala Val Cys Thr Tyr Val Pro Ala Thr Leu
                325                 330                 335

Cys Asp Gln Met Thr Gly Ile Leu Ala Thr Asp Val Ser Val Asp Asp
            340                 345                 350

Ala Gln Lys Leu Leu Val Gly Leu Asn Gln Arg Ile Val Val Asn Gly
        355                 360                 365

Arg Thr Gln Arg Asn Thr Asn Thr Met Gln Asn Tyr Leu Leu Pro Val
370                 375                 380

Val Ala Gln Ala Phe Ser Arg Trp Ala Arg Glu His Arg Ala Asp Leu
385                 390                 395                 400

Asp Asp Glu Lys Glu Leu Gly Val Arg Glu Arg Thr Leu Thr Met Gly
                405                 410                 415

Cys Cys Trp Ala Phe Lys Thr Gln Lys Ile Thr Ser Ile Tyr Lys Lys
            420                 425                 430

Pro Gly Thr Gln Thr Ile Lys Lys Val Pro Ala Val Phe Asp Ser Phe
        435                 440                 445

Val Ile Pro Arg Leu Thr Ser His Gly Leu Asp Met Gly Phe Arg Arg
450                 455                 460

Arg Leu Lys Leu Leu Leu Glu Pro Thr Val Lys Pro Ala Pro Ala Ile
465                 470                 475                 480

Thr Met Ala Asp Val Glu His Leu Arg Gly Leu Gln Gln Glu Ala Glu
                485                 490                 495

Glu Val Ala Ala Ala Glu Glu Ile Arg Glu Ala Leu Pro Pro Leu Leu
            500                 505                 510

Pro Glu Ile Glu Lys Glu Thr Val Glu Ala Glu Val Asp Leu Ile Met
        515                 520                 525

Gln Glu Ala Gly Ala Gly Ser Val Glu Thr Pro Arg Gly His Ile Arg
530                 535                 540

Val Thr Ser Tyr Pro Gly Glu Glu Lys Ile Gly Ser Tyr Ala Ile Leu
545                 550                 555                 560

Ser Pro Gln Ala Val Leu Asn Ser Glu Lys Leu Ala Cys Ile His Pro
                565                 570                 575

Leu Ala Glu Gln Val Leu Val Met Thr His Lys Gly Arg Ala Gly Arg
            580                 585                 590

Tyr Lys Val Glu Pro Tyr His Gly Lys Val Ile Val Pro Glu Gly Thr
        595                 600                 605

Ala Val Pro Val Gln Asp Phe Gln Ala Leu Ser Glu Ser Ala Thr Ile
610                 615                 620

Val Phe Asn Glu Arg Glu Phe Val Asn Arg Tyr Leu His His Ile Ala
625                 630                 635                 640

Ile Asn Gly Gly Ala Leu Asn Thr Asp Glu Glu Tyr Tyr Lys Thr Val
                645                 650                 655

Lys Thr Gln Asp Thr Asp Ser Glu Tyr Val Phe Asp Ile Asp Ala Arg
            660                 665                 670

-continued

Lys Cys Val Lys Arg Glu Asp Ala Gly Pro Leu Cys Leu Thr Gly Asp
        675                 680                 685

Leu Val Asp Pro Pro Phe His Glu Phe Ala Tyr Glu Ser Leu Lys Thr
        690                 695                 700

Arg Pro Ala Ala Pro His Lys Val Pro Thr Ile Gly Val Tyr Gly Val
705                 710                 715                 720

Pro Gly Ser Gly Lys Ser Gly Ile Ile Lys Ser Ala Val Thr Lys Lys
                725                 730                 735

Asp Leu Val Val Ser Ala Lys Lys Glu Asn Cys Ala Glu Ile Ile Arg
            740                 745                 750

Asp Val Arg Arg Met Arg Arg Met Asp Val Ala Ala Arg Thr Val Asp
        755                 760                 765

Ser Val Leu Leu Asn Gly Val Lys His Pro Val Asn Thr Leu Tyr Ile
770                 775                 780

Asp Glu Ala Phe Ala Cys His Ala Gly Thr Leu Leu Ala Leu Ile Ala
785                 790                 795                 800

Ile Val Lys Pro Lys Lys Val Val Leu Cys Gly Asp Pro Lys Gln Cys
                805                 810                 815

Gly Phe Phe Asn Met Met Cys Leu Lys Val His Phe Asn His Asp Ile
                820                 825                 830

Cys Thr Glu Val Tyr His Lys Ser Ile Ser Arg Arg Cys Thr Gln Thr
        835                 840                 845

Val Thr Ala Ile Val Ser Thr Leu Phe Tyr Asp Lys Arg Met Lys Thr
        850                 855                 860

Val Asn Pro Cys Ala Asp Lys Ile Ile Ile Asp Thr Thr Gly Thr Thr
865                 870                 875                 880

Lys Pro His Lys Asp Asp Leu Ile Leu Thr Cys Phe Arg Gly Trp Val
                885                 890                 895

Lys Gln Leu Gln Ile Asp Tyr Lys Asn His Glu Ile Met Thr Ala Ala
            900                 905                 910

Ala Ser Gln Gly Leu Thr Arg Lys Gly Val Tyr Ala Val Arg Tyr Lys
        915                 920                 925

Val Asn Glu Asn Pro Leu Tyr Ser Gln Thr Ser Glu His Val Asn Val
        930                 935                 940

Leu Leu Thr Arg Thr Glu Lys Arg Ile Val Trp Lys Thr Leu Ala Gly
945                 950                 955                 960

Asp Pro Trp Ile Lys Thr Leu Thr Ala Lys Tyr Pro Gly Asp Phe Thr
                965                 970                 975

Ala Ser Leu Asp Asp Trp Gln Arg Glu His Asp Ala Ile Met Ala Arg
            980                 985                 990

Val Leu Asp Lys Pro Gln Thr Ala Asp Val Phe Gln Asn Lys Val Asn
        995                 1000                1005

Val Cys Trp Ala Lys Ala Leu Glu Pro Val Leu Ala Thr Ala Asn
        1010                1015                1020

Ile Val Leu Thr Arg Gln Gln Trp Glu Thr Leu His Pro Phe Lys
        1025                1030                1035

His Asp Arg Ala Tyr Ser Pro Glu Met Ala Leu Asn Phe Phe Cys
        1040                1045                1050

Thr Arg Phe Phe Gly Val Asp Leu Asp Ser Gly Leu Phe Ser Ala
        1055                1060                1065

Pro Thr Val Ala Leu Thr Tyr Arg Asp Gln His Trp Asp Asn Ser
        1070                1075                1080

Pro Gly Lys Asn Met Tyr Gly Leu Asn Arg Glu Val Ala Lys Glu

-continued

```
            1085                1090                1095

Leu Ser Arg Arg Tyr Pro Cys Ile Thr Lys Ala Val Asp Thr Gly
    1100                1105                1110

Arg Val Ala Asp Ile Arg Asn Asn Thr Ile Lys Asp Tyr Ser Pro
    1115                1120                1125

Thr Ile Asn Val Val Pro Leu Asn Arg Arg Leu Pro His Ser Leu
    1130                1135                1140

Ile Val Asp His Lys Gly Gln Gly Thr Thr Asp His Ser Gly Phe
    1145                1150                1155

Leu Ser Lys Met Lys Gly Lys Ser Val Leu Val Ile Gly Asp Pro
    1160                1165                1170

Ile Ser Ile Pro Gly Lys Lys Val Glu Ser Met Gly Pro Leu Pro
    1175                1180                1185

Thr Asn Thr Ile Arg Cys Asp Leu Asp Leu Gly Ile Pro Ser His
    1190                1195                1200

Val Gly Lys Tyr Asp Ile Ile Phe Val Asn Val Arg Thr Pro Tyr
    1205                1210                1215

Arg Asn His His Tyr Gln Gln Cys Glu Asp His Ala Ile His His
    1220                1225                1230

Ser Met Leu Thr Cys Lys Ala Val His His Leu Asn Thr Gly Gly
    1235                1240                1245

Thr Cys Val Ala Ile Gly Tyr Gly Leu Ala Asp Arg Ala Thr Glu
    1250                1255                1260

Asn Ile Ile Thr Ala Val Ala Arg Ser Phe Arg Phe Thr Arg Val
    1265                1270                1275

Cys Gln Pro Lys Asn Thr Ala Glu Asn Thr Glu Val Leu Phe Val
    1280                1285                1290

Phe Phe Gly Lys Asp Asn Gly Asn His Thr His Asp Gln Asp Arg
    1295                1300                1305

Leu Gly Val Val Leu Asp Asn Ile Tyr Gln Gly Ser Thr Arg Tyr
    1310                1315                1320

Glu Ala Gly Arg Ala Pro Ala Tyr Arg Val Ile Arg Gly Asp Ile
    1325                1330                1335

Ser Lys Ser Ala Asp Gln Ala Ile Val Asn Ala Ala Asn Ser Lys
    1340                1345                1350

Gly Gln Pro Gly Ser Gly Val Cys Gly Ala Leu Tyr Arg Lys Trp
    1355                1360                1365

Pro Ala Ala Phe Asp Arg Gln Pro Ile Ala Val Gly Thr Ala Arg
    1370                1375                1380

Leu Val Lys His Glu Pro Leu Ile Ile His Ala Val Gly Pro Asn
    1385                1390                1395

Phe Ser Lys Met Pro Glu Pro Glu Gly Asp Leu Lys Leu Ala Ala
    1400                1405                1410

Ala Tyr Met Ser Ile Ala Ser Ile Val Asn Ala Glu Arg Ile Thr
    1415                1420                1425

Lys Ile Ser Val Pro Leu Leu Ser Thr Gly Ile Tyr Ser Gly Gly
    1430                1435                1440

Lys Asp Arg Val Met Gln Ser Leu His His Leu Phe Thr Ala Phe
    1445                1450                1455

Asp Thr Thr Asp Ala Asp Val Thr Ile Tyr Cys Leu Asp Lys Gln
    1460                1465                1470

Trp Glu Thr Arg Ile Ile Glu Ala Ile His Arg Lys Glu Ser Val
    1475                1480                1485
```

-continued

```
Glu Ile Leu Asp Asp Lys Pro Val Asp Ile Asp Leu Val Arg
    1490            1495            1500

Val His Pro Asn Ser Ser Leu Ala Gly Arg Pro Gly Tyr Ser Val
    1505            1510            1515

Asn Glu Gly Lys Leu Tyr Ser Tyr Leu Glu Gly Thr Arg Phe His
    1520            1525            1530

Gln Thr Ala Lys Asp Ile Ala Glu Ile His Ala Met Trp Pro Asn
    1535            1540            1545

Lys Ser Glu Ala Asn Glu Gln Ile Cys Leu Tyr Ile Leu Gly Glu
    1550            1555            1560

Ser Met Ser Ser Ile Arg Ser Lys Cys Pro Val Glu Glu Ser Glu
    1565            1570            1575

Ala Ser Ala Pro Pro His Thr Leu Pro Cys Leu Cys Asn Tyr Ala
    1580            1585            1590

Met Thr Ala Glu Arg Val Tyr Arg Leu Arg Ser Ala Lys Lys Glu
    1595            1600            1605

Gln Phe Ala Val Cys Ser Ser Phe Leu Leu Pro Lys Tyr Arg Ile
    1610            1615            1620

Thr Gly Val Gln Lys Leu Gln Cys Ser Lys Pro Val Leu Phe Ser
    1625            1630            1635

Gly Val Val Pro Pro Ala Val His Pro Arg Lys Tyr Ala Glu Ile
    1640            1645            1650

Ile Leu Glu Thr Pro Pro Pro Ala Thr Thr Thr Val Ile Cys
    1655            1660            1665

Glu Pro Thr Val Pro Glu Arg Ile Pro Ser Pro Val Ile Ser Arg
    1670            1675            1680

Ala Pro Ser Ala Glu Ser Leu Leu Ser Leu Gly Gly Val Ser Phe
    1685            1690            1695

Ser Ser Ser Ala Thr Arg Ser Ser Thr Ala Trp Ser Asp Tyr Asp
    1700            1705            1710

Arg Arg Phe Val Val Thr Ala Asp Val His Gln Ala Asn Thr Ser
    1715            1720            1725

Thr Trp Ser Ile Pro Ser Ala Pro Gly Leu Asp Val Gln Leu Pro
    1730            1735            1740

Ser Asp Val Thr Asp Ser His Trp Ser Ile Pro Ser Ala Ser Gly
    1745            1750            1755

Phe Glu Val Arg Thr Pro Ser Val Gln Asp Leu Thr Ala Glu Cys
    1760            1765            1770

Ala Lys Pro Arg Gly Leu Ala Glu Ile Met Gln Asp Phe Asn Thr
    1775            1780            1785

Ala Pro Phe Gln Phe Leu Ser Asp Tyr Arg Pro Val Pro Ala Pro
    1790            1795            1800

Arg Arg Arg Pro Ile Pro Ser Pro Arg Ser Thr Ala Ser Ala Pro
    1805            1810            1815

Pro Val Pro Lys Pro Arg Arg Thr Lys Tyr Gln Gln Pro Pro Gly
    1820            1825            1830

Val Ala Arg Ala Ile Ser Glu Ala Glu Leu Asp Glu Tyr Ile Arg
    1835            1840            1845

Gln His Ser Asn
    1850

<210> SEQ ID NO 3
<211> LENGTH: 614
```

<212> TYPE: PRT
<213> ORGANISM: Western equine encephalomyelitis virus - strain 71V-1658

<400> SEQUENCE: 3

```
Arg Tyr Glu Ala Gly Ala Tyr Ile Phe Ser Ser Glu Thr Gly Gln Gly
1               5                   10                  15

His Leu Gln Gln Lys Ser Val Arg Gln Cys Lys Leu Gln Glu Pro Ile
            20                  25                  30

Leu Asp Arg Ala Val His Glu Lys Tyr Tyr Ala Pro Arg Leu Asp Leu
        35                  40                  45

Glu Arg Glu Lys Met Leu Gln Lys Lys Leu Gln Leu Cys Ala Ser Glu
    50                  55                  60

Gly Asn Arg Ser Arg Tyr Gln Ser Arg Lys Val Glu Asn Met Lys Ala
65                  70                  75                  80

Ile Thr Ala Glu Arg Leu Ile Ser Gly Leu Gly Thr Tyr Leu Ser Ser
                85                  90                  95

Glu Val Asn Pro Val Glu Cys Tyr Arg Val Asn Tyr Pro Val Pro Ile
            100                 105                 110

Tyr Ser Ser Thr Val Ile Asn Arg Phe Thr Ser Ala Glu Val Ala Val
        115                 120                 125

Lys Thr Cys Asn Leu Val Ile Gln Glu Asn Tyr Pro Thr Val Ala Ser
    130                 135                 140

Tyr Cys Ile Thr Asp Glu Tyr Asp Ala Tyr Leu Asp Met Val Asp Gly
145                 150                 155                 160

Ala Ser Cys Cys Leu Asp Thr Ala Thr Phe Cys Pro Ala Lys Leu Arg
                165                 170                 175

Ser Tyr Pro Lys Lys His Ser Tyr Leu Gln Pro Glu Ile Arg Ser Ala
            180                 185                 190

Val Pro Ser Pro Ile Gln Asn Thr Leu Gln Asn Val Leu Ala Ala Ala
        195                 200                 205

Thr Lys Arg Asn Cys Asn Val Thr Gln Met Arg Glu Leu Pro Val Leu
    210                 215                 220

Asp Ser Ala Ala Phe Asn Val Asp Cys Phe Lys Lys Tyr Ala Cys Asn
225                 230                 235                 240

Asp Glu Tyr Trp Asp Thr Phe Arg Asp Asn Pro Ile Arg Leu Thr Thr
                245                 250                 255

Glu Asn Val Thr Gln Tyr Val Thr Lys Leu Lys Gly Pro Lys Ala Ala
            260                 265                 270

Ala Leu Phe Ala Asn Thr His Asn Leu Lys Pro Leu Gln Glu Ile Pro
        275                 280                 285

Met Asp Gln Phe Val Met Asp Leu Lys Arg Asp Val Lys Val Thr Pro
    290                 295                 300

Gly Thr Lys His Thr Glu Glu Arg Pro Lys Val Gln Val Ile Gln Ala
305                 310                 315                 320

Ala Asp Pro Leu Ala Thr Ala Tyr Leu Cys Gly Ile His Arg Glu Leu
                325                 330                 335

Val Arg Arg Leu Asn Ala Val Leu Leu Pro Asn Ile His Thr Leu Phe
            340                 345                 350

Asp Met Ser Ala Glu Asp Phe Asp Ala Ile Ile Ala Glu His Phe His
        355                 360                 365

His Gly Asp Pro Val Leu Glu Thr Asp Ile Ala Ser Phe Asp Lys Ser
    370                 375                 380

Glu Asp Asp Ala Ile Ala Ile Ser Ala Leu Met Ile Leu Glu Asp Leu
385                 390                 395                 400
```

```
Gly Val Asp Gln Pro Leu Leu Asp Leu Ile Glu Ala Ala Phe Gly Asn
                405                 410                 415

Ile Thr Ser Val His Leu Pro Thr Gly Thr Arg Phe Lys Phe Gly Ala
            420                 425                 430

Met Met Lys Ser Gly Met Phe Leu Thr Leu Phe Val Asn Thr Leu Val
        435                 440                 445

Asn Ile Met Ile Ala Ser Arg Val Leu Arg Glu Arg Leu Thr Thr Ser
    450                 455                 460

Ala Cys Ala Ala Ser Ile Gly Asp Asp Asn Ile Val His Gly Val Val
465                 470                 475                 480

Ser Asp Thr Leu Met Ala Glu Arg Cys Ala Thr Trp Leu Asn Met Glu
                485                 490                 495

Val Lys Ile Ile Asp Ala Val Ile Gly Ile Lys Ala Pro Tyr Phe Cys
            500                 505                 510

Gly Gly Phe Ile Leu Val Asp Gln Ile Thr Gly Thr Ala Cys Arg Val
        515                 520                 525

Ala Asp Pro Leu Lys Arg Leu Phe Lys Leu Gly Lys Pro Leu Pro Val
    530                 535                 540

Asp Asp Thr Gln Asp Cys Asp Arg Arg Arg Ala Leu His Asp Glu Ala
545                 550                 555                 560

Met Arg Trp Asn Arg Ile Gly Ile Thr Asp Glu Leu Val Lys Ala Val
                565                 570                 575

Glu Ser Arg Tyr Glu Ile Ile Leu Ala Gly Leu Ile Ile Thr Ser Leu
            580                 585                 590

Ser Thr Leu Ala Glu Ser Val Lys Asn Phe Lys Ser Ile Arg Gly Ser
        595                 600                 605

Pro Ile Thr Leu Tyr Gly
    610

<210> SEQ ID NO 4
<211> LENGTH: 1236
<212> TYPE: PRT
<213> ORGANISM: Western equine encephalomyelitis virus - strain 71V-1658

<400> SEQUENCE: 4

Met Phe Pro Tyr Pro Gln Leu Asn Phe Pro Pro Val Tyr Pro Thr Asn
1               5                   10                  15

Pro Met Ala Tyr Arg Asp Pro Asn Pro Pro Arg Arg Arg Trp Arg Pro
            20                  25                  30

Phe Arg Pro Pro Leu Ala Ala Gln Ile Glu Asp Leu Arg Arg Ser Ile
        35                  40                  45

Val Asn Leu Thr Phe Lys Gln Arg Ser Pro Asn Pro Pro Gly Pro
    50                  55                  60

Pro Pro Lys Lys Lys Lys Ser Ala Pro Lys Pro Lys Pro Thr Gln Pro
65                  70                  75                  80

Lys Lys Lys Lys Gln Gln Ala Lys Arg Thr Lys Arg Lys Pro Lys Pro
                85                  90                  95

Gly Lys Arg Gln Arg Met Cys Met Lys Leu Glu Ser Asp Lys Thr Phe
            100                 105                 110

Pro Ile Met Leu Asn Gly Gln Val Asn Gly Tyr Ala Cys Val Val Gly
        115                 120                 125

Gly Arg Leu Met Lys Pro Leu His Val Glu Gly Lys Ile Asp Asn Glu
    130                 135                 140

Gln Leu Ala Ala Val Lys Leu Lys Lys Ala Ser Met Tyr Asp Leu Glu
```

-continued

```
            145                 150                 155                 160
Tyr Gly Asp Val Pro Gln Asn Met Lys Ser Asp Thr Leu Gln Tyr Thr
                165                 170                 175
Ser Asp Lys Pro Pro Gly Phe Tyr Asn Trp His His Gly Ala Val Gln
                180                 185                 190
Tyr Glu Asn Gly Arg Phe Thr Val Pro Arg Gly Val Gly Gly Lys Gly
                195                 200                 205
Asp Ser Gly Arg Pro Ile Leu Asp Asn Arg Gly Arg Val Val Ala Ile
            210                 215                 220
Val Leu Gly Gly Ala Asn Glu Gly Thr Arg Thr Ala Leu Ser Val Val
225                 230                 235                 240
Thr Trp Asn Gln Lys Gly Val Thr Ile Arg Asp Thr Pro Glu Gly Ser
                245                 250                 255
Glu Pro Trp Ser Leu Val Thr Ala Leu Cys Val Leu Ser Asn Val Thr
                260                 265                 270
Phe Pro Cys Asp Lys Pro Pro Val Cys Tyr Ser Leu Thr Pro Glu Arg
                275                 280                 285
Thr Leu Asp Val Leu Glu Glu Asn Val Asp Asn Pro Asn Tyr Asp Thr
            290                 295                 300
Leu Leu Glu Asn Val Leu Lys Cys Pro Ser Arg Arg Pro Lys Arg Ser
305                 310                 315                 320
Ile Thr Asp Asp Phe Thr Leu Thr Ser Pro Tyr Leu Gly Phe Cys Pro
                325                 330                 335
Tyr Cys Arg His Ser Thr Pro Cys Phe Ser Pro Ile Lys Ile Glu Asn
                340                 345                 350
Val Trp Asp Glu Ser Asp Asp Gly Ser Ile Arg Ile Gln Val Ser Ala
                355                 360                 365
Gln Phe Gly Tyr Asn Gln Ala Gly Thr Ala Asp Val Thr Lys Phe Arg
            370                 375                 380
Tyr Met Ser Phe Asp His Asp His Asp Ile Lys Glu Asp Ser Met Glu
385                 390                 395                 400
Lys Ile Ala Ile Ser Thr Ser Gly Pro Cys Arg Arg Leu Gly His Lys
                405                 410                 415
Gly Tyr Phe Leu Leu Ala Gln Cys Pro Pro Gly Asp Ser Val Thr Val
                420                 425                 430
Ser Ile Thr Ser Gly Ala Ser Glu Asn Ser Cys Thr Val Glu Lys Lys
            435                 440                 445
Ile Arg Arg Lys Phe Val Gly Arg Glu Glu Tyr Leu Phe Pro Pro Val
            450                 455                 460
His Gly Lys Leu Val Lys Cys His Val Tyr Asp His Leu Lys Glu Thr
465                 470                 475                 480
Ser Ala Gly Tyr Ile Thr Met His Arg Pro Gly Pro His Ala Tyr Lys
                485                 490                 495
Ser Tyr Leu Glu Glu Ala Ser Gly Glu Val Tyr Ile Lys Pro Pro Ser
                500                 505                 510
Gly Lys Asn Val Thr Tyr Glu Cys Lys Cys Gly Asp Tyr Ser Thr Gly
                515                 520                 525
Ile Val Ser Thr Arg Thr Lys Met Asn Gly Cys Thr Lys Ala Lys Gln
            530                 535                 540
Cys Ile Ala Tyr Lys Ser Asp Gln Thr Lys Trp Val Phe Asn Ser Pro
545                 550                 555                 560
Asp Leu Ile Arg His Thr Asp His Ser Val Gln Gly Lys Leu His Ile
                565                 570                 575
```

```
Pro Phe Arg Leu Thr Pro Thr Val Cys Pro Val Pro Leu Ala His Thr
            580                 585                 590

Pro Thr Val Thr Lys Trp Phe Lys Gly Ile Thr Leu His Leu Thr Ala
            595                 600                 605

Met Arg Pro Thr Leu Leu Thr Thr Arg Lys Leu Gly Leu Arg Ala Asp
            610                 615                 620

Ala Thr Ala Glu Trp Ile Thr Gly Ser Thr Ser Arg Asn Phe Ser Val
625                 630                 635                 640

Gly Arg Glu Gly Leu Glu Tyr Val Trp Gly Asn His Glu Pro Val Arg
            645                 650                 655

Val Trp Ala Gln Glu Ser Ala Pro Gly Asp Pro His Gly Trp Pro His
            660                 665                 670

Glu Ile Ile Ile His Tyr Tyr His Arg His Pro Val Tyr Thr Val Ile
            675                 680                 685

Val Leu Cys Gly Val Ala Leu Ala Ile Leu Val Gly Thr Ala Ser Ser
            690                 695                 700

Ala Ala Cys Ile Ala Lys Ala Arg Arg Asp Cys Leu Thr Pro Tyr Ala
705                 710                 715                 720

Leu Ala Pro Asn Ala Thr Val Pro Thr Ala Leu Ala Val Leu Cys Cys
            725                 730                 735

Ile Arg Pro Thr Asn Ala Glu Thr Phe Gly Glu Thr Leu Asn His Leu
            740                 745                 750

Trp Phe Asn Asn Gln Pro Phe Leu Trp Ala Gln Leu Cys Ile Pro Leu
            755                 760                 765

Ala Ala Leu Val Ile Leu Phe Arg Cys Phe Ser Cys Cys Met Pro Phe
            770                 775                 780

Leu Leu Val Ala Gly Val Cys Leu Gly Lys Val Asp Ala Phe Glu His
785                 790                 795                 800

Ala Thr Thr Val Pro Asn Val Pro Gly Ile Pro Tyr Lys Ala Leu Val
            805                 810                 815

Glu Arg Ala Gly Tyr Ala Pro Leu Asn Leu Glu Ile Thr Val Val Ser
            820                 825                 830

Ser Glu Leu Thr Pro Ser Thr Asn Lys Glu Tyr Val Thr Cys Lys Phe
            835                 840                 845

His Thr Val Ile Pro Ser Pro Gln Val Lys Cys Cys Gly Ser Leu Glu
            850                 855                 860

Cys Lys Ala Ser Ser Lys Ala Asp Tyr Thr Cys Arg Val Phe Gly Gly
865                 870                 875                 880

Val Tyr Pro Phe Met Trp Gly Gly Ala Gln Cys Phe Cys Asp Ser Glu
            885                 890                 895

Asn Thr Gln Leu Ser Glu Ala Tyr Val Glu Phe Ala Pro Asp Cys Thr
            900                 905                 910

Ile Asp His Ala Val Ala Leu Lys Val His Thr Ala Ala Leu Lys Val
            915                 920                 925

Gly Leu Arg Ile Val Tyr Gly Asn Thr Thr Ala His Leu Asp Thr Phe
            930                 935                 940

Val Asn Gly Val Thr Pro Gly Ser Ser Arg Asp Leu Lys Val Ile Ala
945                 950                 955                 960

Gly Pro Ile Ser Ala Ala Phe Ser Pro Phe Asp His Lys Val Val Ile
            965                 970                 975

Arg Lys Gly Leu Val Tyr Asn Tyr Asp Phe Pro Glu Tyr Gly Ala Met
            980                 985                 990
```

-continued

```
Lys Pro Gly Ala Phe Gly Asp Ile Gln Ala Ser Ser Leu Asp Ala Thr
        995                 1000                1005

Asp Ile Val Ala Arg Thr Asp Ile Arg Leu Leu Lys Pro Ser Val
    1010                1015                1020

Lys Asn Ile His Val Pro Tyr Thr Gln Ala Val Ser Gly Tyr Glu
    1025                1030                1035

Met Trp Lys Asn Asn Ser Gly Arg Pro Leu Gln Glu Thr Ala Pro
    1040                1045                1050

Phe Gly Cys Lys Ile Glu Val Glu Pro Leu Arg Ala Ser Asn Cys
    1055                1060                1065

Ala Tyr Gly His Ile Pro Ile Ser Ile Asp Ile Pro Asp Ala Ala
    1070                1075                1080

Phe Val Arg Ser Ser Glu Ser Pro Thr Ile Leu Glu Val Ser Cys
    1085                1090                1095

Thr Val Ala Asp Cys Ile Tyr Ser Ala Asp Phe Gly Gly Ser Leu
    1100                1105                1110

Thr Leu Gln Tyr Lys Ala Asp Arg Glu Gly His Cys Pro Val His
    1115                1120                1125

Ser His Ser Thr Thr Ala Val Leu Lys Glu Ala Thr Thr His Val
    1130                1135                1140

Thr Ala Val Gly Ser Ile Thr Leu His Phe Ser Thr Ser Ser Pro
    1145                1150                1155

Gln Ala Asn Phe Ile Val Ser Leu Cys Gly Lys Lys Ser Thr Cys
    1160                1165                1170

Asn Ala Glu Cys Lys Pro Pro Ala Asp His Ile Ile Gly Glu Pro
    1175                1180                1185

His Lys Val Asp Gln Glu Phe Gln Ala Ala Val Ser Lys Thr Ser
    1190                1195                1200

Trp Asn Trp Leu Leu Ala Leu Phe Gly Gly Ala Ser Ser Leu Ile
    1205                1210                1215

Val Val Gly Leu Ile Val Leu Val Cys Ser Ser Met Leu Ile Asn
    1220                1225                1230

Thr Arg Arg
    1235
```

<210> SEQ ID NO 5
<211> LENGTH: 4150
<212> TYPE: DNA
<213> ORGANISM: Western equine encephalomyelitis virus - strain 71V-1658
<220> FEATURE:
<221> NAME/KEY: CDS
<222> LOCATION: (159)..(3869)
<223> OTHER INFORMATION: vector sequence 1-9; 5' SacI primer 9-20; 3' end of NS4 gene 16-114; intragenic region 115-158; polyprotein (C-E3-E2-6K-E1) 159-3856; pcDW-XH7 nontranslated region 3857-4150

<400> SEQUENCE: 5

```
ggccctctag agctcatact ggcaggcctg atcatcacgt ctctgtccac gttagccgaa      60
agcgttaaga acttcaagag cataagaggg agcccaatca ccctctacgg ctgacctaaa     120
taggtgacgt agtagacacg cacctaccca ccggcaga atg ttt cca tac cct cag     176
                                         Met Phe Pro Tyr Pro Gln
                                          1               5 ctg aac ttt cca cca gtt tac cct aca aat ccg atg gct tac cga gat     224
Leu Asn Phe Pro Pro Val Tyr Pro Thr Asn Pro Met Ala Tyr Arg Asp
         10                  15                  20 cca aac cct cct agg cgc cgc tgg agg ccg ttt cgg ccc ccg ctg gct     272
Pro Asn Pro Pro Arg Arg Arg Trp Arg Pro Phe Arg Pro Pro Leu Ala
```

```
                25                   30                   35
gct caa atc gaa gat ctt agg agg tcg ata gtc aac ttg act ttc aaa      320
Ala Gln Ile Glu Asp Leu Arg Arg Ser Ile Val Asn Leu Thr Phe Lys
     40                  45                  50 caa cga tca cct aat ccg ccg cca ggt cca ccg cca aag aag aag aag      368
Gln Arg Ser Pro Asn Pro Pro Pro Gly Pro Pro Pro Lys Lys Lys Lys
 55                  60                  65                  70 agt gct cct aag cca aaa cct act cag cct aaa aag aag aag cag caa      416
Ser Ala Pro Lys Pro Lys Pro Thr Gln Pro Lys Lys Lys Lys Gln Gln
                 75                  80                  85 gcc aag agg acg aaa cgc aag cct aaa cca ggg aaa cga caa cgt atg      464
Ala Lys Arg Thr Lys Arg Lys Pro Lys Pro Gly Lys Arg Gln Arg Met
             90                  95                 100 tgt atg aag ttg gag tcg gac aag aca ttt ccg atc atg ctg aac ggc      512
Cys Met Lys Leu Glu Ser Asp Lys Thr Phe Pro Ile Met Leu Asn Gly
        105                 110                 115 caa gtg aat gga tat gcc tgc gtt gtc gga gga agg ctg atg aaa cca      560
Gln Val Asn Gly Tyr Ala Cys Val Val Gly Gly Arg Leu Met Lys Pro
    120                 125                 130 ctc cac gtt gaa gga aaa att gat aat gag caa tta gcg gcc gtg aaa      608
Leu His Val Glu Gly Lys Ile Asp Asn Glu Gln Leu Ala Ala Val Lys
135                 140                 145                 150 ttg aag aag gct agc atg tac gac ttg gag tac ggc gac gtt ccc cag      656
Leu Lys Lys Ala Ser Met Tyr Asp Leu Glu Tyr Gly Asp Val Pro Gln
                155                 160                 165 aac atg aaa tca gac acg ctg cag tac acc agc gac aaa cca ccg ggc      704
Asn Met Lys Ser Asp Thr Leu Gln Tyr Thr Ser Asp Lys Pro Pro Gly
            170                 175                 180 ttc tac aac tgg cac cac ggc gca gtc cag tat gag aat ggg aga ttt      752
Phe Tyr Asn Trp His His Gly Ala Val Gln Tyr Glu Asn Gly Arg Phe
        185                 190                 195 acc gta ccg aga gga gtg ggc ggg aaa ggc gac agc gga aga ccg atc      800
Thr Val Pro Arg Gly Val Gly Gly Lys Gly Asp Ser Gly Arg Pro Ile
    200                 205                 210 ctg gac aac aga ggc aga gtt gtg gct att gtt cta gga ggt gca aat      848
Leu Asp Asn Arg Gly Arg Val Val Ala Ile Val Leu Gly Gly Ala Asn
215                 220                 225                 230 gag ggc acg cgt acg gcg ctt tca gtg gtc act tgg aac cag aaa ggg      896
Glu Gly Thr Arg Thr Ala Leu Ser Val Val Thr Trp Asn Gln Lys Gly
                235                 240                 245 gtg acc att agg gat acc ccc gaa ggt tct gaa ccg tgg tca cta gtt      944
Val Thr Ile Arg Asp Thr Pro Glu Gly Ser Glu Pro Trp Ser Leu Val
            250                 255                 260 aca gcg cta tgc gtg ctt tcg aat gtc acg ttc cca tgc gac aaa cca      992
Thr Ala Leu Cys Val Leu Ser Asn Val Thr Phe Pro Cys Asp Lys Pro
        265                 270                 275 ccc gtg tgc tat tca ctg acg cca gaa cga aca ctc gac gtg ctc gaa     1040
Pro Val Cys Tyr Ser Leu Thr Pro Glu Arg Thr Leu Asp Val Leu Glu
    280                 285                 290 gag aac gtc gac aat cca aat tac gac acg ctg ctg gag aac gtc ttg     1088
Glu Asn Val Asp Asn Pro Asn Tyr Asp Thr Leu Leu Glu Asn Val Leu
295                 300                 305                 310 aaa tgt cca tca cgc cgg ccc aaa cga agc att acc gat gac ttc aca     1136
Lys Cys Pro Ser Arg Arg Pro Lys Arg Ser Ile Thr Asp Asp Phe Thr
                315                 320                 325 ctg acc agt ccc tac ctg ggg ttc tgc ccg tat tgc aga cac tca acg     1184
Leu Thr Ser Pro Tyr Leu Gly Phe Cys Pro Tyr Cys Arg His Ser Thr
            330                 335                 340 ccg tgt ttc agc cca ata aaa att gag aac gtg tgg gac gaa tct gat     1232
```

```
                Pro Cys Phe Ser Pro Ile Lys Ile Glu Asn Val Trp Asp Glu Ser Asp
                        345                 350                 355 gat gga tcg att aga atc cag gtc tcg gca caa ttc ggc tac aat cag      1280
Asp Gly Ser Ile Arg Ile Gln Val Ser Ala Gln Phe Gly Tyr Asn Gln
360                 365                 370 gca ggc act gcg gat gtc acc aaa ttc cgt tac atg tct ttc gac cac      1328
Ala Gly Thr Ala Asp Val Thr Lys Phe Arg Tyr Met Ser Phe Asp His
375                 380                 385                 390 gac cat gac atc aag gaa gac agt atg gag aaa ata gct atc agc aca      1376
Asp His Asp Ile Lys Glu Asp Ser Met Glu Lys Ile Ala Ile Ser Thr
                395                 400                 405 tct gga ccc tgc cgt cgt ctt ggc cac aaa ggg tac ttc ctg tta gct      1424
Ser Gly Pro Cys Arg Arg Leu Gly His Lys Gly Tyr Phe Leu Leu Ala
            410                 415                 420 caa tgt cct cca ggt gac agt gta acc gtc agt atc acg agc gga gca      1472
Gln Cys Pro Pro Gly Asp Ser Val Thr Val Ser Ile Thr Ser Gly Ala
        425                 430                 435 tct gag aat tca tgc acc gtg gag aaa aag atc agg agg aag ttt gtc      1520
Ser Glu Asn Ser Cys Thr Val Glu Lys Lys Ile Arg Arg Lys Phe Val
    440                 445                 450 ggt aga gag gag tac ttg ttc cca ccc gtc cat gga aag ctg gta aag      1568
Gly Arg Glu Glu Tyr Leu Phe Pro Pro Val His Gly Lys Leu Val Lys
455                 460                 465                 470 tgc cac gtt tac gat cac ttg aag gag acg tct gcc ggg tac ata acc      1616
Cys His Val Tyr Asp His Leu Lys Glu Thr Ser Ala Gly Tyr Ile Thr
                475                 480                 485 atg cac agg cca ggc cca cac gcg tat aag tcc tat ctg gag gaa gcg      1664
Met His Arg Pro Gly Pro His Ala Tyr Lys Ser Tyr Leu Glu Glu Ala
                490                 495                 500 tca ggc gaa gtg tac att aaa cca cct tct ggc aag aac gtc acc tac      1712
Ser Gly Glu Val Tyr Ile Lys Pro Pro Ser Gly Lys Asn Val Thr Tyr
            505                 510                 515 gaa tgt aag tgt ggc gac tac agc aca ggt atc gtg agc acg cga acg      1760
Glu Cys Lys Cys Gly Asp Tyr Ser Thr Gly Ile Val Ser Thr Arg Thr
        520                 525                 530 aag atg aac ggc tgc act aaa gca aaa cag tgc att gcc tac aag agc      1808
Lys Met Asn Gly Cys Thr Lys Ala Lys Gln Cys Ile Ala Tyr Lys Ser
535                 540                 545                 550 gac caa acg aaa tgg gtc ttc aac tcg ccg gat ctt att agg cac aca      1856
Asp Gln Thr Lys Trp Val Phe Asn Ser Pro Asp Leu Ile Arg His Thr
                555                 560                 565 gac cac tca gtg caa ggt aaa ttg cac att cca ttc cgc ttg aca ccg      1904
Asp His Ser Val Gln Gly Lys Leu His Ile Pro Phe Arg Leu Thr Pro
                570                 575                 580 aca gtc tgc ccg gtt ccg tta gct cac acg cct aca gtc acg aag tgg      1952
Thr Val Cys Pro Val Pro Leu Ala His Thr Pro Thr Val Thr Lys Trp
            585                 590                 595 ttc aaa ggc atc acc ctc cac ctg act gca atg cga cca aca ttg ctg      2000
Phe Lys Gly Ile Thr Leu His Leu Thr Ala Met Arg Pro Thr Leu Leu
        600                 605                 610 aca acg aga aaa ttg ggg ctg cga gca gac gca aca gca gaa tgg att      2048
Thr Thr Arg Lys Leu Gly Leu Arg Ala Asp Ala Thr Ala Glu Trp Ile
615                 620                 625                 630 aca ggg tct aca tcc agg aat ttt tct gtg ggg cga gaa ggg ctg gag      2096
Thr Gly Ser Thr Ser Arg Asn Phe Ser Val Gly Arg Glu Gly Leu Glu
                635                 640                 645 tac gta tgg ggt aac cat gaa cca gtc aga gtc tgg gcc cag gag tcg      2144
Tyr Val Trp Gly Asn His Glu Pro Val Arg Val Trp Ala Gln Glu Ser
                650                 655                 660
```

```
gca cca ggc gac cca cat gga tgg ccg cat gag atc atc atc cac tat    2192
Ala Pro Gly Asp Pro His Gly Trp Pro His Glu Ile Ile Ile His Tyr
        665                 670                 675 tat cat cgg cat cca gtc tac act gtc att gtg ctg tgt ggt gtc gct    2240
Tyr His Arg His Pro Val Tyr Thr Val Ile Val Leu Cys Gly Val Ala
    680                 685                 690 ctt gct atc ctg gta ggc act gca tca tca gca gct tgc atc gcc aaa    2288
Leu Ala Ile Leu Val Gly Thr Ala Ser Ser Ala Ala Cys Ile Ala Lys
695                 700                 705                 710 gca aga aga gac tgc ctg acg cca tac gcg ctt gca ccg aac gca acg    2336
Ala Arg Arg Asp Cys Leu Thr Pro Tyr Ala Leu Ala Pro Asn Ala Thr
                715                 720                 725 gta ccc aca gca tta gcg gtt ttg tgc tgc att cgg cca acc aac gct    2384
Val Pro Thr Ala Leu Ala Val Leu Cys Cys Ile Arg Pro Thr Asn Ala
            730                 735                 740 gaa aca ttt gga gaa act ttg aac cat ctg tgg ttt aac aac caa ccg    2432
Glu Thr Phe Gly Glu Thr Leu Asn His Leu Trp Phe Asn Asn Gln Pro
        745                 750                 755 ttt ctc tgg gca cag ttg tgc att cct ctg gca gcg ctt gtt att ctg    2480
Phe Leu Trp Ala Gln Leu Cys Ile Pro Leu Ala Ala Leu Val Ile Leu
    760                 765                 770 ttc cgc tgc ttt tca tgc tgc atg cct ttt tta ttg gtt gca ggc gtc    2528
Phe Arg Cys Phe Ser Cys Cys Met Pro Phe Leu Leu Val Ala Gly Val
775                 780                 785                 790 tgc ctg ggg aag gta gac gcc ttc gaa cat gcg acc act gtg cca aat    2576
Cys Leu Gly Lys Val Asp Ala Phe Glu His Ala Thr Thr Val Pro Asn
                795                 800                 805 gtt ccg ggg atc ccg tat aag gcg ttg gtc gaa cgc gca ggt tac gcg    2624
Val Pro Gly Ile Pro Tyr Lys Ala Leu Val Glu Arg Ala Gly Tyr Ala
            810                 815                 820 cca ctt aac ctg gag atc acg gtc gtc tca tcg gaa tta aca cct tca    2672
Pro Leu Asn Leu Glu Ile Thr Val Val Ser Ser Glu Leu Thr Pro Ser
        825                 830                 835 act aac aag gag tac gtg acc tgc aaa ttc cac aca gtc att cct tca    2720
Thr Asn Lys Glu Tyr Val Thr Cys Lys Phe His Thr Val Ile Pro Ser
    840                 845                 850 cca caa gtt aaa tgc tgc ggg tcc ctc gag tgc aag gca tcc tca aag    2768
Pro Gln Val Lys Cys Cys Gly Ser Leu Glu Cys Lys Ala Ser Ser Lys
855                 860                 865                 870 gcg gat tac aca tgc cgc gtt ttt ggc ggt gtg tac cct ttc atg tgg    2816
Ala Asp Tyr Thr Cys Arg Val Phe Gly Gly Val Tyr Pro Phe Met Trp
                875                 880                 885 gga ggc gca caa tgc ttc tgt gac agt gag aac aca caa ctg agt gag    2864
Gly Gly Ala Gln Cys Phe Cys Asp Ser Glu Asn Thr Gln Leu Ser Glu
            890                 895                 900 gcg tac gtc gag ttc gct cca gac tgc act ata gat cac gca gtc gca    2912
Ala Tyr Val Glu Phe Ala Pro Asp Cys Thr Ile Asp His Ala Val Ala
        905                 910                 915 cta aaa gtt cac aca gct gct ctg aaa gtc ggc ctg cgt ata gta tac    2960
Leu Lys Val His Thr Ala Ala Leu Lys Val Gly Leu Arg Ile Val Tyr
    920                 925                 930 ggc aac acc acc gcg cac ctg gat acg ttt gtc aat ggc gtc acg cca    3008
Gly Asn Thr Thr Ala His Leu Asp Thr Phe Val Asn Gly Val Thr Pro
935                 940                 945                 950 ggt tcc tca cgg gac ctg aag gtc ata gca ggg ccg ata tca gcc gct    3056
Gly Ser Ser Arg Asp Leu Lys Val Ile Ala Gly Pro Ile Ser Ala Ala
                955                 960                 965 ttt tca ccc ttt gac cat aag gtc gtc atc aga aag ggg ctt gtt tac    3104
Phe Ser Pro Phe Asp His Lys Val Val Ile Arg Lys Gly Leu Val Tyr
            970                 975                 980
```

-continued

| | |
|---|---|
| aac tac gac ttc cct gag tat gga gct atg aaa cca gga gcg ttc ggc<br>Asn Tyr Asp Phe Pro Glu Tyr Gly Ala Met Lys Pro Gly Ala Phe Gly<br>                985                990                995 | 3152 |
| gat att caa gca tcc tcg ctt gat gct aca gac ata gta gcc cgc<br>Asp Ile Gln Ala Ser Ser Leu Asp Ala Thr Asp Ile Val Ala Arg<br>    1000                1005                1010 | 3197 |
| act gac ata cgg ctg ctg aag cct tct gtc aag aac atc cac gtc<br>Thr Asp Ile Arg Leu Leu Lys Pro Ser Val Lys Asn Ile His Val<br>    1015                1020                1025 | 3242 |
| ccc tac acc caa gca gta tca ggg tat gaa atg tgg aag aac aac<br>Pro Tyr Thr Gln Ala Val Ser Gly Tyr Glu Met Trp Lys Asn Asn<br>    1030                1035                1040 | 3287 |
| tca gga cga ccc ctg caa gaa aca gca cca ttt gga tgt aaa att<br>Ser Gly Arg Pro Leu Gln Glu Thr Ala Pro Phe Gly Cys Lys Ile<br>    1045                1050                1055 | 3332 |
| gaa gtg gag cct ctg cga gcg tct aac tgt gct tac ggg cac atc<br>Glu Val Glu Pro Leu Arg Ala Ser Asn Cys Ala Tyr Gly His Ile<br>    1060                1065                1070 | 3377 |
| cct atc tcg att gac atc cct gat gca gct ttt gtg aga tca tca<br>Pro Ile Ser Ile Asp Ile Pro Asp Ala Ala Phe Val Arg Ser Ser<br>    1075                1080                1085 | 3422 |
| gaa tca cca aca att tta gaa gtt agc tgc aca gta gca gac tgc<br>Glu Ser Pro Thr Ile Leu Glu Val Ser Cys Thr Val Ala Asp Cys<br>    1090                1095                1100 | 3467 |
| att tat tct gca gac ttt ggt ggt tct cta aca tta cag tac aaa<br>Ile Tyr Ser Ala Asp Phe Gly Gly Ser Leu Thr Leu Gln Tyr Lys<br>    1105                1110                1115 | 3512 |
| gct gac agg gag gga cat tgt cca gtt cac tcc cac tcc acg aca<br>Ala Asp Arg Glu Gly His Cys Pro Val His Ser His Ser Thr Thr<br>    1120                1125                1130 | 3557 |
| gct gtt ttg aag gaa gcg acc aca cat gtg act gcc gta ggc agc<br>Ala Val Leu Lys Glu Ala Thr Thr His Val Thr Ala Val Gly Ser<br>    1135                1140                1145 | 3602 |
| ata aca cta cat ttt agc aca tcg agc cca caa gca aat ttt ata<br>Ile Thr Leu His Phe Ser Thr Ser Ser Pro Gln Ala Asn Phe Ile<br>    1150                1155                1160 | 3647 |
| gtt tcg cta tgc ggc aag aag tcc acc tgc aat gct gaa tgt aaa<br>Val Ser Leu Cys Gly Lys Lys Ser Thr Cys Asn Ala Glu Cys Lys<br>    1165                1170                1175 | 3692 |
| cca ccg gcc gac cac ata att gga gaa cca cat aaa gtc gac caa<br>Pro Pro Ala Asp His Ile Ile Gly Glu Pro His Lys Val Asp Gln<br>    1180                1185                1190 | 3737 |
| gaa ttc cag gcg gca gtt tcc aaa aca tct tgg aac tgg ctg ctt<br>Glu Phe Gln Ala Ala Val Ser Lys Thr Ser Trp Asn Trp Leu Leu<br>    1195                1200                1205 | 3782 |
| gca ctg ttt ggg gga gca tca tcc ctc att gtt gta gga ctt ata<br>Ala Leu Phe Gly Gly Ala Ser Ser Leu Ile Val Val Gly Leu Ile<br>    1210                1215                1220 | 3827 |
| gtg ttg gtc tgc agc tct atg ctt ata aac aca cgt aga tga<br>Val Leu Val Cys Ser Ser Met Leu Ile Asn Thr Arg Arg<br>    1225                1230                1235 | 3869 |
| ctgagcgcgg acactgacat agcggtaaaa ctcgatgtac ttccgaggaa gcgtggtgca | 3929 |
| taatgccacg cgccgcttga cactaaaact cgatgtattt ccgaggaagc acagtgcata | 3989 |
| atgctgtgca gtgtcacatt aatcgtatat cacactacat attaacaaca ctatatcact | 4049 |
| tttatgagac tcactatggg tctctaatat acactacaca tattttactt aaaaacacta | 4109 |
| tacacacttt ataattctc tcataatttc actttaggtt t | 4150 |

-continued

<210> SEQ ID NO 6
<211> LENGTH: 1236
<212> TYPE: PRT
<213> ORGANISM: Western equine encephalomyelitis virus - strain 71V-1658

<400> SEQUENCE: 6

```
Met Phe Pro Tyr Pro Gln Leu Asn Phe Pro Pro Val Tyr Pro Thr Asn
1               5                   10                  15

Pro Met Ala Tyr Arg Asp Pro Asn Pro Pro Arg Arg Trp Arg Pro
            20                  25                  30

Phe Arg Pro Pro Leu Ala Ala Gln Ile Glu Asp Leu Arg Arg Ser Ile
            35                  40                  45

Val Asn Leu Thr Phe Lys Gln Arg Ser Pro Asn Pro Pro Gly Pro
        50                  55                  60

Pro Pro Lys Lys Lys Lys Ser Ala Pro Lys Pro Lys Pro Thr Gln Pro
65                  70                  75                  80

Lys Lys Lys Lys Gln Gln Ala Lys Arg Thr Lys Arg Lys Pro Lys Pro
                85                  90                  95

Gly Lys Arg Gln Arg Met Cys Met Lys Leu Glu Ser Asp Lys Thr Phe
            100                 105                 110

Pro Ile Met Leu Asn Gly Gln Val Asn Gly Tyr Ala Cys Val Val Gly
            115                 120                 125

Gly Arg Leu Met Lys Pro Leu His Val Glu Gly Lys Ile Asp Asn Glu
            130                 135                 140

Gln Leu Ala Ala Val Lys Leu Lys Lys Ala Ser Met Tyr Asp Leu Glu
145                 150                 155                 160

Tyr Gly Asp Val Pro Gln Asn Met Lys Ser Asp Thr Leu Gln Tyr Thr
                165                 170                 175

Ser Asp Lys Pro Pro Gly Phe Tyr Asn Trp His His Gly Ala Val Gln
            180                 185                 190

Tyr Glu Asn Gly Arg Phe Thr Val Pro Arg Gly Val Gly Gly Lys Gly
            195                 200                 205

Asp Ser Gly Arg Pro Ile Leu Asp Asn Arg Gly Arg Val Val Ala Ile
        210                 215                 220

Val Leu Gly Gly Ala Asn Glu Gly Thr Arg Thr Ala Leu Ser Val Val
225                 230                 235                 240

Thr Trp Asn Gln Lys Gly Val Thr Ile Arg Asp Thr Pro Glu Gly Ser
                245                 250                 255

Glu Pro Trp Ser Leu Val Thr Ala Leu Cys Val Leu Ser Asn Val Thr
            260                 265                 270

Phe Pro Cys Asp Lys Pro Pro Val Cys Tyr Ser Leu Thr Pro Glu Arg
        275                 280                 285

Thr Leu Asp Val Leu Glu Glu Asn Val Asp Asn Pro Asn Tyr Asp Thr
        290                 295                 300

Leu Leu Glu Asn Val Leu Lys Cys Pro Ser Arg Arg Pro Lys Arg Ser
305                 310                 315                 320

Ile Thr Asp Asp Phe Thr Leu Thr Ser Pro Tyr Leu Gly Phe Cys Pro
                325                 330                 335

Tyr Cys Arg His Ser Thr Pro Cys Phe Ser Pro Ile Lys Ile Glu Asn
            340                 345                 350

Val Trp Asp Glu Ser Asp Asp Gly Ser Ile Arg Ile Gln Val Ser Ala
            355                 360                 365

Gln Phe Gly Tyr Asn Gln Ala Gly Thr Ala Asp Val Thr Lys Phe Arg
        370                 375                 380
```

-continued

```
Tyr Met Ser Phe Asp His Asp His Asp Ile Lys Glu Asp Ser Met Glu
385                 390                 395                 400

Lys Ile Ala Ile Ser Thr Ser Gly Pro Cys Arg Arg Leu Gly His Lys
            405                 410                 415

Gly Tyr Phe Leu Leu Ala Gln Cys Pro Pro Gly Asp Ser Val Thr Val
                420                 425                 430

Ser Ile Thr Ser Gly Ala Ser Glu Asn Ser Cys Thr Val Glu Lys Lys
        435                 440                 445

Ile Arg Arg Lys Phe Val Gly Arg Glu Glu Tyr Leu Phe Pro Pro Val
450                 455                 460

His Gly Lys Leu Val Lys Cys His Val Tyr Asp His Leu Lys Glu Thr
465                 470                 475                 480

Ser Ala Gly Tyr Ile Thr Met His Arg Pro Gly Pro His Ala Tyr Lys
                485                 490                 495

Ser Tyr Leu Glu Glu Ala Ser Gly Glu Val Tyr Ile Lys Pro Pro Ser
        500                 505                 510

Gly Lys Asn Val Thr Tyr Glu Cys Lys Cys Gly Asp Tyr Ser Thr Gly
    515                 520                 525

Ile Val Ser Thr Arg Thr Lys Met Asn Gly Cys Thr Lys Ala Lys Gln
530                 535                 540

Cys Ile Ala Tyr Lys Ser Asp Gln Thr Lys Trp Val Phe Asn Ser Pro
545                 550                 555                 560

Asp Leu Ile Arg His Thr Asp His Ser Val Gln Gly Lys Leu His Ile
                565                 570                 575

Pro Phe Arg Leu Thr Pro Thr Val Cys Pro Val Pro Leu Ala His Thr
        580                 585                 590

Pro Thr Val Thr Lys Trp Phe Lys Gly Ile Thr Leu His Leu Thr Ala
    595                 600                 605

Met Arg Pro Thr Leu Leu Thr Thr Arg Lys Leu Gly Leu Arg Ala Asp
610                 615                 620

Ala Thr Ala Glu Trp Ile Thr Gly Ser Thr Ser Arg Asn Phe Ser Val
625                 630                 635                 640

Gly Arg Glu Gly Leu Glu Tyr Val Trp Gly Asn His Glu Pro Val Arg
                645                 650                 655

Val Trp Ala Gln Glu Ser Ala Pro Gly Asp Pro His Gly Trp Pro His
        660                 665                 670

Glu Ile Ile Ile His Tyr Tyr His Arg His Pro Val Tyr Thr Val Ile
    675                 680                 685

Val Leu Cys Gly Val Ala Leu Ala Ile Leu Val Gly Thr Ala Ser Ser
690                 695                 700

Ala Ala Cys Ile Ala Lys Ala Arg Arg Asp Cys Leu Thr Pro Tyr Ala
705                 710                 715                 720

Leu Ala Pro Asn Ala Thr Val Pro Thr Ala Leu Ala Val Leu Cys Cys
                725                 730                 735

Ile Arg Pro Thr Asn Ala Glu Thr Phe Gly Glu Thr Leu Asn His Leu
        740                 745                 750

Trp Phe Asn Asn Gln Pro Phe Leu Trp Ala Gln Leu Cys Ile Pro Leu
    755                 760                 765

Ala Ala Leu Val Ile Leu Phe Arg Cys Phe Ser Cys Cys Met Pro Phe
770                 775                 780

Leu Leu Val Ala Gly Val Cys Leu Gly Lys Val Asp Ala Phe Glu His
785                 790                 795                 800
```

```
Ala Thr Thr Val Pro Asn Val Pro Gly Ile Pro Tyr Lys Ala Leu Val
            805                 810                 815

Glu Arg Ala Gly Tyr Ala Pro Leu Asn Leu Glu Ile Thr Val Val Ser
            820                 825                 830

Ser Glu Leu Thr Pro Ser Thr Asn Lys Glu Tyr Val Thr Cys Lys Phe
            835                 840                 845

His Thr Val Ile Pro Ser Pro Gln Val Lys Cys Cys Gly Ser Leu Glu
            850                 855                 860

Cys Lys Ala Ser Ser Lys Ala Asp Tyr Thr Cys Arg Val Phe Gly Gly
865                 870                 875                 880

Val Tyr Pro Phe Met Trp Gly Gly Ala Gln Cys Phe Cys Asp Ser Glu
                885                 890                 895

Asn Thr Gln Leu Ser Glu Ala Tyr Val Glu Phe Ala Pro Asp Cys Thr
            900                 905                 910

Ile Asp His Ala Val Ala Leu Lys Val His Thr Ala Ala Leu Lys Val
            915                 920                 925

Gly Leu Arg Ile Val Tyr Gly Asn Thr Thr Ala His Leu Asp Thr Phe
930                 935                 940

Val Asn Gly Val Thr Pro Gly Ser Ser Arg Asp Leu Lys Val Ile Ala
945                 950                 955                 960

Gly Pro Ile Ser Ala Ala Phe Ser Pro Phe Asp His Lys Val Val Ile
                965                 970                 975

Arg Lys Gly Leu Val Tyr Asn Tyr Asp Phe Pro Glu Tyr Gly Ala Met
            980                 985                 990

Lys Pro Gly Ala Phe Gly Asp Ile Gln Ala Ser Ser Leu Asp Ala Thr
            995                 1000                1005

Asp Ile Val Ala Arg Thr Asp Ile Arg Leu Leu Lys Pro Ser Val
    1010                1015                1020

Lys Asn Ile His Val Pro Tyr Thr Gln Ala Val Ser Gly Tyr Glu
    1025                1030                1035

Met Trp Lys Asn Asn Ser Gly Arg Pro Leu Gln Glu Thr Ala Pro
    1040                1045                1050

Phe Gly Cys Lys Ile Glu Val Glu Pro Leu Arg Ala Ser Asn Cys
    1055                1060                1065

Ala Tyr Gly His Ile Pro Ile Ser Ile Asp Ile Pro Asp Ala Ala
    1070                1075                1080

Phe Val Arg Ser Ser Glu Ser Pro Thr Ile Leu Glu Val Ser Cys
    1085                1090                1095

Thr Val Ala Asp Cys Ile Tyr Ser Ala Asp Phe Gly Gly Ser Leu
    1100                1105                1110

Thr Leu Gln Tyr Lys Ala Asp Arg Glu Gly His Cys Pro Val His
    1115                1120                1125

Ser His Ser Thr Thr Ala Val Leu Lys Glu Ala Thr Thr His Val
    1130                1135                1140

Thr Ala Val Gly Ser Ile Thr Leu His Phe Ser Thr Ser Ser Pro
    1145                1150                1155

Gln Ala Asn Phe Ile Val Ser Leu Cys Gly Lys Lys Ser Thr Cys
    1160                1165                1170

Asn Ala Glu Cys Lys Pro Pro Ala Asp His Ile Ile Gly Glu Pro
    1175                1180                1185

His Lys Val Asp Gln Glu Phe Gln Ala Ala Val Ser Lys Thr Ser
    1190                1195                1200

Trp Asn Trp Leu Leu Ala Leu Phe Gly Gly Ala Ser Ser Leu Ile
```

-continued

|      |      | 1205 |      |      |      | 1210 |      |      |      | 1215 |      |
| Val  | Val  | Gly  | Leu  | Ile  | Val  | Leu  | Val  | Cys  | Ser  | Ser  | Met  | Leu | Ile | Asn |
|      |      | 1220 |      |      |      | 1225 |      |      |      | 1230 |      |

Thr Arg Arg
    1235

<210> SEQ ID NO 7
<211> LENGTH: 4395
<212> TYPE: DNA
<213> ORGANISM: Western equine encephalomyelitis virus - STRAIN 71v-1658
<220> FEATURE:
<221> NAME/KEY: CMV promoter
<222> LOCATION: (1)..(1260)
<223> OTHER INFORMATION: Pvax vector sequence: 1-196; CMV promoter:
    1-115; CMV putative transcriptional start site: 125; T7 promoter:
    48-167; pVAX multicloning region: 168-196; polyprotein
    (C-E3-E2-6K-E1): 214-4065; pcDW-HX45 nontranslated region:
    4066-4348;
<220> FEATURE:
<223> OTHER INFORMATION: pcDW-HX45 vector sequence: 4349-4385; pVAX
    vector sequence: 4386

<400> SEQUENCE: 7

```
accaaaatca acgggacttt ccaaaatgtc gtaacaactc cgccccattg acgcaaatgg    60
gcggtaggcg tgtacggtgg gaggtcatat ataagcagag tctctctggc taactagaga   120
acccactgct tactggctta tcgaaattaa tacgactcac tataggraga cccaagctgg   180
ctagcgttta aacttaagct tggtaccgag ctcatactgg caggcctgat catcacgtct   240
ctgtccacgt tagccgaaag cgttaagaac ttcaagagca taagagggag cccaatcacc   300
ctctacggct gacctaaata ggtgacgtag tagacacgca cctacccacc gccagaatgt   360
ttccataccc tcagctgaac tttccaccag tttaccctac aaatccgatg gcttaccgag   420
atccaaaccc tcctaggcgc cgctggaggc cgtttcggcc cccgctggct gctcaaatcg   480
aagatcttag gaggtcgata gtcaacttga ctttcaaaca acgatcacct aatccgccgc   540
caggtccacc gccaaagaag aagaagagtg ctcctaagcc aaaacctact cagcctaaaa   600
agaagaagca gcaagccaag aggacgaaac gcaagcctaa accagggaaa cgacaacgta   660
tgtgtatgaa gttggagtcg gacaagacat tccgatcat gctgaacggc caagtgaatg   720
gatatgcctg cgttgtcgga ggaaggctga tgaaaccact ccacgttgaa ggaaaaattg   780
ataatgagca attagcggcc gtgaaattga agaaggctag catgtacgac ttggagtacg   840
gcgacgttcc ccagaacatg aaatcagaca cgctgcagta caccagcgac aaaccaccgg   900
gcttctacaa ctggcaccac ggcgcagtcc agtatgagaa tgggagattt accgtaccga   960
gaggagtggg cgggaaaggc gacagcggaa gaccgatcct ggacaacaga ggcagagttg  1020
tggctattgt tctaggaggt gcaaatgagg gcacgcgtac ggcgctttca gtggtcactt  1080
ggaaccagaa agggggtgacc attagggata ccccgaagg ttctgaaccg tggtcactag  1140
ttacagcgct atgcgtgctt tcgaatgtca cgttcccatg cgacaaacca cccgtgtgct  1200
attcactgac gccagaacga acactcgacg tgctcgaaga aacgtcgac aatccaaatt  1260 acgacacgct gctggagaac gtcttgaaat gtccatcacg ccggcccaaa cgaagcatta  1320
ccgatgactt cacactgacc agtccctacc tgggttctg cccgtattgc agacactcaa  1380
cgccgtgttt cagcccaata aaaattgaga acgtgtggga cgaatctgat gatggatcga  1440
ttagaatcca ggtctcggca caattcggct acaatcaggc aggcactgcg gatgtcacca  1500
aattccgtta catgtctttc gaccacgacc atgacatcaa ggaagacagt atggagaaaa  1560
```

-continued

```
tagctatcag cacatctgga ccctgccgtc gtcttggcca caaagggtac ttcctgttag   1620
ctcaatgtcc tccaggtgac agtgtaaccg tcagtatcac gagcggagca tctgagaatt   1680
catgcaccgt ggagaaaaag atcaggagga agtttgtcgg tagagaggag tacttgttcc   1740
cacccgtcca tggaaagctg gtaaagtgcc acgtttacga tcacttgaag gagacgtctg   1800
ccgggtacat aaccatgcac aggccaggcc cacacgcgta taagtcctat ctggaggaag   1860
cgtcaggcga agtgtacatt aaaccacctt ctggcaagaa cgtcacctac gaatgtaagt   1920
gtggcgacta cagcacaggt atcgtgagca cgcgaacgaa gatgaacggc tgcactaaag   1980
caaaacagtg cattgcctac aagagcgacc aaacgaaatg ggtcttcaac tcgccggatc   2040
ttattaggca cacagaccac tcagtgcaag gtaaattgca cattccattc cgcttgacac   2100
cgacagtctg cccggttccg ttagctcaca cgcctacagt cacgaagtgg ttcaaaggca   2160
tcaccctcca cctgactgca atgcgaccaa cattgctgac aacgagaaaa ttggggctgc   2220
gagcagacgc aacagcagaa tggattacag ggtctacatc caggaatttt tctgtggggc   2280
gagaagggct ggagtacgta tggggtaacc atgaaccagt cagagtctgg gcccaggagt   2340
cggcaccagg cgacccacat ggatggccgc atgagatcat catccactat tatcatcggc   2400
atccagtcta cactgtcatt gtgctgtgtg gtgtcgctct tgctatcctg gtaggcactg   2460
catcatcagc agcttgcatc gccaaagcaa gaagagactg cctgacgcca tacgcgcttg   2520
caccgaacgc aacggtaccc acagcattag cggttttgtg ctgcattcgg ccaaccaacg   2580
ctgaaacatt tggagaaact ttgaaccatc tgtggtttaa caaccaaccg tttctctggg   2640
cacagttgtg cattcctctg gcagcgcttg ttattctgtt ccgctgcttt tcatgctgca   2700 tgccttttt attggttgca ggcgtctgcc tggggaaggt agacgccttc gaacatgcga   2760
ccactgtgcc aaatgttccg gggatcccgt ataaggcgtt ggtcgaacgc gcaggttacg   2820
cgccacttaa cctggagatc acgtcgtct catcggaatt aacaccttca actaacaagg   2880
agtacgtgac ctgcaaattc cacacagtca ttccttcacc acaagttaaa tgctgcgggt   2940
ccctcgagtg caaggcatcc tcaaaggcgg attacacatg ccgcgttttt ggcggtgtgt   3000 acccttttcat gtggggaggc gcacaatgct tctgtgacag tgagaacaca caactgagtg   3060
aggcgtacgt cgagttcgct ccagactgca ctatagatca cgcagtcgca ctaaaagttc   3120
acacagctgc tctgaaagtc ggcctgcgta tagtatacgg caacaccacc gcgcacctgg   3180
atacgtttgt caatggcgtc acgccaggtt cctcacggga cctgaaggtc atagcagggc   3240
cgatatcagc cgcttttttca ccctttgacc ataaggtcgt catcagaaag gggcttgttt   3300
acaactacga cttccctgag tatggagcta tgaaaccagg agcgttcggc gatattcaag   3360
catcctcgct tgatgctaca gacatagtag cccgcactga catacggctg ctgaagcctt   3420
ctgtcaagaa catccacgtc ccctacaccc aagcagtatc agggtatgaa atgtggaaga   3480
acaactcagg acgaccctg caagaaacag caccatttgg atgtaaaatt gaagtggagc   3540
ctctgcgagc gtctaactgt gcttacgggc acatccctat ctcgattgac atccctgatg   3600
cagcttttgt gagatcatca gaatcaccaa caatttaga agttagctgc acagtagcag   3660
actgcattta ttctgcagac tttggtggtt ctctaacatt acagtacaaa gctgacaggg   3720
agggacattg tccagttcac tcccactcca cgacagctgt tttgaaggaa gcgaccacac   3780
atgtgactgc cgtaggcagc ataacactac attttagcac atcgagccca caagcaaatt   3840
ttatagtttc gctatgcggc aagaagtcca cctgcaatgc tgaatgtaaa ccaccggccg   3900
accacataat tggagaacca cataaagtcg accaagaatt ccaggcggca gtttccaaaa   3960
```

```
catcttggaa ctggctgctt gcactgtttg ggggagcatc atccctcatt gttgtaggac    4020
ttatagtgtt ggtctgcagc tctatgctta taaacacacg tagatgactg agcgcggaca    4080
ctgacatagc ggtaaaactc gatgtacttc cgaggaagcg tggtgcataa tgccacgcgc    4140
cgcttgacac taaaactcga tgtatttccg aggaagcaca gtgcataatg ctgtgcagtg    4200
tcacattaat cgtatatcac actacatatt aacaacacta tatcactttt atgagactca    4260
ctatgggtct ctaatataca ctacacatat tttacttaaa aacactatac acactttata    4320
aattctttta taatttttct tttgctttag agcacactgg cggccgttac tagtggatcc    4380
gagctctaga gggcc                                                    4395
```

<210> SEQ ID NO 8
<211> LENGTH: 23
<212> TYPE: DNA
<213> ORGANISM: Artificial Sequence
<220> FEATURE:
<223> OTHER INFORMATION: DNA Primer

<400> SEQUENCE: 8
ggtagattga tgtcggtgca tgg                                            23

<210> SEQ ID NO 9
<211> LENGTH: 30
<212> TYPE: DNA
<213> ORGANISM: Artificial Sequence
<220> FEATURE:
<223> OTHER INFORMATION: DNA Primer

<400> SEQUENCE: 9
gtacttgact gactgttttt ttttttttt                                      30

<210> SEQ ID NO 10
<211> LENGTH: 30
<212> TYPE: DNA
<213> ORGANISM: Artificial Sequence
<220> FEATURE:
<223> OTHER INFORMATION: DNA Primer

<400> SEQUENCE: 10
aatcaccctc tacggctgac ctaaataggt                                     30

<210> SEQ ID NO 11
<211> LENGTH: 24
<212> TYPE: DNA
<213> ORGANISM: Artificial Sequence
<220> FEATURE:
<223> OTHER INFORMATION: DNA Primer

<400> SEQUENCE: 11
ggctgagctc aataggtgac gtag                                           24

<210> SEQ ID NO 12
<211> LENGTH: 30
<212> TYPE: DNA
<213> ORGANISM: Artificial Sequence
<220> FEATURE:
<223> OTHER INFORMATION: DNA Primer

<400> SEQUENCE: 12
gtagtgtata ttagagaccc atagtgagtc                                     30

<210> SEQ ID NO 13

```
<211> LENGTH: 20
<212> TYPE: DNA
<213> ORGANISM: Artificial Sequence
<220> FEATURE:
<223> OTHER INFORMATION: DNA Primer

<400> SEQUENCE: 13
tccagatacg agctcatact                                               20

<210> SEQ ID NO 14
<211> LENGTH: 20
<212> TYPE: DNA
<213> ORGANISM: Artificial Sequence
<220> FEATURE:
<223> OTHER INFORMATION: DNA Primer

<400> SEQUENCE: 14
ggtgccgctg gaggccgttt                                               20

<210> SEQ ID NO 15
<211> LENGTH: 20
<212> TYPE: DNA
<213> ORGANISM: Artificial Sequence
<220> FEATURE:
<223> OTHER INFORMATION: DNA Primer

<400> SEQUENCE: 15
gatcttagga ggtcgatagc                                               20

<210> SEQ ID NO 16
<211> LENGTH: 20
<212> TYPE: DNA
<213> ORGANISM: Artificial Sequence
<220> FEATURE:
<223> OTHER INFORMATION: DNA Primer

<400> SEQUENCE: 16
ggctgatgaa accactccac                                               20

<210> SEQ ID NO 17
<211> LENGTH: 20
<212> TYPE: DNA
<213> ORGANISM: Artificial Sequence
<220> FEATURE:
<223> OTHER INFORMATION: DNA Primer

<400> SEQUENCE: 17
ccacccgtgt gctattcact                                               20

<210> SEQ ID NO 18
<211> LENGTH: 20
<212> TYPE: DNA
<213> ORGANISM: Artificial Sequence
<220> FEATURE:
<223> OTHER INFORMATION: DNA Primer

<400> SEQUENCE: 18
cgccgtgttt cagcccaata                                               20

<210> SEQ ID NO 19
<211> LENGTH: 20
<212> TYPE: DNA
<213> ORGANISM: Artificial Sequence
<220> FEATURE:
<223> OTHER INFORMATION: DNA Primer

<400> SEQUENCE: 19
```
tcacgagcgg agcatctgag          20

<210> SEQ ID NO 20
<211> LENGTH: 20
<212> TYPE: DNA
<213> ORGANISM: Artificial Sequence
<220> FEATURE:
<223> OTHER INFORMATION: DNA Primer

<400> SEQUENCE: 20
ggcatcaccc tccacctgac          20

<210> SEQ ID NO 21
<211> LENGTH: 20
<212> TYPE: DNA
<213> ORGANISM: Artificial Sequence
<220> FEATURE:
<223> OTHER INFORMATION: DNA Primer

<400> SEQUENCE: 21
ttgttattct gttccgctgc          20

<210> SEQ ID NO 22
<211> LENGTH: 20
<212> TYPE: DNA
<213> ORGANISM: Artificial Sequence
<220> FEATURE:
<223> OTHER INFORMATION: DNA Primer

<400> SEQUENCE: 22
ctattgatca tgcagtcgca          20

<210> SEQ ID NO 23
<211> LENGTH: 20
<212> TYPE: DNA
<213> ORGANISM: Artificial Sequence
<220> FEATURE:
<223> OTHER INFORMATION: DNA Primer

<400> SEQUENCE: 23
agtggagcct ctgcgagcgt          20

<210> SEQ ID NO 24
<211> LENGTH: 20
<212> TYPE: DNA
<213> ORGANISM: Artificial Sequence
<220> FEATURE:
<223> OTHER INFORMATION: DNA Primer

<400> SEQUENCE: 24
gaggagtggg cgggaaaggc          20

<210> SEQ ID NO 25
<211> LENGTH: 20
<212> TYPE: DNA
<213> ORGANISM: Artificial Sequence
<220> FEATURE:
<223> OTHER INFORMATION: DNA Primer

<400> SEQUENCE: 25
ctaaaactcg atgtatttcc          20

<210> SEQ ID NO 26
<211> LENGTH: 20
<212> TYPE: DNA

<213> ORGANISM: Artificial Sequence
<220> FEATURE:
<223> OTHER INFORMATION: DNA Primer

<400> SEQUENCE: 26
acgcgaacga agatgaacgg					20

<210> SEQ ID NO 27
<211> LENGTH: 20
<212> TYPE: DNA
<213> ORGANISM: Artificial Sequence
<220> FEATURE:
<223> OTHER INFORMATION: DNA Primer

<400> SEQUENCE: 27
actgtcattg tgctgtgtgg					20

<210> SEQ ID NO 28
<211> LENGTH: 20
<212> TYPE: DNA
<213> ORGANISM: Artificial Sequence
<220> FEATURE:
<223> OTHER INFORMATION: DNA Primer

<400> SEQUENCE: 28
cacagtcatt ccttcaccac					20

<210> SEQ ID NO 29
<211> LENGTH: 20
<212> TYPE: DNA
<213> ORGANISM: Artificial Sequence
<220> FEATURE:
<223> OTHER INFORMATION: DNA Primer

<400> SEQUENCE: 29
cgtcatcaga aagggcttg					20

<210> SEQ ID NO 30
<211> LENGTH: 20
<212> TYPE: DNA
<213> ORGANISM: Artificial Sequence
<220> FEATURE:
<223> OTHER INFORMATION: DNA Primer

<400> SEQUENCE: 30
caaagctgac agggagggac					20

<210> SEQ ID NO 31
<211> LENGTH: 20
<212> TYPE: DNA
<213> ORGANISM: Artificial Sequence
<220> FEATURE:
<223> OTHER INFORMATION: DNA Primer

<400> SEQUENCE: 31
ggaaagctgg taaagtgcca					20

<210> SEQ ID NO 32
<211> LENGTH: 20
<212> TYPE: DNA
<213> ORGANISM: Artificial Sequence
<220> FEATURE:
<223> OTHER INFORMATION: DNA Primer

<400> SEQUENCE: 32
ggagaaccac ataaagtcga					20

```
<210> SEQ ID NO 33
<211> LENGTH: 25
<212> TYPE: DNA
<213> ORGANISM: Artificial Sequence
<220> FEATURE:
<223> OTHER INFORMATION: DNA Primer

<400> SEQUENCE: 33
ggctaacgtg gacagggacg tgatg                                                25

<210> SEQ ID NO 34
<211> LENGTH: 20
<212> TYPE: DNA
<213> ORGANISM: Artificial Sequence
<220> FEATURE:
<223> OTHER INFORMATION: DNA Primer

<400> SEQUENCE: 34
ggctatcgac ctcctaagat                                                     20

<210> SEQ ID NO 35
<211> LENGTH: 20
<212> TYPE: DNA
<213> ORGANISM: Artificial Sequence
<220> FEATURE:
<223> OTHER INFORMATION: DNA Primer

<400> SEQUENCE: 35
ctgtcggttc cctggtttag                                                     20

<210> SEQ ID NO 36
<211> LENGTH: 20
<212> TYPE: DNA
<213> ORGANISM: Artificial Sequence
<220> FEATURE:
<223> OTHER INFORMATION: DNA Primer

<400> SEQUENCE: 36
ctggggaacg tcgccatact                                                     20

<210> SEQ ID NO 37
<211> LENGTH: 20
<212> TYPE: DNA
<213> ORGANISM: Artificial Sequence
<220> FEATURE:
<223> OTHER INFORMATION: DNA Primer

<400> SEQUENCE: 37
cgttctccag cagcgtgtcg                                                     20

<210> SEQ ID NO 38
<211> LENGTH: 20
<212> TYPE: DNA
<213> ORGANISM: Artificial Sequence
<220> FEATURE:
<223> OTHER INFORMATION: DNA Primer

<400> SEQUENCE: 38
tattgggctg aaacacggcg                                                     20

<210> SEQ ID NO 39
<211> LENGTH: 20
<212> TYPE: DNA
<213> ORGANISM: Artificial Sequence
<220> FEATURE:
```

<223> OTHER INFORMATION: DNA Primer

<400> SEQUENCE: 39
cttcaagtga tcgtaaacgt                    20

<210> SEQ ID NO 40
<211> LENGTH: 20
<212> TYPE: DNA
<213> ORGANISM: Artificial Sequence
<220> FEATURE:
<223> OTHER INFORMATION: DNA Primer

<400> SEQUENCE: 40
actccagccc ttctcgcccc                    20

<210> SEQ ID NO 41
<211> LENGTH: 20
<212> TYPE: DNA
<213> ORGANISM: Artificial Sequence
<220> FEATURE:
<223> OTHER INFORMATION: DNA Primer

<400> SEQUENCE: 41
gttcgaccaa cgccttatac                    20

<210> SEQ ID NO 42
<211> LENGTH: 20
<212> TYPE: DNA
<213> ORGANISM: Artificial Sequence
<220> FEATURE:
<223> OTHER INFORMATION: DNA Primer

<400> SEQUENCE: 42
aagggtgaaa aagcggctga                    20

<210> SEQ ID NO 43
<211> LENGTH: 20
<212> TYPE: DNA
<213> ORGANISM: Artificial Sequence
<220> FEATURE:
<223> OTHER INFORMATION: DNA Primer

<400> SEQUENCE: 43
ggtgattctg atgatctcac                    20

<210> SEQ ID NO 44
<211> LENGTH: 20
<212> TYPE: DNA
<213> ORGANISM: Artificial Sequence
<220> FEATURE:
<223> OTHER INFORMATION: DNA Primer

<400> SEQUENCE: 44
tggaaactgc cgcctggaat                    20

<210> SEQ ID NO 45
<211> LENGTH: 20
<212> TYPE: DNA
<213> ORGANISM: Artificial Sequence
<220> FEATURE:
<223> OTHER INFORMATION: DNA Primer

<400> SEQUENCE: 45
ccttgatgtc atggtcgtgg                    20

```
<210> SEQ ID NO 46
<211> LENGTH: 20
<212> TYPE: DNA
<213> ORGANISM: Artificial Sequence
<220> FEATURE:
<223> OTHER INFORMATION: DNA Primer

<400> SEQUENCE: 46
tgcactgagt ggtctgtgtg                                              20

<210> SEQ ID NO 47
<211> LENGTH: 20
<212> TYPE: DNA
<213> ORGANISM: Artificial Sequence
<220> FEATURE:
<223> OTHER INFORMATION: DNA Primer

<400> SEQUENCE: 47
atgtttcagc gttggttggc                                              20

<210> SEQ ID NO 48
<211> LENGTH: 20
<212> TYPE: DNA
<213> ORGANISM: Artificial Sequence
<220> FEATURE:
<223> OTHER INFORMATION: DNA Primer

<400> SEQUENCE: 48
gtgttctcac tgtcacagaa                                              20

<210> SEQ ID NO 49
<211> LENGTH: 20
<212> TYPE: DNA
<213> ORGANISM: Artificial Sequence
<220> FEATURE:
<223> OTHER INFORMATION: DNA Primer

<400> SEQUENCE: 49
atgtgtggtc gcttccttca                                              20
```